US011866769B2

(12) United States Patent
Thrippleton et al.

(10) Patent No.: US 11,866,769 B2
(45) Date of Patent: Jan. 9, 2024

(54) ENHANCED MULTIPLEX FISH

(71) Applicant: MIACOM DIAGNOSTICS GmbH, Duesseldorf (DE)

(72) Inventors: Ian Peter Thrippleton, Kaarst (DE); Walter Freiherr Von Stein, Duesseldorf (DE)

(73) Assignee: MIACOM DIAGNOSTICS GMBH, Duesseldorf (DE)

( * ) Notice: Subject to any disclaimer, the term of this patent is extended or adjusted under 35 U.S.C. 154(b) by 0 days.

(21) Appl. No.: 14/151,111

(22) Filed: Jan. 9, 2014

(65) Prior Publication Data

US 2014/0194316 A1 Jul. 10, 2014

Related U.S. Application Data

(63) Continuation of application No. 13/582,651, filed as application No. PCT/EP2011/053341 on Mar. 4, 2011, now abandoned.

(30) Foreign Application Priority Data

Mar. 4, 2010 (EP) .................................... 10155508

(51) Int. Cl.
*C12Q 1/6876* (2018.01)
*C12Q 1/6837* (2018.01)
*C12Q 1/6841* (2018.01)

(52) U.S. Cl.
CPC ......... *C12Q 1/6837* (2013.01); *C12Q 1/6841* (2013.01)

(58) Field of Classification Search
None
See application file for complete search history.

(56) References Cited

U.S. PATENT DOCUMENTS 5,030,557 A 7/1991 Hogan et al.
2002/0055116 A1* 5/2002 Cunningham ....... C12Q 1/6895 435/6.15
2002/0090626 A1* 7/2002 Hyldig-Nielsen ..... C12Q 1/689 435/6.15
2002/0106644 A1* 8/2002 Rosenow ............. C12Q 1/6876 435/6.14
2003/0096252 A1* 5/2003 Jacobsen .............. C12Q 1/6834 435/6.18
2003/0129611 A1* 7/2003 Bao ...................... C12Q 1/6818 435/6.11
2003/0165884 A1* 9/2003 Chow .................. C12Q 1/6881 435/6.11
2004/0191812 A1* 9/2004 Davydova ............ C12Q 1/6862 506/10
2004/0235138 A1 11/2004 Weisburg et al.
2006/0194222 A1* 8/2006 Sorge ................... C12Q 1/6839 435/6.11
2007/0059743 A1* 3/2007 Maass Sepulveda ... G06F 19/20 435/6.18
2008/0050718 A1* 2/2008 Gesteland .............. G16B 25/00 435/5
2009/0170076 A1* 7/2009 Taylor .................... C12Q 1/689 435/6.11
2009/0203007 A1 8/2009 Jonas
2009/0324559 A1* 12/2009 Sakurada .................. A61P 3/10 424/93.7
2011/0020823 A1* 1/2011 Burns ............................... 435/6

FOREIGN PATENT DOCUMENTS

WO 1992/014841 9/1992
WO 2008/043543 A2 4/2008

OTHER PUBLICATIONS

"Plant," (Wikipedia.com; accessed Mar. 8, 2013).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*
"Pathogen," Wikipedia.com, accessed Apr. 27, 2017.*
"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"List of sequenced bacterial genomes" (Wikipedia.com; accessed Jan. 24, 2014).*
"Aspergillus", Wikipedia.com, accessed Mar. 11, 2019. (Year: 2019).*
Forster et al., "A human gut bacterial genome and culture collection for improved metagenomic analysis", Nature Biotechnology, vol. 37, Feb. 2019, pp. 186-192. (Year: 2019).*
"How many species of bacteria are there" (wisegeek.com; accessed Jan. 21, 2014. (Year: 2014).*
"Fungi," Wikipedia.com; accessed Jun. 3, 2013. (Year: 2013).*
"Archaea," Wikipedia.com, accessed May 11, 2016. (Year: 2016).*
"Algae," Wikipedia.com, accessed Mar. 4, 2016. (Year: 2016).*
"Protozoa," Wikipedia.com, accessed May 11, 2016. (Year: 2016).*
"List of sequenced bacterial genomes", Wikipedia.com; accessed Jan. 24, 2014. (Year: 2014).*
Peng X-H et al: "Real-time Detection of Gene Epression in Cancer Cells Using Molecular Beacon Imaging: New Strategies for Cancer Research", in: Cancer Research, American Association for Cancer Rerearch, vol. 65, No. 5, Mar. 1, 2005, pp. 1909-1917.
Weckx Stefan et al: "Thermodynamic behavior of short oligonucleotides in microarray hybridizations can be described using Gibbs free energy in a nearest-neighbor model.", in: The Journal of Physical Chemistry. B Dec. 6, 2007, vol. 111, No. 48, Dec. 6, 2007, pp. 13583-13590.
Antje Rusch et al: "Functional Characterization of the Microbial Community in Geothermal ly Heated Marine Sediments" in: Microbial Ecology, Springer-Verlag, NE, vol. 55, No. 4, Sep. 14, 2007, pp. 723-736.

(Continued)

*Primary Examiner* — Bradley L. Sisson
(74) *Attorney, Agent, or Firm* — Agris & von Natzmer LLP; Joyce von Natzmer

(57) ABSTRACT

Subject of the present invention is a combination of nucleic acid molecules capable of hybridizing with a target nucleic acid sequence. In order to overcome problems with the reproducibility of FISH assays and to decrease assay time, hairpin probes are used in combination with helper probes annealing adjacent to the target site of the hairpin probe.

26 Claims, 3 Drawing Sheets

Figure 1:
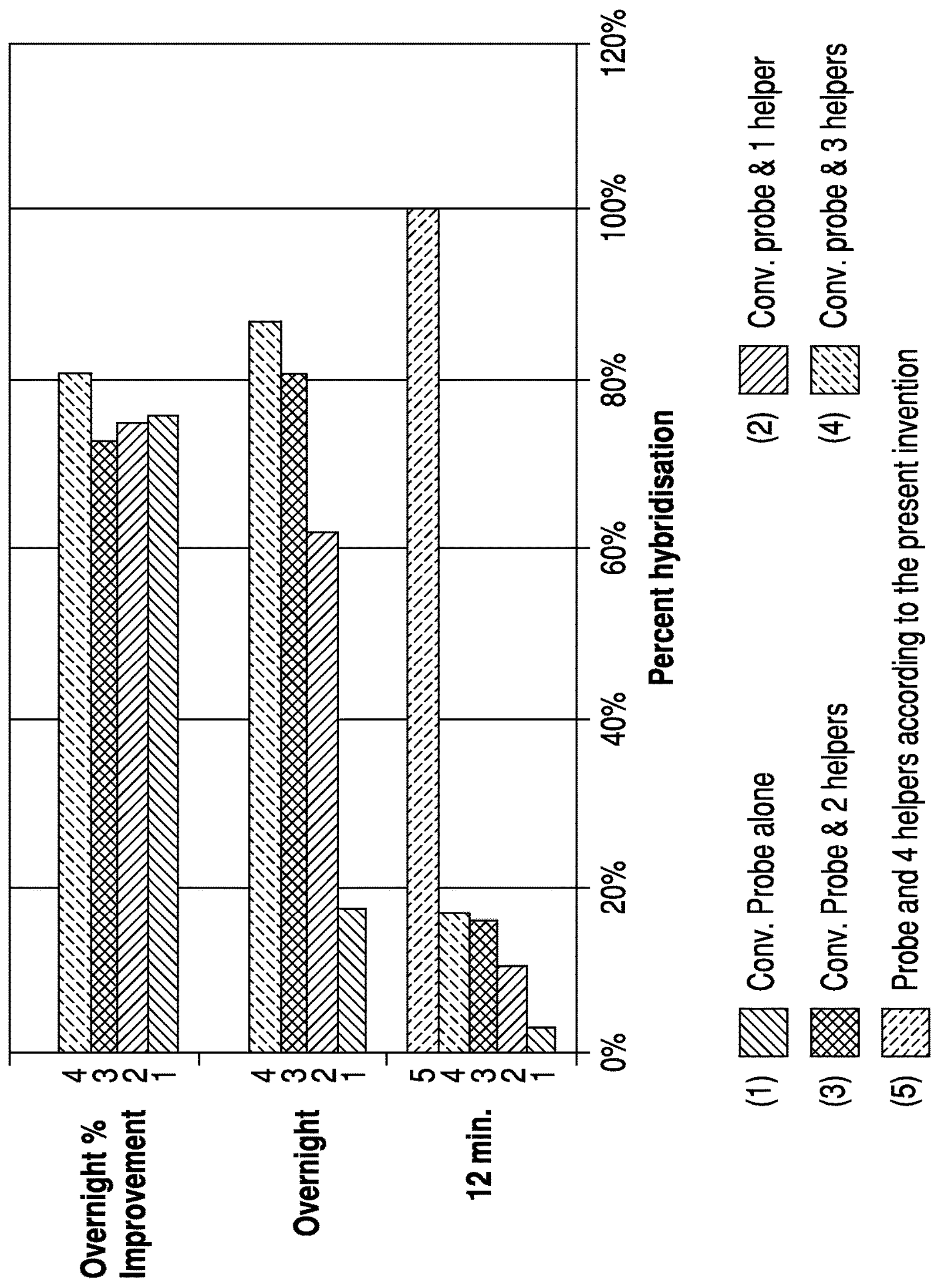

Specification includes a Sequence Listing.

(56) References Cited

OTHER PUBLICATIONS

Fuchs et al: "Unlabeled Helper Oligonucleotides Increase the In Situ Accessibility to 16S rRNA of Fluorescently Labeled Oligonucleotide Probes" in: Applied and Environmental Microbiology, vol. 66, No. 8, 2000, pp. 3603-3607.

Fuchs et al: "Flow Cytometric Analysis of the In Situ Accessibility of *Escherichia coli* 16S rRNA for Fluorescently Labeled Oligonucleotide Probes" in: Applied and Environmental Microbiology, vol. 64, No. 12, 1998, pp. 4973-4982.

Fuchs et al: "In Situ Accessibility of *Escherichia coli* 23S rRNA to Fluorescently Labeled Oligonucleotide Probes" in: Applied and Environmental Microbiology, vol. 67, No. 2, 2001, pp. 961-968.

Sekar et al: "Comparative Study of Sequence-Dependent Hybridization Kinetics in Solution and on Microspheres" in: Nucleic Acids Research, vol. 33, No. 1, 2005, pp. 366-375.

Amann et al: "Phylogenetic Identification and In Situ Detection of Individual Microbial Cells without Cultivation" in: Microbiological Reviews, vol. 59, No. 1, 1995, pp. 143-169.

Shchepinov et al: "Steric Factors Influencing Hybridisation of Nucleic Acids to Oligonucleotide Arrays" in: Nucleic Acids Research, vol. 25, No. 6, 1997, pp. 155-1161.

"How many species of bacteria are there," (wisegeek.com, accessed Sep. 23, 2011).

* cited by examiner

Kinetics of Hybridisation
Fluorescence
5
4
3
2
1
0
0.5
4
8
12 min
(1)
(2)
(3)
(4)
(1) E. coli with helper
(2) E. coli without helper
(3) Strep B with helper
(4) Strep B without helper

ENHANCED MULTIPLEX FISH

The present invention relates to the multiplexed usage of hairpin loops for fluorescent in-situ hybridisation and the enhancement of reproducibility, specificity, and speed of assay. A first aspect of the present invention is a combination of nucleic acid molecules capable of hybridising with a target nucleic acid sequence, wherein the combination comprises (a) at least one nucleic acid comprising a sequence capable of forming a hair pin loop (e.g. a molecular beacon), and (b) a second nucleic acid molecule, a third nucleic acid molecule, and optionally at least one further nucleic acid molecule being helper nucleic acids.

Rapid identification of pathogenic organisms in clinical samples is of ever increasing importance in order to reduce mortality, morbidity and cost of treating infectious diseases. The breakthrough in applying DNA-beacon technology to in-situ hybridisation applications (1) allows FISH-technology to compete with PCR systems and micro-array technology in terms of speed and surpass in cost efficiency. The objective of this invention was to find ways to solve the reproducibility problem FISH has been experiencing and further increase the speed of the assay time.

In order to increase the speed of an assay, the dynamics of the assays need to be analysed (2). In PCR-assays all components involved in the hybridisation are in homogeneous solution and follow 2nd order kinetics. Micro-arrays follow pseudo first-order rate, as the capturing oligonucleotides are fixed to the solid phase and the analytes are in solution (3). In FISH the respective roles are exchanged (i.e. the analyte is fixed to the solid phase, and the oligonucleotides are in solution), however, the configuration is similar from the kinetic point of view. The rate constants measured when probes were attached to a solid phase were as much as three orders of magnitude lower than those measured in solution (3). It therefore cannot be expected that the in-situ hybridisation kinetics can be brought to be in the same order of magnitude as in homogeneous solution.

The kinetic properties of hybridisation assays of the state of the art can be summarized as follows:

| Assay | Amplification assays | Micro-array assays | FISH |
|---|---|---|---|
| Probe | In solution | Solid phase with secondary structures | In solution |
| Analyte | In solution | In solution | deeply embedded in fixed RNA/protein macromolecules |
| Kinetics | Second order rate | Pseudo first-order rate (3) | More comparable to micro-array assembly Expectation is = to micro-array to pseudo-first order rate |

Intrinsic problems of PCR lie in its sensitivity and proneness to inhibitors. In PCRs on clinical samples the DNA/RNA is extracted from very crude and extremely variable matrices that frequently harbour polymerase inhibiting components. Such inhibitors may generate undesirable false negative results. FISH does not require enzymes to generate a signal and is therefore not under such limitations.

Micro-array technology involves fixation of known sequences to a solid-phase support. When used for the hybridisation towards ribosomal RNA it must deal with the issue of accessibility of the target sequence within a large RNA molecule exhibiting secondary and tertiary structures. Fuchs et al have shown diligently, that regions in both the 16S and 23S rRNA are accessible to varying degrees (4, 5). This can range from an easily accessible (Fuchs score I) site to a completely inaccessible site (Fuchs score VI). The inaccessibility of regions limits the sites that can be chosen for species specificity. Equally, the inaccessible regions show the greatest variability and would be the most desirable targets for species specific probes. Moreover, trying to use an even partially inaccessible sequence introduces fluctuation in hybridisation results as a highly undesirable variable in the assay.

As FISH-probes also have to hybridise towards the complex structure of an intact ribosome, it also carries the same burden. Moreover, hybridising linear probes to accessible sites may also cause quenching due to interactions of the fluorophor with the protein/RNA complex. In such cases varying amounts of between only 1% and 20% of the total number of organisms present fluorescence. The interpretation of results with this variable requires extensive knowledge and reading experience. Other experimental variables such as the sample preparation and temperature fluctuation make FISH prone to generating false negative results. Diligent controls must be incorporated in order to get a reliable result. Care must be taken in the probe design so that secondary structures will not inhibit a probes access to a specific sequence. This is a challenge, as most species specific sequences lie in variable regions with poor accessibility (6). Additionally, if the temperature during the hybridisation and washing is not controlled precisely, no hybridisation will occur and a false negative may be generated. Initial enthusiasm in the use of FISH assays was soon replaced with frustration due to the erratic performance.

FISH may generate false positive results (a) by inadequate reading of auto fluorescence (b) by inadequate reading of particulate matter originating from the sample (c) when using linear probes, inadequate washing is the most frequent source of false positives (d) inadequate probe design may allow cross-reactivity with closely related organisms (7).

The sheer analytical sensitivity of amplification assays renders it prone to DNA/RNA contamination occurring during sample taking or in the lab, which in turn generates false positive results. False positives may be reduced by using complex closed systems.

For FISH technology to compete, its procedure and hybridisation conditions need to be stream-lined with respect to assay handling, kinetics and hybridisation procedure. Solutions must be found to ensure sensitivity and specificity as well as speed of energy transfer and hybridisation kinetics, thus eliminating the problems in FISH and significantly enhancing the performance.

Fuchs et al. showed the usage of helper oligonucleotides as an increase in signal from a weak 4-7% to 75% of an optimal signal using the standard hybridisation time of at least 90 min in 16S RNA of suspended *E. coli* cells (6). Fluorescing *E. coli* cells were detected by flow cytometry. The teachings of Fuchs et al are that helper-oligonucleotides may increase the signal when placed in the vicinity with respect to the secondary and tertiary structure, suggesting that by joint action of multiple adjacent helper oligonucleotides, every site on the rRNA can be opened for FISH. However, the teachings do not show conformity in the usage generating variable results. In some cases four adjacent helpers reduced the signal with respect the signal of two helpers.

Fuchs (6) described the different efficiency of a range of helpers, and found that the helpers adjacent to the probe were most efficient in this region. On the basis of these data, one would expect that the optimal position for helpers would vary from organism to organism according the respective differences in sequence and position of the target within the rRNA.

A signal limiting factor is the number of ribosomes present in an organism. This in turn depends on how an organism reacts to stressful conditions. It is well known in the art that under stressful conditions, the number of ribosomes is down-regulated, changing the signal strength in FISH from a full 4+ to a very weak signal (7).

U.S. Pat. No. 5,030,557 describes hybridisations experiments performed in solution employing isolated ribosomal RNA as target (8). Helper oligonucleotides are used to enhance the binding of labelled oligonucleotides to ribosomal RNA. However, this required an overnight incubation to achieve an enhanced signal. In addition, U.S. Pat. No. 5,030,557 call for a 50-200 fold higher concentration of each helper to achieve the improvement (8). Adding a further helper increased the signal by 20% and the further addition of a third helper only increased the signal by a further 7%. The data of U.S. Pat. No. 5,030,557 are summarized in FIG. 1.

In summary, rapid identification of pathogenic microorganisms by hybridisation hampered by the following shortcomings Microarray methods have been found to require long incubation times.

PCR methods are faster than microarray methods. PCR requires a polymerase which may be inhibited when exposed to a crude sample. Thus, clinical samples should be purified prior to PCR.

In-situ methods, such as FISH, may be hampered by accessibility of the target sequence in the cell to be identified. No uniform hybridisation conditions exist. Rather, in-situ methods require adaptation of hybridisation conditions in each new target sequence or/and organism. Experimental conditions of in-situ methods have to be controlled very carefully in order to avoid false negative or false positive results. Further, in-situ methods require long incubation times.

In the present invention, it was surprisingly found that a full 100% signal can be achieved in a FISH assay on cells fixed to a surface by a combination comprising a molecular beacon and at least two helper oligonucleotides in 8 minutes—irrespective of position within the rRNA and organism chosen. It was further surprising that the usage of the helpers together with the beacon as laid out in this invention produced a reproducible homogeneous staining of all organisms with full signal strength.

It was surprising that the said stringent design of beacon-helper arrays and assay conditions removed the problems FISH procedures had encountered.

It is the purpose of this invention to find universal rules for the combination of helper sequences in conjunction with molecular beacons for in-situ hybridisation and overcoming thermodynamic restrictions and heat transfer that hitherto have restricted hybridisation kinetics in FISH.

A first aspect of the present invention is a combination of nucleic acid molecules capable of hybridising with a target nucleic acid sequence, wherein the combination comprises (a) at least one first nucleic acid molecule comprising (i) a sequence capable of hybridising with the target sequence, (ii) two complementary sequences capable of forming a stem, and (iii) a luminescent group and a quencher group, wherein the quencher group quenches the fluorescent group if the nucleic acid forms a stem-loop structure, and wherein the fluorescent group is capable of emitting a luminescence signal upon excitation if the oligonucleotide is hybridised with the target sequence, (b) a second nucleic acid molecule, a third nucleic acid molecule, and optionally at least one further nucleic acid molecule, wherein the second nucleic acid molecule, the third nucleic acid molecule, and the optional at least one further nucleic acid molecule hybridise with the target sequence at a sequence located 5' or/and 3' from the sequence to which the at least one first nucleic acid hybridises.

The at least one first nucleic acid of the present invention capable of forming a hybrid with a target nucleic acid sequence and capable of forming a stem-loop structure if no hybrid is formed with the target sequence is also referred herein as "beacon", "molecular beacon", "hairpin", or "hairpin loop", wherein the "open" form (no stem is formed) as well as the "closed" form (a stem is formed) is included. The open form includes a beacon not forming a hybrid with the target sequence and a beacon forming a hybrid with the target sequence.

In particular, the first nucleic acid molecule comprises a sequence capable of forming a hair-pin loop, e.g. a molecular beacon.

Sequence (i) of the first nucleic acid molecule is also termed herein as "probe sequence" or "probe sequence of the molecular beacon".

If more than one first nucleic acid is present, the sequences to which the two or more first nucleic acids hybridise may be independently located directly adjacent to each other, or may be independently separated by a gap of at is least one nucleotide, such as one, two, three, four, five or even more nucleotides. The sequences to which the two or more first nucleic acids hybridise may also be separated by a gap large enough that one or more helpers may hybridise with the sequence within the gap.

If more than one first nucleic acid is present, they may be directed against the same gene. In other words, if more than one first nucleic acid is present, the target sequences of the more than one first nucleic acid may be selected from sequences obtained from the same gene. Preferably, these sequences are non-overlapping. This allows the detection of individual genes without amplification.

If more than one first nucleic acid is present, they may be directed against the expression product mRNA of the same gene. In other words, if more than one first nucleic acid is present, the target sequences of the more than one first nucleic acid may be selected from sequences obtained from the mRNA expressed by the same gene. Preferably, these sequences are non-overlapping. This allows the detection of individual genes without amplification.

In the present invention, "located directly adjacent to each other" means that no gap is left if the nucleic acid molecules hybridise at adjacent positions on the target sequence.

The second nucleic acid, the third nucleic acid, and the at least one further nucleic acid are termed herein "helpers" or "helper nucleic acids" or "helper oligonucleotides".

The cognate sequences of the helpers designed in this invention may be placed in close vicinity on the 5' or/and 3' end of the cognate sequence of the beacon. A multiplicity of helpers may be used, however full signal strength may be achieved with either two, three or four helpers. The combination of the present invention preferably comprises two, three, four, five, six, seven, eight or ten helper nucleic acids. Preferably, the combination of the present invention comprises two, three, four helper nucleic acids.

The nucleic acids of a combination of the present invention may hybridise with the target sequence at locations directly adjacent to each other, or may be independently separated by a gap of at least one nucleotide, such as one, two, three, four, five or even more nucleotides. For instance, at least two nucleic acid molecules may hybridise with the target sequence at locations separated from each other by a gap of at least one nucleotide, such as one, two, three, four, five or even more nucleotides.

More preferably, the combination of the present invention comprises four helper nucleic acids. In the most preferred configuration the cognate sequences of four helpers are located directly adjacent, without a gap next to the cognate sequence of the beacon and directly adjacent to each other, two to the 5' flank and two to the 3' end of the cognate sequence of the beacon. An Example is given in FIG. 3. In this design, the target sequences position and accessibility according to Fuchs may be disregarded.

The target sequence may be selected so that the sequences to which the at least one first, the second, the third and the optional at least one further nucleic acid molecules hybridise are non-overlapping sequences of the target sequence.

Figure 3:
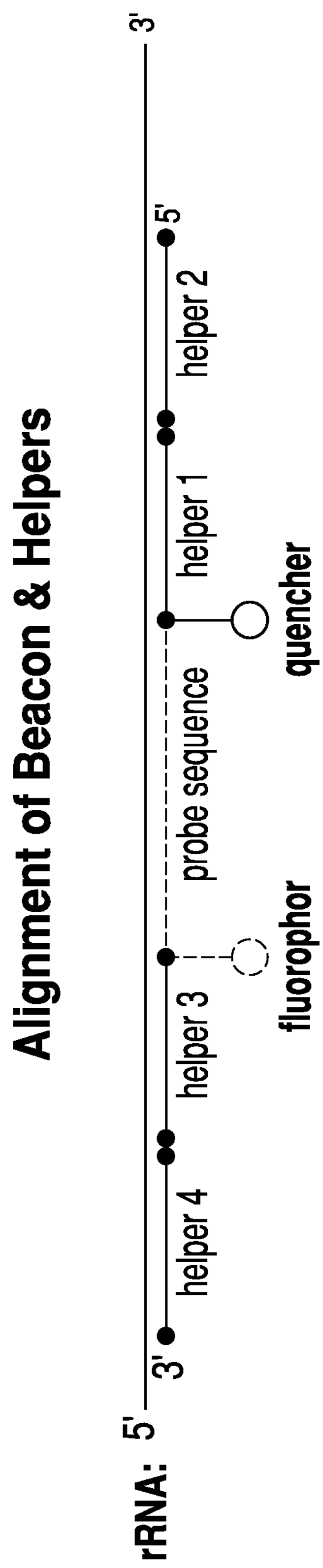

An exemplary configuration is described in FIG. 3. Helpers termed "1" and "2" extend from the 5' end and helpers termed "3" and "4" extend from the 3' end of the beacon's probe sequence forcing the stem-part of the beacon away from the ribosome and to function as a spacer. Helpers 2 and 4 are placed next to helpers 1 and 3 on the respective 5' and 3' ends equally without a gap. In order to achieve maximum synergism in hybridisation, all probe and helper sequences may carry the same thermodynamic properties with respect to the binding to cognate sequences. This stringent selection of oligonucleotides allows the orchestration of the mass hybridisation action covering the length of 100 bases (e.g. between 89 and 120) of the ribosomal RNA for the reproducible opening of ribosomal RNA with the fast kinetics and high specificity of small 20-mer (16-26-mer) oligonucleotides—all operating to the same said stringent conditions.

The sequence of the target sequence to which a nucleic acid of the present invention hybridises is termed herein as "cognate sequences" of the respective nucleic acid. For example, the cognate sequence of a first nucleic acid (i.e. a molecular beacon) is that sequence of the target sequence to which sequence (i), as indicated herein, hybridises. A hybrid of a nucleic acid molecules of the combination of the present invention with the target sequence is also referred herein as "hybrid with the cognate sequence" or as "cognate hybrid".

The target nucleic acid sequence employed in the various embodiments of the present invention may be a nucleic acid sequence of a cell. The cell may be a eukaryotic cell or a prokaryotic cell. The cell may be any cell which can be present in a biological or clinical sample. In particular, the target nucleic acid sequence may be a nucleic acid sequence of a micro-organism, such as a micro-organism selected from bacteria, yeasts and moulds, in particular from Gram positive or/and Gram negative bacteria. Depending on the disease state certain pathogens most frequently are the causative agents and can thus be compiled into diagnostic groups. Addition or omission of certain pathogens may be required depending on regional epidemiology in order to reach the 95-percentile. The listing of Table 1 covers the requirements of Europe and most of North America. The micro-organism is preferably selected from the organisms listed in Table 1 and Table 4.

The cell employed in the present invention may be kept in suspension or/and suspension culture.

The target nucleic acid sequence may be a DNA sequence or/and a RNA sequence, in particular an rRNA sequence, such as a bacterial 16S rRNA or/and a bacterial 23S rRNA sequence. The target nucleic acid sequence may also be an mRNA sequence.

In particular, the two complementary sequences (ii) of the first nucleic acid molecule are flanking the sequence (i), i.e. the first sequence of (ii) is located at the 3' end of the sequence (ii) and the second sequence of (ii) is located at the 5° end of the sequence (i).

The two complementary sequences of (ii) may independently have a length of 4 to 10 nucleotides, in particular 4, 5, 6, 7, 8, 9, 10 or even more nucleotides. Preferably, the two sequences of (ii) have the same length.

In the first nucleic acid molecule, the luminescent group may be attached at one of the two complementary sequences capable of forming a stem, whereas the quencher may be attached at the other of the two complementary sequences, so that the quencher essentially quenches the luminescence when a stem is formed, and that the luminescent can emit a luminescence signal when the hairpin is open.

Preferably, the luminescent group is independently attached at the 5' end of the at least one first nucleic acid molecule, or at a position which is 1, 2, 3, 4, 5 or 6 nucleotides distant to the 5' end. In this case, the quencher is independently attached at the other end not covered by the luminescent group, i.e. at the 3' end, or at a position which is 1, 2, 3, 4, 5 or 6 nucleotides distant to the 3' end.

It is also preferred that the luminescent group is independently attached at the 3' end of the at least one first nucleic acid molecule, or at a position which is 1, 2, 3, 4, 5 or 6 nucleotides distant to the 3' end. In this case, the quencher is independently attached at the other end not covered by the luminescent group, i.e. at the 5' end, or at a position which is 1, 2, 3, 4, 5 or 6 nucleotides distant to the 5' end.

The luminescent group may independently be coupled to the at least one first nucleic acid molecule by a linker. The quencher group may be independently coupled to the at least one first nucleic acid molecule by a linker. The skilled person knows suitable linkers. The linker may independently comprise at least one nucleotide.

The skilled person knows suitable luminescent group and quenchers. The luminescent group is preferably a fluorescent group. Suitable fluorescent groups may be independently selected from those readily commercially available absorbing from UV to the visible, to the IR light range and emitting with a Stokes shift enabling the physical separation of light due to excitation and emission. In the fluorescent group, autofluorescence may reduced via enhanced Stokes shift. Suitable fluorescent groups may independently be selected from FAM, Cy3, FITC and derivatives thereof.

Luminescence, in particular fluorescence, may be determined by microscopy, flow cytometry or any other suitable method known in the art. In cells kept in suspension or suspension culture, luminescence, in particular fluorescence, may be determined by flow cytometry.

Hybridisation of the beacon of the present invention with a target sequence may take place under conditions where the loop will unfold in presence of a cognate sequence. A beacon with a closed stem will provide higher specificity and compensate for the decrease due to the increase in sequence length.

This goal is achieved by choosing a stem sequence with a negative ΔG even under hybridisation conditions, but substantially higher (less negative) than the loop sequence (cognate DNA/RNA hybrid), and preferably in the absence of $Mg^{2+}$. Thus, the hybridisation with the target sequence may take place, when the stem is destabilised by the essentially $Mg^{2+}$ free conditions.

"Substantially higher ΔG" means a difference of the respective ΔGs of is between about −15 and about −25 kcal/mol, preferably between about −17 and about −23 kcal/mol and even more preferable between about −19 and about 21 kcal/mol.

In order to achieve quenching of the luminescent group, both of which form part of the beacon, in those beacon molecules not hybridising with the target sequence, stem formation must be induced after the hybridisation reaction. This may for instance be achieved by a beacon having a ΔG<0, so the hairpin will form spontaneously. Further, stem formation may be introduced by washing with a $Mg^{2+}$ containing buffer as described herein.

In particular, the hairpin loops are constructed in such a way that under standardised hybridisation conditions (e.g. under essentially $Mg^{2+}$ free conditions) the stem is open so that possible sterical limitations do not hinder the hybridisation process. For instance, sterical limitations may be present when the target sequence is a rRNA sequence. If the effector is a fluorophor, the fluorophor will not be quenched by the close proximity of ribosomal proteins.

Suitable conditions for induction of stem formation after hybridisation include an $Mg^{2+}$ containing buffer, for instance containing about 0.1 to about 20 mM $Mg^{2+}$, about 1 to about 20 mM $Mg^{2+}$, 5 to about 15 mM $Mg^{2+}$, about 8 to about 12 mM $Mg^{2+}$, about 1 mM to about 10 mM $Mg^{2+}$, about 2.5 mM to about 7.5 mM $Mg^{2+}$. Preferred is a concentration of about 5 mM $Mg^{2+}$ or about 10 mM $Mg^{2+}$. The buffer may have a pH>8, preferably of about 8.3. The pH may also be adjusted to about 7.5 to about 9 or about 8 to about 8.5.

Furthermore, the hair-pin loops function in their entirety and cannot be dissected. Stem and loop as nearest neighbour and stacking effect have a profound influence in their thermodynamic properties. Preferred nucleic acids of the present invention are described in Table 1, Table 3 and Table 4. They clearly show that the preferred stem sequence is independent from the ΔG, $T_m$, GC content or length of the sequence chosen to identify a species.

In the present invention, the thermodynamic specifications for the individual construction of nucleic acids employed in the combination of the present invention suitable for standardised conditions are set: The Gibbs energy (ΔG) for the formation of the nucleic acid may be designed in such a way that

- The hairpin stem will form spontaneously (ΔG<0) in the absence of a cognate target sequence under hybridisation conditions.
- The ΔG of the cognate hybrid is significantly lower (i.e. is more negative) than the ΔG of the hairpin stem.
- The respective ΔG of the cognate sequence is lower than a mismatch or non-cognate sequence.
- The $T_m$ for the formation of the hair-pin loop has to be designed in such a way that the $T_m$ of the hair-pin loop is lower than or essentially at the $T_m$ of the hybrid.

In particular, the nucleic acids of the combination of the present invention independently hybridise with the target sequence with a more negative ΔG than the ΔG generated by the natural refolding of the target sequence, which preferably is a target mRNA or target DNA sequence.

It is preferred that the ΔG of the cognate hybrid (i.e. the hybrid of a helper or/and molecular beacon of the present invention with its target sequence) is in the range of about −15 and about −25 kcal/mol, preferably between about −17 and about −23 kcal/mol and even more preferable between about −19 and about 21 kcal/mol under hybridisation conditions. The ΔG of the cognate hybrid may independently be adjusted for the nucleic acid molecules of a combination as described herein.

It is also preferred that the ΔG of at least two cognate hybrids under hybridisation conditions do not vary more than 5 kcal/mol, preferably no more than 3 kcal/mol, more preferably no more than 2 kcal/mol and most preferably no more than 1 kcal/mol. In particular, the ΔG of the cognate hybrids under hybridisation conditions do not vary more than 5 kcal/mol, preferably no more than 3 kcal/mol, more preferably no more than 2 kcal/mol and most preferably no more than 1 kcal/mol.

The nucleic acid molecules of the combination may independently hybridise with a target sequence, preferably with a target rRNA sequence, with a combined ΔG in the range of −60 to −150 kcal/mol, −80 to −150 kcal/mol, or −100 to −120 kcal/mol. Surprisingly, it was found that, using the stringent gap-free configuration of 5 nucleic acids (including one molecular beacon), the increase in signal strength up to a universally strong signal was achieved not only for the one region in *E. coli*, but strong signal enhancement could be achieved for numerous regions of both 16S and 23S rRNA in a wide range of organisms with the same kinetics. It is preferred to combine labelled and unlabelled oligonucleotides that all carry the same thereto-dynamic characteristics in such a way that they hybridise under identical conditions in all organisms with a combined and standardised ΔG=−60 to −150 kcal/mol without loss of single base discrimination capability.

The criteria for the selection of a probe assembly could thus be determined to be driven by sequence specificity first and secondly by the free energy (ΔG) generated upon hybridisation, disregarding $T_m$ as the hitherto driving thermodynamic parameter used in the art. As all helpers and beacons may be designed to have very similar characteristics, it was not only possible to have matched helpers together with a beacon, but also to generate multiple examples of said groupings, all working under identical conditions and binding to both 16S and 23S rRNA with closely similar kinetics. Effectively the free hybridisation energy of a 100mer generated may be used while maintaining the discriminatory specificity of for example short 18-26-mer oligonucleotides thus favouring the hybrid binding with a strong signal over the re-formation of the native ribosomal structure. Table 4 compiles the beacons designed together with their respective helpers together with the thermodynamic properties and the scoring according to Fuchs et al. (6).

Occasionally cognate sequences may form spontaneous hairpin loops, where one arm only needs to be supplemented to achieve the beacon formation. If the target sequence is a rRNA sequence, this, however renders the effector, e.g. the fluorophor, in very close proximity to potentially quenching proteins of the ribosome. In a preferred configuration the stem is extended. In order to conform with said thermodynamic specifications as described herein even with an extended stem a method was devised to keep both the $T_m$ and ΔG within the specifications. According to the present invention, this can be achieved by the introduction of at least one non-matched nucleotide or nucleotide analogue. In the present invention, introduction of at least one non-matched nucleotide may be enhanced by the introduction of an additional nucleotide or nucleotide analogue, so that the two complementary sequences have a different length, and the stem becomes "bended" (see for example position 36 in SEQ ID NO:1), or/and may be achieved by a replacement of a matching nucleotide or nucleotide analogue by a non-matching nucleotide or nucleotide analogue (see for example position 5 in SEQ ID NO: 7). Thus, in the present invention, the "complementary sequences capable of forming a stem" may also include at least one non-matched nucleotide, preferably 1, 2, 3, 4 or 5 non-matched nucleotides.

As can be seen from Table 2 none of the sequences disclosed here could be devised as PNA-beacons due to the said limitations in the construction of PNA-oligonucleotides. The major limitation being in the oligonucleotide length required to have both sufficient specificity and a stem length sufficient to ensure the re-folding of the loop when not hybridised. It is therefore necessary to devise DNA-beacons that are able to hybridise with sufficient affinity and speed to enable the in-situ identification of micro-organisms.

The beacon of the present invention is preferably not a PNA beacon. The backbone of the beacon is preferably a nucleic acid backbone, in particular DNA. The beacon may comprise a nucleic acid analogue such as a deoxyribonucleotide analogue or a ribonucleotide analogue in the nucleic is acid portion or/and in the linker if a linker is present. This analogue is preferably a nucleotide analogue modified at the sugar moiety, the base or/and the phosphate groups. The nucleotide analogue is preferably not a PNA building block.

Following the said 95-percentile in clinical samples, pathogens can be grouped into disease related groups. Probes towards these organisms must work simultaneously under the said conditions, especially if all probes are to be utilised on one chip. The chip application calls for a stringent standardisation of both the cognate and stem characteristics. If a combination of more than one probe is employed, i.e. at least two probes, all probes have to be designed to work on the same slide/chip simultaneously.

The molecular beacon of the combination of the present invention may be selected from the beacons of Table 1, Table 3, and Table 4. The combination of the present invention may comprise one, two, three or even more beacons as described herein, which may be selected from the beacons of Table 1, Table 3 and Table 4. If more than one beacon is present in the combination of the present invention, the beacons may have the same or different cognate sequences. It is preferred that the cognate sequences of individual beacons are different.

If more than one beacon is present in the combination of the present invention, the ΔG difference of the individual beacons of the hybrid of the sequences of (ii) or/and the hybrid of the sequence of (i) with a target sequence may be at the maximum about 4 kcal/mol, preferably at the maximum about 3 kcal/mol, more preferably at the maximum about 2 kcal/mol, and most preferably at the maximum about 1 kcal/mol with respect to the cognate sequence.

The second nucleic acid, the third nucleic acid, and the at least one further nucleic acid may independently contain a label that can be distinguished is from the luminescent group of the at least one first nucleic acid. The second nucleic acid, the third nucleic acid, and the at least one further nucleic acid preferably do not contain luminescent group. The second nucleic acid, the third nucleic acid, and the at least one further nucleic acid preferably do not contain a quencher.

The design of the helper nucleic acid molecules may be performed according to the stringent thermodynamic design as laid out in EP 07 818 883.6 (1) which is included herein by reference. The cognate sequence of the labelled beacon and the helpers may all carry the same thermodynamic characteristics and thus may operate synergistically. The synergy of action due to the precision of design generates the difference in the hybridisation kinetics.

The sequence of a helper nucleic acid capable of hybridising with the target sequence may be designed on the basis of its complementary target sequence (cognate sequence), wherein the sequence of the helper preferably has no mismatch with reference to the target sequence. Having designed a molecular beacon, the skilled person can select cognate sequences for the helper nucleic acids from sequences adjacent to the cognate sequence of the molecular beacon. Suitable sequences may be obtained from public databases. As described herein, preferred molecular beacons may be selected from Table 1, Table 3 and Table 4. In this case, the cognate sequences of the helper nucleic acids may be selected from database sequences of the respective organism adjacent to the cognate sequence of the beacons described in Table 1, Table 3 and Table 4. The cognate sequences of the helper nucleic acids may also be selected from the sequences described in Table 1, Table 3 and Table 4.

The sequences indicated in Table 1, Table 3, and Table 4 as "helper sequences" or "helper" may also be employed for the design of a molecular beacon. In this case, the N-terminal and C-terminal complementary sequences (ii) capable of forming a stem or/and other components described herein have to be added. The sequences indicated in Table 1, Table 3, and Table 4 as "beacon sequences" may also be employed for the design of a helper nucleic acid. In this case, the stem sequences have to be eliminated. For example, Table 4 describes combinations of five nucleic acids of the present inventions, wherein the sequence of one specific nucleic acid is termed "beacon sequence". It is contemplated that any combination of Table 4 is within the scope of the present invention wherein one or more sequences of a combination of Table 4 are selected for design of a molecular beacon, and the remaining sequences are employed as helper sequences. If applicable, stem sequences or/and other components described herein are eliminated or added.

The combinations of hair-pin loops and helper nucleic acids described in Table 4 are preferred. Table 4 describes individual combinations of hair-pin loops and helper nucleic acids, wherein the cognate sequences of the hair-pin loop and the helper sequences are localized on the target sequence of a micro-organism. Specific embodiments of the present invention refer to combinations described in Table 4 comprising a hair-pin loop and one, two, three or four helper nucleic acids. The combinations described in Table 4 can be designated by the name of the hair-pin loop. A preferred combination may be selected from combinations represented by B-Achxyl, B-Acinbaum-IV, B-Acibact-2, B-Baccer-II, B-BacPrev, B-Bcc, B-Ctherm, Citfreu-WIII, B-Clodiff, B-Cloper-II, B-Clospp, Corspp, SB-Corspp, EcoShi, B-EHEC-II, B-Entbac-II, SB-EntSak-I, SB-EntSak-II, Eubiae, Entcoc III, B-Entcoc-II, B-Entalis-2, B-Entium-II, B-*E. coli* III, B-Haeinf, SB-InqLum, Klepne-5, B-Kleboxy-II, SB-Klepne-6, B-Klepne-4, B-Limo-II, SB-Mycavi-A, SB-Mycavi-B, B-Neigon, B-Neimeng, SB-Panapi, SB-PansppA, SB-PansppB, B-propacn, B-propacn, B-Protmir, B-Protvul, SB-Psaer-E, B-Psaer D, SB-RalsppA, SB-RalsppB, SB-RalsppC, Stalug, B-Sal 1686, B-Sermarc-II, B-Shig-II, B-Shig-III, Sb-Shispp-4, B-Staphspp-2, B-Staur- 3, Stalug, B-Stemal-2, B-Straga-3, B-Strepne-2, B-Strepne-3, B-Strpyo-D, B-Strept-III, B-Yers-III, and B-Yers-II. It is more preferred to select a group of combinations from combinations represented by B-Achxyl, B-Acinbaum-IV, B-Acibact-2, B-Baccer-II, B-BacPrev, B-Bcc, B-Ctherm, Citfreu-WIII, B-Clodiff, B-Cloper-II, B-Clospp, Corspp, SB-Corspp, EcoShi, B-EHEC-II, B-Entbac-II, SB-EntSak-I, SB-EntSak-II, Eubiae, Entcoc III, B-Entcoc-II, B-Entalis-2, B-Entium-II, B-*E. coli* III, B-Haeinf, SB-InqLum, Klepne-5, B-Kleboxy-II, SB-Klepne-6, B-Klepne-4, B-Limo-II, SB-Mycavi-A, SB-Mycavi-B, B-Neigon, B-Neimeng, SB-Panapi, SB-PanspprA, SB-PansppB, B-propacn, B-propacn, B-Protmir, B-Protvul, SB-Psaer-E, B-Psaer D, SB-RalsppA, SB-RalsppB, SB-RalsppC, Stalug, B-Sal 1686, B-Sermarc-II, B-Shig-II, B-Shig-III, Sb-Shispp-4, B-Staphspp-2, B-Staur-3, Stalug, B-Stemal-2, B-Straga-3, B-Strepne-2, B-Strepne-3, B-Strpyo-D, B-Strept-III, B-Yers-III, and B-Yers-II. The group may comprise at least 2, at least 5, at least 10, at least 15, at least 20, at least 30, at least 40, at least 50, at least 60, or even all of the combinations described in Table 4. The group may comprise at the maximum 60, at the maximum 50, at the maximum 40 at the maximum 30 at the maximum 20, at the maximum 10, or at the maximum 5 of the combinations described in Table 4. It is so contemplated that specific embodiments of the present invention refer to groups having the minimum number or/and the maximum number of combinations as indicated herein, wherein any combination may be selected from Table 4. For example, specific embodiments of the present invention refer to groups comprising two, three, four, five, six, seven, eight, nine, or ten combinations selected from Table 4.

Preferred groups of combinations of the present invention refer to diagnostic groups. Preferred groups of combinations are selected from combinations suitable for identifying organisms in blood culture (BC) of Gram negative organisms, as for instance indicated in Table 4. Other preferred groups of combinations are selected from combinations suitable for identifying organisms in blood culture of Gram positive organisms, as for instance indicated in Table 4. Other preferred groups of combinations are selected from combinations suitable for identifying organisms capable of causing pneumonia, as for instance indicated in Table 4. Other preferred groups of combinations are selected from combinations suitable for identifying organisms associated with cystic fibrosis, as for instance indicated in Table 4. Other preferred groups of combinations are selected from combinations suitable for identifying organisms found in stool, as for instance indicated in Table 4.

It is contemplated that a combination selected from Table 4 may be a combination wherein one or more sequences of the combination are selected for design of a hair-pin loop, and the remaining sequences are employed as helper sequences, as described herein. In other words, not only the sequence indicated in Table 4 as probe sequence (complementary to the target sequence), but also a sequence indicated in Table 4 as helper sequence may be employed for the design of a hairpin loop.

The helper nucleic acid of the present invention is preferably not a PNA. The backbone of the helper is preferably a nucleic acid backbone, in particular DNA. The helper nucleic acid may comprise a nucleic acid analogue such as a deoxyribonucleotide analogue or a ribonucleotide analogue in the nucleic acid portion or/and in the linker if a linker is present. This analogue is preferably a nucleotide analogue modified at the sugar moiety, the base or/and the phosphate groups. The nucleotide analogue is preferably not a PNA building block.

The second nucleic acid, the third nucleic acid, and the at least one further nucleic acid preferably do not contain a mismatch in the sequence capable of hybridising with the target sequence. The second nucleic acid, the third nucleic acid, and the at least one further nucleic acid may independently comprise at least one nucleotide which does not hybridise with the target sequence, preferably independently located at the 3' or/and the 5' terminus of the nucleic acid molecule.

The nucleic acids of the combination according to the present invention are in particular suitable for in situ hybridisation, more particular for FISH. The hybridisation may take place within the cell as described herein, in particular within a micro-organism as described herein. The nucleic acids of the combination may be designed for hybridisation under stringent hybridisation conditions.

Stringent hybridisation conditions, as used herein, preferably comprises hybridisation at 52° C. (±0.2° C.) for up to 30 min, up to 20 min, up to 15 min or up to 10 min, preferably for about 10 minutes, under high salt and preferably under conditions essentially free of divalent cations, in particular under essentially $Mg^{2+}$ free conditions (e.g. 900 mM NaCl, 20 mM Tris/HCl pH 8.3, 0.01% w/w SDS, 1 mM EDTA, 20% v/v formamide), and washing in essentially ethanolic, low salt and room temperature for about 30 to about 90 seconds or about 45 to about 75 seconds, preferably about 60 seconds. Preferably, washing is performed under high $Mg^{2+}$ conditions, for instance in 50% ethanol, 215 mM NaCl, 5 mM $MgCl_2$, 50 mM Tris/HCl pH 8.3.

In the present invention, hybridisation may be performed in the presence of SDS, for instance about 0.005% w/w to 0.015% w/w or about 0.01% w/w SDS. Hybridisation may also be performed in the presence of formamide, for instance about 15% v/v to about 25% v/v formamide, preferably about 20% v/v formamide. During hybridisation, an agent capable of complexing divalent cations, such as EDTA, may be present in a concentration of about 0.2 mM to about 2 mM, or about 0.5 mM to about 1.5 mM. Preferred is an EDTA concentration of about 1 mM.

Room temperature, as used herein, preferably refers to a temperature in the range of about 18° C. to about 24° C. or about 19° C. to about 22° C., such as about 18° C., about 19° C., about 20° C., about 21° C., about 22° C., about 23° C., or about 24° C.

“Essentially ethanolic conditions” as used herein, preferably refer to an ethanol concentration of 0 to 90% v/v, 40 to 90% v/v, 50 to 90% v/v, 60 to 90% v/v, for instance in the range of 40 to 60% v/v, preferably about 50% v/v.

During hybridisation or/and washing, pH may be independently be adjusted to >8, about 7.5 to about 9, or about 8 to about 8.5, preferably to about 8.3.

As used herein, low salt conditions include a total salt concentration of about 50 mM to about 400 mM, about 100 mM to about 300 mM, or about 150 to about 250 mM. Preferred is a concentration of about 200 mM, such as 215 mM. High salt, as used herein, includes a total salt concentration of about 700 mM to about 1100 mM, about 800 mM to about 1000 mM, or about 850 mM to 950 mM. Preferred is a concentration of about 900 mM, such as 915 mM. “Total salt concentration”, as used herein means the concentration of salts of monovalent cations.

It is preferred that in the combination of the present invention the individual nucleic acids function uniformly. “Functioning uniformly” means that successful hybridisation can be achieved with different nucleic acids probes of the present invention under the same hybridisation conditions, for instance under standardised hybridisation conditions. In other words, uniformly functioning nucleic acids of the present invention do not require individual optimisation of the hybridisation conditions.

The combination of nucleic acid molecules as described herein may be provided in one or more compositions, optionally together with the required hybridisation reagents. It is preferred that the combination is provided in one composition.

In the nucleic acids of the combination of the present invention, the ΔG values of individual nucleic acids with respect to its respective cognate sequence may differ at the maximum by about 10 kcal/mol, preferably at the maximum of about 6 kcal/mol, more preferably at the maximum of about 3 kcal/mol. In particular, if more than one beacon is present in the combination of the present invention, the ΔG values of individual beacon stems with respect to its respective cognate sequence may differ about 8 kcal/mol, preferably at the maximum by about 5 kcal/mol, more preferably at the is maximum of about 3 kcal/mol.

The nucleic acid molecules of the combination of the present invention may independently be oligonucleotides. The sequences of the nucleic acid molecules capable of hybridising with the target sequence independently may have a length in the range of 16 to 26 nucleotides, in particular about 20 nucleotides. For instance, at least one sequence of the nucleic acid molecules hybridising with the target sequence may have a length in the range of 16 to 26 nucleotides, in particular about 20 nucleotides.

The art teaches that helper sequences should be applied in large surplus concentrations. Surprisingly it was found that the working concentration of the helpers and beacons required in the said configuration may be essentially equimolar. Moreover, this design removed the restrictions due to the inaccessibility of rRNA regions and allowed a free choice of unique sequences. Surprisingly, it was possible to generate a uniform 100% signal after only 8 minutes irrespective of the position beacons were hybridising towards. The nucleic acid molecules of the combination may provided in a composition in essentially equimolar concentrations. In the present invention, “essentially equimolar concentrations” means that the concentrations of at least two nucleic acid molecules in the composition may differ by 15 percent by weight at the maximum, 10 percent by weight at the maximum, or 5 percent by weight at the maximum.

Yet another aspect of the present invention is a kit or chip comprising a combination of nucleic acid molecules as described herein, optionally together with the required hybridisation reagents. Preferably, the chip or kit contains one or more combinations of nucleic acid molecules as described herein in separate compositions, for instance one, two, three, four, five, six, seven, eight, nine, ten or even more combinations. Eight separate combinations in a kit or on a chip are preferred. List of groupings and resulting kits for the detection, enumeration and identification of the listed organisms is compiled in Table 1.

A further aspect of the invention is that utilizing combinations according to this invention, active expression products of genes may be detected on mRNA-level, for example by aligning more than one of hair-pin loop pairs along a specific sequence without prior amplification. Highly expressed sequences of genes coding for antibiotic resistance, toxin production or indeed oncogenes may be detected with the same speed and specificity as in the identification of micro-organisms.

The combination, kit or/and chip of the present invention may be used for the identification of a cell as described herein, in particular of a micro-organism as described herein. The combination or/and kit of the present invention preferably is for diagnostic use. More preferably, the combination of the present invention is for diagnosis of the presence of a cell as described herein, in particular of a micro-organism as described herein.

The combination or/and kit of the present invention may be used for the determination of antibiotic resistance.

The combination or/and kit of the present invention may be used for the determination of toxin production, for instance of a cell or/and micro-organism as described herein.

The combination or/and kit of the present invention may be used for the determination of oncogene expression, for instance in a cell or/and micro-organism as described herein.

The combination, kit or/and chip of the present invention may be used for the manufacture of a pharmaceutical composition of the diagnosis of the presence of a cell as described herein, in particular of a micro-organism as described herein.

The combination, kit or/and chip of the present invention may be used for the manufacture of a pharmaceutical composition for the diagnosis of pathological characters within a cell as described herein.

The combination can be applied to assays designed to be performed in tubes, microtitre plates, filtered microtitre wells, slides and chips. The detection can be made with fluorescence, time resolved fluorescence, with a plurality of fluorophores.

In the preferred embodiment for FISH the assay is performed on glass slides designed to hold and separate several samples.

Yet another aspect of the present invention is a method of identifying a cell in a sample, comprising the steps (a) providing a sample, (b) contacting the sample of (a) with the combination of nucleic acid molecules according to the present invention under conditions allowing hybridisation of the oligonucleotides with the target sequences in the cell, and (c) determining the luminescence of the luminescent group of the first nucleic acid molecule.

wherein the luminescence of the first oligonucleotide indicates the presence of the target sequence.

The presence of the target sequence indicates the presence of the cell or/and a group of cells, in particular if the target sequence is specific for the cell or/and the group of cells.

The cell may be a cell as described herein, for instance a prokaryotic or a eukaryotic cell. In particular, the cell may be a micro-organism as described herein.

The sample may be any sample of biological origin, such as a clinical or food sample, suspected of comprising a nucleic acid to be detected by the hair-pin loop. The sample may be a sample comprising a cell, in particular a micro-organism, such as a bacterium, yeast or/and a mold, in particular a Gram positive or/and a Gram negative bacterium. The general procedure for the assay is identical with a minor deviation in the pre-treatment of Gram negative and Gram positive organisms (see for instance Example 3).

In the method of the present invention step (b) and (c) may be performed in situ, in particular by FISH.

In step (b), the sample may be fixed on a surface. Step (b) may comprise stringent hybridisation conditions, as described herein.

In step (b), contacting the sample of (a) with the combination of nucleic acid molecules may be performed for up to about 30 min, for up to about 20 min, for up to about 15 min, or for up to about 10 min.

The hybridisation buffer employed in step (b) preferably contains essentially no divalent cations, in particular, the hybridisation buffer employed in step (b) preferably is essentially free of magnesium.

In step (b), the nucleic acids of the combination may be applied in essentially equimolar concentrations.

Step (b) of the method of the present invention may comprise (1) contacting at least one nucleic acid of any of the present invention or a combination of nucleic acids of the present invention with the biological sample, (2) hybridising the nucleic acid or the combination of nucleic acids of (1) with the sample under conditions where the stem will open in the presence of a cognate sequence, e.g. hybridising with a buffer which is essentially free of divalent cations, in particular essentially free of $Mg^{2+}$ and (3) hybridising the nucleic acid or the combination of nucleic acid of (1) with the sample under conditions where the stem of the nucleic is open, e.g. hybridising with a buffer which is essentially free of divalent cations, in particular essentially free of $Mg^{2+}$, and (4) inducing conditions which allow for stem formation in those nucleic acid molecules of (1) not forming a hybrid with the sample, e.g. washing with a magnesium containing buffer, for instance at pH>8 or/and at room temperature.

Any hybridisation protocol comprising application of an essentially $Mg^{2+}$ free solution and a $Mg^{2+}$ containing solution as indicated above may be applied. "Essentially free of divalent cations" refers to divalent cations in a concentration of less than 1 mM, preferably less than 0.1 mM, more preferably less than 0.05 mM, most preferably less than 0.01 mM. "Essentially free of $Mg^{2+}$" refers to a $Mg^{2+}$ concentration of less than 1 mM, preferably less than 0.1 mM, more preferably less than 0.05 mM, most preferably less than 0.01 mM. In addition, the removal of divalent ions may be ensured by the addition of a complexing agent, such as EDTA, present in a concentration of about 0.2 mM to 2 mM, or 0.5 mM to 1.5 mM. Preferred is an EDTA concentration of about 1 mM.

The magnesium containing buffer employed in step (b) may contain about 0.1 mM to about 20 mM $Mg^{2+}$, about 1 mM to about 20 mM $Mg^{2+}$, about 1 mM to about 10 mM $Mg^{2+}$, about 2.5 mM to about 7.5 mM $Mg^{2+}$. Preferred is a concentration of about 5 mM $Mg^{2+}$.

At the end of the hybridisation all non-bound beacons need to be returned and secured in the hair-pin loop formation. According to the thermodynamic parameters the refolding should take place spontaneously at room temperature. It was found that this could only be ensured in the presence of bi-valent metal ions. Moreover, the specificity of the assay depended upon the concentration of mono-valent salt in the stop-buffer.

Thus the refolding can be achieved by briefly dipping the slide first into an is ethanol bath and then into a stop-buffer bath containing mono-valent salt to support dissociation of weakly bound beacons and divalent salts that support hair-pin loop formation and at a temperature that favours the hair-pin loop formation. In a preferred configuration the ethanol and salt baths are combined and may contain 0-90% v/v ethanol, 10 mM to 1M mono-valent salt, 0.1-20 mM bi-valent salt and buffered between pH 7 and pH 9. In the most preferred configuration the stop-buffer contains 50% v/v ethanol, 215 mM NaCl, 5 mM $MgCl_2$ and 20 mM Tris/HCl pH 8.3.

For instance, the following protocol may be used: Aliquots of clinical samples are applied to defined fields on the slides. Preferably a defined quantity of 10 μl is applied and dried.

1. The samples are the heat fixed to the slides.
2. Gram positive organisms are subjected to a Lysozyme/Lysostaphin digestion following well published specifications. In a preferred embodiment the digestion is run for 2 to 7 minutes at between 28 and 60° C. in a humidified chamber. The most preferred digestion is performed by adding digesting enzymes onto each required field of the slide, directly while being on the (52° C.) hotplate and left until dryness.
3. Pores are then formed for instance by immersing the slide in pure methanol or pure (at least 96%) ethanol for several minutes. In a preferred embodiment the methanol or ethanol is ice cold and the immersion time is between 2 and 10 minutes. In a more preferred embodiment the slides are immersed for 4 to 6 minutes in ethanol. In the most preferred embodiment the slides are immersed in 96% industrial methylated spirits (IMS) ethanol (or equivalently denatured ethanol) for 5 minutes at room temperature.
4. The slide is the dried on a hot-plate, for instance at 52° C.
5. The nucleic acids (one or more beacons, at least two helpers) are dissolved in a hybridisation buffer (which may be essentially free of $Mg^{2+}$) and then applied to each field of the slide while on the slide warmer.
6. The slide is placed in a hybridisation chamber, humidified with hybridisation buffer. In a preferred embodiment the slide is covered with a hydrophobic cover slip and placed on a covered slide warmer at 52° C. for about 10 minutes.
7. The slide is then washed with a magnesium containing buffer, for instance at pH>8 or/and at room temperature. The buffer main contain about 0.1 to about 20 mM $Mg^{2+}$, in particular about 1 to about 10 mM $Mg^{2+}$, more particular about 2.5 to 7.5 mM$Mg^{2+}$, even more particular about 5 mM $Mg^{2+}$.
8. The slide is then dried and may be mounted with mounting fluid and can be read under an epifluorescence microscope at a total magnification of for instance 400×, 600×, or 1000×.

Should other vessels be used for the hybridisation, the detection may be via flow-cytometry or automated fluorescence reader well known in the art.

Also employed in the method of the present invention can be a kit or chip as described herein.

Yet another embodiment of the present invention relates to chip applications of the beacons of the present invention. For chip applications the beacons need to be covalently attached to a carrier surface. To facilitate this, the 3'-terminal base of the designed beacons may be either biotinylated or linked via a hetero-bifunctional reagent to an enzyme using methods well known in the art of protein and nucleic acid chemistry. Biotinylated beacons may then be added to Streptavidin coated chips as can be obtained freely from commercial sources (19). In this application the respective biotinylated hairpin loops can be attached to plurality of distinct fields of one chip, for instance at least 10, at least 50, at least 100, at least 200, or at least 500 fields, or at the maximum 500, at the maximum 400 or at the maximum 300 ro fields, Total RNA can be extracted from samples using commercially available kits (20) and can be applied to the chip under hybridising conditions as described herein. After hybridisation the chip can be briefly washed with a magnesium containing buffer, as described herein, for instance at pH>8. Fluorescence on a field marks the presence of specific is target sequence, for instance a specific RNA indicating the presence of a respective organism in the sample.

In order to open hybridisation assays to large scale routine applications it is necessary to analyse a plurality of samples sequentially on one reusable chip. The design of the chip must allow large scale production, efficient quality control and long shelf live.

To perform such an assay a large plurality of sequences with identical characteristics (e.g. Table 1, Table 3 or/and Table 4) have been developed, which may be applied to defined positions on the detecting device (chip) respectively.

In a typical assay, total RNA is extracted from a sample utilising extraction procedure and kits readily available on the market and placed on the chip under said hybridisation conditions. After the hybridisation the chip is washed with said stop buffer at room temperature, and is read as is well known in the art. At the end of the cycle all hybridised RNA is washed off with DNA and RNA free hybridisation buffer at about 62° C. The temperature is then dropped to about 52° C. to equilibrate for the next hybridisation cycle.

The invention is further illustrated by the following examples and figures.

Legends

Table 1 describes beacon sequences of the present invention. Abbreviations: R&G: a red or/and a green fluorescent dye may be attached to the beacon, such as Cy3 or FITC or a derivative thereof.

Table 2 describes that PNA beacons are not suitable in the present invention. Calculations were performed with the sequences of Table 1 assuming the beacon to be a PNA beacon. In contrast to DNA beacons, all of the following five criteria have to be fulfilled: GC content <60%, <3 bases selfcomplementary, 4 purines in a row, length of maximal 18, inverse sequence palindromes or repeats or hairpins. "Yes" ("No") in Table 2 indicates that the criterion is fulfilled (not fulfilled). The column "Final" indicates if a PNA beacon is suitable in the present invention ("Yes") or not ("No"). "No" in final indicates that one of the five criteria is not met. "Yes" would indicate that all criteria are met. All sequences of Table 2 are judged to be "No". Thus, no one of the sequences of Table 1 would be suitable in a PNA beacon.

Table 3: List of beacon probes that work under identical conditions as in Table 1 and possess very similar physicochemical conditions.

Table 4: Individual combinations of hair-pin loops and helper nucleic acids, wherein the cognate sequences of the beacon and the helper sequences are localized on the target sequence of a micro-organism ("target organism"). In the hair-pin loop sequence, the sequence complementary to the cognate sequence is underlined. "rRNA" refers to localisation of the target sequence in 16S or 23S rRNA, if applicable. "Alignment with *E. coli*" refers to the position of the corresponding sequence in *E. coli* 16S or 23S RNA, respectively. "Fuchs score" refers to the score (brightness class) defined in Fuchs et al. (4). The columns "active beacons in kits" indicate preferred groups of combinations. Preferred groups of combinations refer to groups of combinations suitable for identifying organisms in blood culture (BC) of Gram negative organisms, organisms in blood culture of Gram positive organisms, organisms causing pneumonia, organisms associated with cystic fibrosis, and organisms found in stool. Members of these "diagnostic groups" are indicated by "1" in the respective columns.

FIG. 1: Comparison of hybridisation data derived from U.S. Pat. No. 5,030,557 ("conventional probe") and hybridisation data of the present invention. The data of Tables I, IIa, IIb, and IIc of U.S. Pat. No. 5,030,557 have been averaged. (1) Probe alone according to U.S. Pat. No. 5,030,557. (2) Probe and one helper according to U.S. Pat. No. 5,030,557. (3) Probe and two helpers according to U.S. Pat. No. 5,030,557. (4) Probe and three helpers according to U.S. Pat. No. 5,030,557. (5) Probe (molecular beacon) and four helper nucleic acids according to the present invention. "12 min" and "overnight" indicate hybridisation periods. "Overnight % improvement" indicates the % improvement by hybridisation of overnight incubation compared with 12 min hybridisation. "% hybridisation" indicates the percentage of hybridisation sites in a sample which are occupied by a hybridisation probe.

Figure 2:
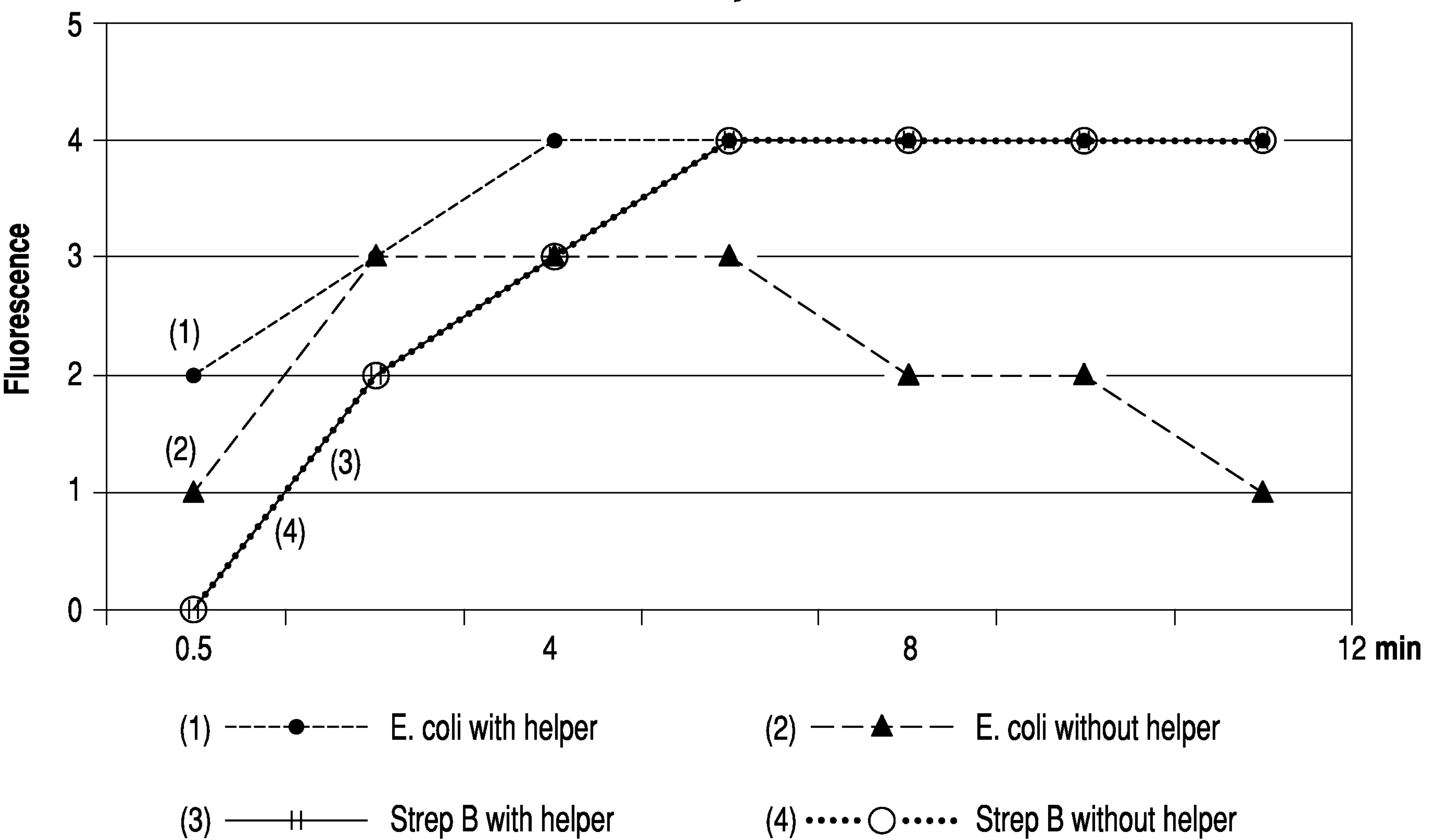

FIG. 2: Kinetics of hybridisation. (1) *E. coli* molecular beacon with helper, (2) *E. coli* without helper, (3) B-Straga-3 molecular beacon (see Table 4) with helper, (4) B-Straga-3 without helper. Fluorescence is given in relative units.

FIG. 3: Scheme describing the alignment of a molecular beacon and four helper oligonucleotides to a rRNA sequence.

Example 1. Effect of Helpers

Comparison of the effects of state of the art FIG. 1 summarizes the effect of helper oligonucleotides upon probe hybridisation, as described in U.S. Pat. No. 5,030,557 (see bars (1) to (4) in FIG. 1). The data have been obtained from Tables I, IIa, IIb and IIc of U.S. Pat. No. 5,030,557. Averages have been calculated.

U.S. Pat. No. 5,030,557 teach the use of helper oligonucleotides to enhance the binding of labelled oligonucleotides to isolated ribosomal RNA. Linear probes of 18 to 24 nucleotides in length have been employed. Helpers had a length from 23 to 58 nucleotides. However, this required an overnight incubation to achieve an enhanced signal. In addition, U.S. Pat. No. 5,030,557 call for a 50-200 fold higher concentration of each helper to achieve the improvement. Adding a second helper increased the signal by 20% and the further addition of a third helper only increased the signal by a further 7% (see "overnight" bars in FIG. 1).

In in-situ hybridisation in a micro-organism with a combination of a molecular beacon and four helper nucleic acids according to the present invention, hybridisation reaches about 100% after 12 min (see bars (5) in FIG. 1). Taking into account that in-situ hybridisation generally needs longer hybridisation periods than hybridisation taking place in solution, a hybridisation period of only 12 min with a combination of the present invention compared with overnight hybridisation as described in U.S. Pat. No. 5,030,557 is a strong improvement with respect to state of the art combinations of probes and helpers.

Example 2. Kinetics of In-Situ Hybridisation

Molecular beacons of the present invention (*E. coli* molecular beacon, B-Straga-3, see Table 4) are tested in the absence and presence of four helper nucleic acids in in-situ hybridisation with *E. coli* and *Streptococcus*, respectively, fixated on a slide. The beacon B-Straga-3 comprises a sequence hybridising with a target sequence located in 16S rRNA of *Streptococcus agalactiae*.

10 μl aliquots of a respective bacterial suspension were placed onto each field of a slide and dried to render $10^5$ cells per field. The further in-situ hybridisation assay was performed as described in the invention with one exception. Field 1 received the hybridisation mix at time=0; field 2 after 2 min.; field 3 after 4 min.; field 4 after 6 min.; field 5 after 8 min.; field 6 after 10 min.; field 7 after 11.5 min.; and field 8 before dipping into the stop solution.

As can be seen in FIG. 2, the hybridisation of an unaided *E. coli* beacon is weak and thus reversible and the re-annealing of rRNA is preferred over the hybridisation with the beacon. The speed of hybridisation as shown in FIG. 2 is due to the stringent design of beacons together with respective helpers.

Example 3

A typical hybridisation procedure for the assay is identical for all beacons with a minor deviation in the pre-treatment of Gram negative and Gram positive organisms, as indicated in the Table below.

| Step | Gram negative applications | Gram positive applications |
|---|---|---|
| 1 | Apply 10 μl sample to each designated field of a slide | Apply 10 μl sample to each designated field of a slide |
| 2 | Dry on hot plate 52° C. | Dry on hot plate 52° C. |
| 3 | | On the hot plate add 10 μl lysis-mix (3.4) and dry (takes 4 min) |
| 4 | In a coplin jar, immerse the slide in IMS for 7 min. and dry on hot plate 52° C. | In a coplin jar, immerse the slide in IMS for 3 min. and dry on hot plate 52° C. |
| 5 | Remove from hot plate and add 10 μl ready to use hybridization mix to each field | |
| 6 | Place the hybridization cover over the slide and incubate at 52° C. in an oven (2.5) for 10 minutes | |
| 7 | In a coplin jar, immerse the slide in Stop-Mix (3.2) for 1 min. | |
| 8 | Briefly dip in IMS and dry on hot plate 52° C. | |
| 9 | Immediately place a small drop of mounting media on each field and cover with cover slip | |
| 10 | Read with fluorescence microscope | |

The reading can be performed visually or with the aid of automated reading devices with a fluorescence microscope. As is well known in the art, in-situ hybridisation can be easily adapted to flow cytometry by performing the said steps in a micro titre plate and reading via a flow-cytometer. The obvious advantage lies in the ease of automation.

REFERENCES (1) EP 07 818 883.6

(2) M. S. Shchepinov, S. C. Case-Green and E. M. Southern, Appl Environ Microbiol. 2007 January; 73(1): 73-82. Steric factors influencing hybridisation of nucleic acids to oligonucleotide arrays (3) Michael M. A. Sekar, Will Bloch and Pamela M. St John, Nucleic Acids Research 2005 33(1):366-375; Comparative study of sequence-dependent hybridization kinetics in solution and on microspheres (4) BERNHARD M. FUCHS, KAZUAKI SYUTSUBO, WOLFGANG LUDWIG, AND RUDOLF AMANN, APPLIED AND ENVIRONMENTAL MICROBIOLOGY, AEM. 67.2.961-968.2001, In Situ Accessibility of *Escherichia coli* 23S rRNA to Fluorescently Labeled Oligonucleotide Probes (5) BERNHARD MAXIMILIAN FUCHS, GÜNTER WALLNER, WOLFGANG BEISKER, INES SCHWIPPL, WOLFGANG LUDWIG, AND RUDOLF AMANN1, APPLIED AND ENVIRONMENTAL MICROBIOLOGY, December 1998, p. 4973-4982 Flow Cytometric Analysis of the In Situ Accessibility of *Escherichia coli* 16S rRNA for Fluorescently Labeled Oligonucleotide Probes (6) BERNHARD M. FUCHS, FRANK OLIVER GLÖCKNER, JÖRG WULF, AND RUDOLF AMANN, APPLIED AND ENVIRONMENTAL MICROBIOLOGY, August 2000, p. 3603-3607, Unlabeled Helper Oligonucleotides Increase the In Situ Accessibility to 16S rRNA of Fluorescently Labeled Oligonucleotide Probes (7) RUDOLF I. AMANN, WOLFGANG LUDWIG, AND KARL-HEINZ SCHLEIFER, MICROBIOLOGICAL REVIEWS, March 1995, p. 143-169, Phylogenetic Identification and In Situ Detection of Individual, Microbial Cells without Cultivation (8) U.S. Pat. No. 5,030,557: Means and Methods for enhancing nucleic acid hybridisation. Inventors: Hogan JJ and Milliman CL.

(9) WO 1992014841 19920903, NOVEL LANTHANIDE CHELATE-CONJUGATED OLIGONUCLEOTIDES.

Subject of the present invention are also the following embodiments:

Item 1. A combination of nucleic acid molecules capable of hybridising with a target nucleic acid sequence, wherein the combination comprises (a) at least one first nucleic acid molecule comprising (i) a sequence capable of hybridising with the target sequence, (ii) two complementary sequences capable of forming a stem, and (iii) a luminescent group and a quencher group, wherein the quencher group quenches the fluorescent group if the nucleic acid forms a stem-loop structure, and wherein the fluorescent group is capable of emitting a luminescence signal upon excitation if the oligonucleotide is hybridised with the target sequence, (b) a second nucleic acid molecule, a third nucleic acid molecule, and optionally at least one further nucleic acid molecule, wherein the second nucleic acid molecule, the third nucleic acid molecule, and the optional at least one further nucleic acid molecule hybridise with the target sequence at a sequence located 5' or/and 3' from the sequence to which the first nucleic acid hybridises.

Item 2. The combination according to item 1, wherein the sequences to which the at least one first, the second, the third and the optional at least one further nucleic acid molecules hybridise are non-overlapping sequences of the target sequence.

Item 3. The combination according to item 1 or 2, wherein the nucleic acids are suitable for in situ hybridisation, in particular for FISH.

Item 4. The combination according to any of the items 1 to 3, wherein the hybridisation takes place within a cell.

Item 5. The combination according to any of the preceding items, wherein the target nucleic acid sequence is selected from DNA sequences and RNA sequences.

Item 6. The combination according to item 5, wherein the target nucleic acid sequence is a rRNA sequence.

Item 7. The combination according to item 5, wherein the target nucleic sequence is a mRNA sequence.

Item 8. The combination according to any of the preceding items, wherein the luminescent group is independently attached at the 5' end or the 3' end of the first nucleic acid, and the quencher is attached at the other end not covered by the luminescent group Item 9. The combination according to any of the preceding items, wherein the first nucleic acid molecule comprises a sequence capable of forming a hair-pin loop, e.g. a molecular beacon.

Item 10. The combination according to any of the items 1 to 8, wherein the nucleic acid molecules hybridise with the target sequence at locations directly adjacent to each other.

Item 11. The combination according to any of the items 1 to 8, wherein at least two nucleic acid molecules hybridise with the target sequence at locations separated from each other by a gap of at least one nucleotide.

Item 12. The combination according to any of the preceding items, wherein at least one sequence of the nucleic acid molecules hybridising with the target sequence has a length in the range of 16 to 26 nucleotides.

Item 13. The combination according to any of the preceding items, wherein the nucleic acid molecules of the combination are provided in a composition in essentially equimolar concentrations.

Item 14. The combination according to any of the preceding items, wherein the nucleic acid molecules of the combination independently hybridise with the target sequence with a ΔG in the range of −15 to −25 kcal/mol.

Item 15. The combination according to any of the preceding items, wherein the nucleic acids of the combination independently hybridise with the target sequence with a combined ΔG in the range of −60 to −150 kcal/mol, −80 to −150 kcal/mol, or −100 to −120 kcal/mol.

Item 16. The combination according to any of the preceding items, wherein the nucleic acids of the combination independently hybridise with the target sequence with a more negative ΔG than the ΔG generated by the natural refolding of the target sequence.

Item 17. The combination according to any of the preceding items for diagnostic use.

Item 18. The combination according to any of the preceding items for diagnosis of the presence of a cell.

Item 19. The combination according to any of the preceding items for the determination of antibiotic resistance.

Item 20. The combination according to any of the preceding items for the determination of toxin production.

Item 21. The combination according to any of the preceding items for the determination of oncogene expression.

Item 22. Kit or chip comprising the combination of any of the preceding items.

Item 23. A method of identifying a cell in a sample, comprising the steps (a) providing a sample, (b) contacting the sample of (a) with the combination of nucleic acid molecules of any of the items 1 to 16 under conditions allowing hybridisation of the oligonucleotides with the target sequences in the cell, and (c) determining the luminescence of the luminescent group of the first nucleic acid molecule.

wherein the fluorescence of the first oligonucleotide indicates the presence of the target sequence.

Item 24. The method according to item 23, wherein the sample is selected from biological samples, in particular clinical samples.

Item 25. The method according to item 23 or 24, wherein step (b) and (c) are performed in situ, in particular by FISH.

Item 26. The method according to any of the items 23 to 25, wherein in step (b), the sample is fixated on a surface.

Item 27. The method according to any of the items 23 to 26, wherein step (b) comprises stringent hybridisation conditions.

Item 28. The method according to any of the items 23 to 27, wherein contacting the sample of (a) with the combination of nucleic acid molecules is performed for up to about 30 min.

Item 29. The method according to any of the items 23 to 28, wherein the hybridisation buffer employed in step (b) does not contain divalent cations.

Item 30. Use of a combination of any of the items 1 to 21 or a kit or chip of item 22 for the identification of a cell.

Item 31. Use of a combination of any of the items 1 to 21 or a kit or chip of item 22 for the manufacture of a pharmaceutical composition for the diagnosis of the presence of a cell.

The invention claimed is:

1. A combination of nucleic acid molecules capable of hybridizing with a target nucleic acid sequence of a microorganism, wherein the combination comprises:

a) a molecular beacon (first nucleic acid molecule) capable of forming a hair-pin loop comprising
   (i) a probe sequence capable of hybridizing with a cognate sequence of the target nucleic acid sequence, wherein the cognate sequence is 16-26 nucleotides long,
   (ii) two complementary sequences flanking the probe sequence and capable of forming a stem of the molecular beacon, wherein each of the two complementary sequences has a length of 4 to 10 nucleotides, and
   (iii) a luminescent group and a quencher group each being independently attached to one of the two complementary sequences, wherein the quencher group quenches the luminescent group if the first nucleic acid molecule forms the hair-pin loop, and wherein the luminescent group emits a luminescence signal upon excitation if the probe is hybridized with the target nucleic acid sequence, b) a second nucleic acid molecule and a third nucleic acid molecule, wherein the second nucleic acid molecule and the third nucleic acid molecule comprise sequences that hybridize, under identical hybridization conditions, with the target nucleic acid sequence 5' or/and 3' of the cognate sequence, and wherein, the first nucleic acid molecule, the second nucleic acid molecule, and the third nucleic acid molecule each comprise sequences that individually hybridize, under the identical hybridization conditions, to the target nucleic acid sequence with a ΔG (Gibbs energy) value of −15 to −25 kcal/mol, with their respective ΔG values not differing from one another more than 3 kcal/mol.

2. The combination according to claim 1, wherein the first, second and third nucleic acids molecule are adapted for in situ hybridization.

3. The combination according to claim 2, wherein said in-situ hybridization in a) and/or b) is fluorescence in-situ hybridization (FISH).

4. The combination according to claim 1, wherein the target nucleic acid sequence is a DNA sequence or a RNA sequence of the microorganism.

5. The combination according to claim 4, wherein the RNA sequence is a rRNA sequence of the microorganism.

6. The combination according to claim 1, wherein the first, second and third nucleic acid molecules hybridize within the target nucleic acid sequence at locations directly adjacent to each other.

7. The combination according to claim 1, wherein the target nucleic acid sequence is a nucleic acid sequence selected from a target microorganism listed in Table 1 or Table 4.

8. The combination according to claim 1, wherein the ΔG values of the first nucleic acid molecule, the second nucleic acid molecule, and the third nucleic acid molecule do not differ from one another more than 2 kcal/mol or not more than 1 kcal/mol.

9. A kit or chip for diagnosing presence of a microorganism comprising the combination of claim 1, wherein in the kit, the combination is in one container and instruction of how to use the combination is in another container, or wherein the combination is on the chip.

10. The combination of claim 1, wherein the combination is contained in a pharmaceutical composition for diagnosing a presence of the microorganism.

11. The combination of nucleic acid molecules according to claim 1, wherein the sequence in (a) (i) hybridizes with the target sequence, the two complimentary sequences in (a) (ii) form a stem and the luminescent group in (a) (iii) emits the luminescence signal upon excitation if the oligonucleotide is hybridized with the target sequence.

12. the combination of claim 1, wherein the combination comprises in (b) a fourth and a fifth nucleic acid molecule which are oligonucleotides having a length of 16-26 nucleotides which each hybridizes, under the identical hybridization conditions, with the target sequence 5' or/and 3' of where the first nucleic acid hybridizes.

13. The combination of claim 12, wherein up to 8 further nucleic acid molecules are provided.

14. The combination of claim 1, wherein the target nucleic acid sequence codes for gene(s) involved in antibiotic resistance and/or toxin production.

15. The combination of claim 1, wherein the target nucleic acid sequence is a species-specific sequence of the microorganism.

16. The combination of claim 15, wherein the target nucleic acid sequence is a rRNA sequence.

17. The combination of claim 1, wherein the target nucleic acid sequence is fixated to a solid-phase support.

18. The combination of claim 1, wherein the second and third nucleic acid molecule are oligonucleotides having a length of 16-26 nucleotides.

19. The combination according to claim 1, wherein two of the first, second and third nucleic acid molecule hybridize with the target nucleic acid sequence at locations separated from each other within the target nucleic acid sequence.

20. A method of identifying a cell, diagnosing the presence of a cell and/or a target sequence in a cell in a sample, comprising
   (a) providing a sample,
   (b) contacting the sample of (a) with the combination of nucleic acid molecules of claim 1 under conditions allowing hybridization of the oligonucleotides with the target sequences in the cell, and
   (c) determining the luminescence of the luminescent group of the first nucleic acid molecule,
   wherein the fluorescence of the first oligonucleotide indicates the presence of the target sequence.

21. The method according to claim 20, wherein the sample is selected from biological samples including clinical samples.

22. The method according to claim 20, wherein (b) and (c) are performed in situ.

23. The method according to claim 22, wherein (b) and (c) are performed by fluorescence in-situ hybridization (FISH).

24. The method according to claim 20, wherein the hybridization buffer employed in step (b) does not contain divalent cations.

25. The method of claim 20, wherein in (b) the composition provided is part of a kit or is on a chip.

26. The method of claim 20, wherein said target sequence is associated with antibiotic resistance, toxin production, or/and oncogene expression.

* * * * *

SEQUENCE LISTING

```
<160> NUMBER OF SEQ ID NOS: 825

<210> SEQ ID NO 1
<211> LENGTH: 40
<212> TYPE: DNA
<213> ORGANISM: Acinetobacter

<400> SEQUENCE: 1

tgccggatta ccatcctctc ccatactcta aatcccggca                    40


<210> SEQ ID NO 2
<211> LENGTH: 21
<212> TYPE: DNA
<213> ORGANISM: Acinetobacter

<400> SEQUENCE: 2

accatcctct cccatactct a                                        21


<210> SEQ ID NO 3
<211> LENGTH: 21
<212> TYPE: DNA
<213> ORGANISM: Acinetobacter

<400> SEQUENCE: 3
```

tagagtatgg gagaggatgg t 21

<210> SEQ ID NO 4
<211> LENGTH: 30
<212> TYPE: DNA
<213> ORGANISM: Acinetobacter baumannii

<400> SEQUENCE: 4
gcgcgtccgg tagcaagcta ccttccgcgc 30

<210> SEQ ID NO 5
<211> LENGTH: 20
<212> TYPE: DNA
<213> ORGANISM: Acinetobacter baumannii

<400> SEQUENCE: 5
tccggtagca agctaccttc 20

<210> SEQ ID NO 6
<211> LENGTH: 20
<212> TYPE: DNA
<213> ORGANISM: Acinetobacter baumannii

<400> SEQUENCE: 6
gaaggtagct tgctaccgga 20

<210> SEQ ID NO 7
<211> LENGTH: 41
<212> TYPE: DNA
<213> ORGANISM: Aspergillus flavus

<400> SEQUENCE: 7
ccgccggcgt acagagttcg tggtgtctcc tcgcccagcg g 41

<210> SEQ ID NO 8
<211> LENGTH: 20
<212> TYPE: DNA
<213> ORGANISM: Aspergillus flavus

<400> SEQUENCE: 8
acagagttcg tggtgtctcc 20

<210> SEQ ID NO 9
<211> LENGTH: 20
<212> TYPE: DNA
<213> ORGANISM: Aspergillus flavus

<400> SEQUENCE: 9
ggagacacca cgaactctgt 20

<210> SEQ ID NO 10
<211> LENGTH: 23
<212> TYPE: DNA
<213> ORGANISM: Aspergillus fumigatus

<400> SEQUENCE: 10
cgtcgcctac agagcaggtg acg 23

<210> SEQ ID NO 11
<211> LENGTH: 18
<212> TYPE: DNA
<213> ORGANISM: Aspergillus fumigatus

<400> SEQUENCE: 11
gcctacagag caggtgac 18

<210> SEQ ID NO 12
<211> LENGTH: 18
<212> TYPE: DNA
<213> ORGANISM: Aspergillus fumigatus

<400> SEQUENCE: 12
gtcacctgct ctgtaggc 18

<210> SEQ ID NO 13
<211> LENGTH: 32
<212> TYPE: DNA
<213> ORGANISM: Aspergillus niger

<400> SEQUENCE: 13
ctctgaactg attgcattca atcaactcag ag 32

<210> SEQ ID NO 14
<211> LENGTH: 25
<212> TYPE: DNA
<213> ORGANISM: Aspergillus niger

<400> SEQUENCE: 14
actgattgca ttcaatcaac tcaga 25

<210> SEQ ID NO 15
<211> LENGTH: 25
<212> TYPE: DNA
<213> ORGANISM: Aspergillus niger

<400> SEQUENCE: 15
tctgagttga ttgaatgcaa tcagt 25

<210> SEQ ID NO 16
<211> LENGTH: 36
<212> TYPE: DNA
<213> ORGANISM: Aspergillus terreus

<400> SEQUENCE: 16
tccgtctgat tgcaaagaat cacactcaga gacgga 36

<210> SEQ ID NO 17
<211> LENGTH: 24
<212> TYPE: DNA
<213> ORGANISM: Aspergillus terreus

<400> SEQUENCE: 17
tgattgcaaa gaatcacact caga 24

<210> SEQ ID NO 18
<211> LENGTH: 24
<212> TYPE: DNA
<213> ORGANISM: Aspergillus terreus

<400> SEQUENCE: 18
tctgagtgtg attctttgca atca 24

<210> SEQ ID NO 19
<211> LENGTH: 41
<212> TYPE: DNA
<213> ORGANISM: Bacteroides

<400> SEQUENCE: 19
gccgccggca tccaatgtgg gggaccttct agcccagcgg c 41

<210> SEQ ID NO 20
<211> LENGTH: 18
<212> TYPE: DNA
<213> ORGANISM: Bacteroides

<400> SEQUENCE: 20
ccaatgtggg ggaccttc 18

<210> SEQ ID NO 21
<211> LENGTH: 18
<212> TYPE: DNA
<213> ORGANISM: Bacteroides

<400> SEQUENCE: 21
gaaggtcccc cacattgg 18

<210> SEQ ID NO 22
<211> LENGTH: 39
<212> TYPE: DNA
<213> ORGANISM: Borrelia burgdorferi

<400> SEQUENCE: 22
tgccggattc atgcttaaga cgcactgcca atcccggca 39

<210> SEQ ID NO 23
<211> LENGTH: 20
<212> TYPE: DNA
<213> ORGANISM: Borrelia burgdorferi

<400> SEQUENCE: 23
catgcttaag acgcactgcc 20

<210> SEQ ID NO 24
<211> LENGTH: 20
<212> TYPE: DNA
<213> ORGANISM: Borrelia burgdorferi

<400> SEQUENCE: 24
ggcagtgcgt cttaagcatg 20

<210> SEQ ID NO 25
<211> LENGTH: 40
<212> TYPE: DNA
<213> ORGANISM: Bordetella pertussis

<400> SEQUENCE: 25
tgccggattc agcactctgc aaagacgaaa aatcccggca 40

<210> SEQ ID NO 26
<211> LENGTH: 21
<212> TYPE: DNA
<213> ORGANISM: Bordetella pertussis

<400> SEQUENCE: 26
cagcactctg caaagacgaa a 21

<210> SEQ ID NO 27
<211> LENGTH: 21
<212> TYPE: DNA
<213> ORGANISM: Bordetella pertussis

<400> SEQUENCE: 27
tttcgtcttt gcagagtgct g 21

<210> SEQ ID NO 28
<211> LENGTH: 39
<212> TYPE: DNA
<213> ORGANISM: Burkholderia cepacia

<400> SEQUENCE: 28
accgctcttt ctttccggac aaaagtgctt tgagcggct 39

<210> SEQ ID NO 29
<211> LENGTH: 24
<212> TYPE: DNA
<213> ORGANISM: Burkholderia cepacia

<400> SEQUENCE: 29
tttctttccg gacaaaagtg cttt 24

<210> SEQ ID NO 30
<211> LENGTH: 24
<212> TYPE: DNA
<213> ORGANISM: Burkholderia cepacia

<400> SEQUENCE: 30
aaagcacttt tgtccggaaa gaaa 24

<210> SEQ ID NO 31
<211> LENGTH: 36
<212> TYPE: DNA
<213> ORGANISM: Burkholderia cepacia

<400> SEQUENCE: 31
cgccttcaga accaaggatt tctttccggg aaggcg 36

<210> SEQ ID NO 32
<211> LENGTH: 22
<212> TYPE: DNA
<213> ORGANISM: Burkholderia cepacia

<400> SEQUENCE: 32
agaaccaagg atttctttcc gg 22

<210> SEQ ID NO 33
<211> LENGTH: 22
<212> TYPE: DNA
<213> ORGANISM: Burkholderia cepacia

<400> SEQUENCE: 33
ccggaaagaa atccttggtt ct 22

<210> SEQ ID NO 34
<211> LENGTH: 33
<212> TYPE: DNA
<213> ORGANISM: Artificial Sequence
<220> FEATURE:
<223> OTHER INFORMATION: target

<400> SEQUENCE: 34
acgcaagagc caaggttttc tttccgcttg cgt 33

<210> SEQ ID NO 35

<211> LENGTH: 21
<212> TYPE: DNA
<213> ORGANISM: Artificial Sequence
<220> FEATURE:
<223> OTHER INFORMATION: target

<400> SEQUENCE: 35
agagccaagg ttttctttcc g 21

<210> SEQ ID NO 36
<211> LENGTH: 21
<212> TYPE: DNA
<213> ORGANISM: Artificial Sequence
<220> FEATURE:
<223> OTHER INFORMATION: target

<400> SEQUENCE: 36
cggaaagaaa accttggctc t 21

<210> SEQ ID NO 37
<211> LENGTH: 28
<212> TYPE: DNA
<213> ORGANISM: Burkholderia cepacia

<400> SEQUENCE: 37
acgctcgtca tcccccggcc atgagcgt 28

<210> SEQ ID NO 38
<211> LENGTH: 16
<212> TYPE: DNA
<213> ORGANISM: Burkholderia cepacia

<400> SEQUENCE: 38
gtcatccccc ggccat 16

<210> SEQ ID NO 39
<211> LENGTH: 16
<212> TYPE: DNA
<213> ORGANISM: Burkholderia cepacia

<400> SEQUENCE: 39
atggccgggg gatgac 16

<210> SEQ ID NO 40
<211> LENGTH: 29
<212> TYPE: DNA
<213> ORGANISM: Burkholderia pyrrocinia

<400> SEQUENCE: 40
cgctccgtca tcccccggct ataggagcg 29

<210> SEQ ID NO 41
<211> LENGTH: 18
<212> TYPE: DNA
<213> ORGANISM: Burkholderia pyrrocinia

<400> SEQUENCE: 41
cgtcatcccc cggctata 18

<210> SEQ ID NO 42
<211> LENGTH: 18
<212> TYPE: DNA
<213> ORGANISM: Burkholderia pyrrocinia

<400> SEQUENCE: 42
tatagccggg ggatgacg 18

<210> SEQ ID NO 43
<211> LENGTH: 29
<212> TYPE: DNA
<213> ORGANISM: Burkholderia dolosa

<400> SEQUENCE: 43
ccgctcgtca tcccccggct gtagagcgg 29

<210> SEQ ID NO 44
<211> LENGTH: 17
<212> TYPE: DNA
<213> ORGANISM: Burkholderia dolosa

<400> SEQUENCE: 44
gtcatccccc ggctgta 17

<210> SEQ ID NO 45
<211> LENGTH: 17
<212> TYPE: DNA
<213> ORGANISM: Burkholderia dolosa

<400> SEQUENCE: 45
tacagccggg ggatgac 17

<210> SEQ ID NO 46
<211> LENGTH: 41
<212> TYPE: DNA
<213> ORGANISM: Burkholderia multivorans

<400> SEQUENCE: 46
gccgccggcg tcgtcatccc ccgatcgtat cgcccagcgg c 41

<210> SEQ ID NO 47
<211> LENGTH: 18
<212> TYPE: DNA
<213> ORGANISM: Burkholderia multivorans

<400> SEQUENCE: 47
cgtcatcccc cgatcgta 18

<210> SEQ ID NO 48
<211> LENGTH: 18
<212> TYPE: DNA
<213> ORGANISM: Burkholderia multivorans

<400> SEQUENCE: 48
tacgatcggg ggatgacg 18

<210> SEQ ID NO 49
<211> LENGTH: 41
<212> TYPE: DNA
<213> ORGANISM: Burkholderia cenocepacia

<400> SEQUENCE: 49
gccgccggcg tcgtcatccc ccgactgtat cgcccagcgg c 41

<210> SEQ ID NO 50
<211> LENGTH: 18
<212> TYPE: DNA
<213> ORGANISM: Burkholderia cenocepacia

<400> SEQUENCE: 50
cgtcatcccc cgactgta 18

<210> SEQ ID NO 51
<211> LENGTH: 18
<212> TYPE: DNA
<213> ORGANISM: Burkholderia cenocepacia

<400> SEQUENCE: 51
tacagtcggg ggatgacg 18

<210> SEQ ID NO 52
<211> LENGTH: 18
<212> TYPE: DNA
<213> ORGANISM: Campylobacter

<400> SEQUENCE: 52
gccctaagcg tccttcca 18

<210> SEQ ID NO 53
<211> LENGTH: 31
<212> TYPE: DNA
<213> ORGANISM: Campylobacter lari

<400> SEQUENCE: 53
acgctcgaag tgtaagcaac taaatgagcg t 31

<210> SEQ ID NO 54
<211> LENGTH: 19
<212> TYPE: DNA
<213> ORGANISM: Campylobacter lari

<400> SEQUENCE: 54
gaagtgtaag caactaaat 19

<210> SEQ ID NO 55
<211> LENGTH: 19
<212> TYPE: DNA
<213> ORGANISM: Campylobacter lari

<400> SEQUENCE: 55
atttagttgc ttacacttc 19

<210> SEQ ID NO 56
<211> LENGTH: 30
<212> TYPE: DNA
<213> ORGANISM: Campylobacter jejuni

<400> SEQUENCE: 56
acgctcagct aaccacttat accggagcgt 30

<210> SEQ ID NO 57
<211> LENGTH: 18
<212> TYPE: DNA
<213> ORGANISM: Campylobacter jejuni

<400> SEQUENCE: 57
agctaaccac ttataccg 18

<210> SEQ ID NO 58
<211> LENGTH: 18
<212> TYPE: DNA
<213> ORGANISM: Campylobacter jejuni

<400> SEQUENCE: 58
cggtataagt ggttagct 18

<210> SEQ ID NO 59
<211> LENGTH: 32
<212> TYPE: DNA
<213> ORGANISM: Campylobacter upsaliensis

<400> SEQUENCE: 59
ccgctccgtg tgtcgcccta ggcgtagagc gg 32

<210> SEQ ID NO 60
<211> LENGTH: 20
<212> TYPE: DNA
<213> ORGANISM: Campylobacter upsaliensis

<400> SEQUENCE: 60
cgtgtgtcgc cctaggcgta 20

<210> SEQ ID NO 61
<211> LENGTH: 20
<212> TYPE: DNA
<213> ORGANISM: Campylobacter upsaliensis

<400> SEQUENCE: 61
tacgcctagg gcgacacacg 20

<210> SEQ ID NO 62
<211> LENGTH: 30
<212> TYPE: DNA
<213> ORGANISM: Campylobacter coli

<400> SEQUENCE: 62
ccgctctcga tggcatcagg ggttgagcgg 30

<210> SEQ ID NO 63
<211> LENGTH: 18
<212> TYPE: DNA
<213> ORGANISM: Campylobacter coli

<400> SEQUENCE: 63
tcgatggcat caggggtt 18

<210> SEQ ID NO 64
<211> LENGTH: 18
<212> TYPE: DNA
<213> ORGANISM: Campylobacter coli

<400> SEQUENCE: 64
aacccctgat gccatcga 18

<210> SEQ ID NO 65

<400> SEQUENCE: 65

000

<210> SEQ ID NO 66
<211> LENGTH: 18
<212> TYPE: DNA
<213> ORGANISM: Campylobacter coli

<400> SEQUENCE: 66
tcgacggcat caggggtt 18

<210> SEQ ID NO 67
<211> LENGTH: 18
<212> TYPE: DNA
<213> ORGANISM: Campylobacter coli

<400> SEQUENCE: 67
aacccctgat gccgtcga 18

<210> SEQ ID NO 68
<211> LENGTH: 39
<212> TYPE: DNA
<213> ORGANISM: Chlamydia

<400> SEQUENCE: 68
acgccggcgt tagctgatat cacatagatc gcccagcgt 39

<210> SEQ ID NO 69
<211> LENGTH: 18
<212> TYPE: DNA
<213> ORGANISM: Chlamydia

<400> SEQUENCE: 69
tagctgatat cacataga 18

<210> SEQ ID NO 70
<211> LENGTH: 18
<212> TYPE: DNA
<213> ORGANISM: Chlamydia

<400> SEQUENCE: 70
tctatgtgat atcagcta 18

<210> SEQ ID NO 71
<211> LENGTH: 41
<212> TYPE: DNA
<213> ORGANISM: Unknown
<220> FEATURE:
<223> OTHER INFORMATION: Chlamydiaceae

<400> SEQUENCE: 71
tccgccggcg tctttccgcc tacacgccct cgcccagcgg a 41

<210> SEQ ID NO 72
<211> LENGTH: 18
<212> TYPE: DNA
<213> ORGANISM: Unknown
<220> FEATURE:
<223> OTHER INFORMATION: Chlamydiaceae

<400> SEQUENCE: 72
ctttccgcct acacgccc 18

<210> SEQ ID NO 73
<211> LENGTH: 18
<212> TYPE: DNA
<213> ORGANISM: Unknown
<220> FEATURE:
<223> OTHER INFORMATION: Chlamydiaceae

<400> SEQUENCE: 73
gggcgtgtag gcggaaag 18

<210> SEQ ID NO 74
<211> LENGTH: 41
<212> TYPE: DNA
<213> ORGANISM: Unknown
<220> FEATURE:
<223> OTHER INFORMATION: Chlamydiales

<400> SEQUENCE: 74
tccgccggcg tcctccgtat taccgcagct cgcccagcgg a 41

<210> SEQ ID NO 75
<211> LENGTH: 18
<212> TYPE: DNA
<213> ORGANISM: Unknown
<220> FEATURE:
<223> OTHER INFORMATION: Chlamydiales

<400> SEQUENCE: 75
cctccgtatt accgcagc 18

<210> SEQ ID NO 76
<211> LENGTH: 18
<212> TYPE: DNA
<213> ORGANISM: Unknown
<220> FEATURE:
<223> OTHER INFORMATION: Chlamydiales

<400> SEQUENCE: 76
gctgcggtaa tacggagg 18

<210> SEQ ID NO 77
<211> LENGTH: 39
<212> TYPE: DNA
<213> ORGANISM: Chlamydophila

<400> SEQUENCE: 77
acgccggcgt ctaactttcc tttccgcctc gcccagcgt 39

<210> SEQ ID NO 78
<211> LENGTH: 18
<212> TYPE: DNA
<213> ORGANISM: Chlamydophila

<400> SEQUENCE: 78
ctaactttcc tttccgcc 18

<210> SEQ ID NO 79
<211> LENGTH: 18
<212> TYPE: DNA
<213> ORGANISM: Chlamydophila

<400> SEQUENCE: 79
ggcggaaagg aaagttag 18

<210> SEQ ID NO 80
<211> LENGTH: 41
<212> TYPE: DNA
<213> ORGANISM: Chlamydia pneumoniae

<400> SEQUENCE: 80
tccaccggcg tctcttcctc aaccgaaagt cgcccagtgg a 41

<210> SEQ ID NO 81
<211> LENGTH: 18

<212> TYPE: DNA
<213> ORGANISM: Chlamydia pneumoniae

<400> SEQUENCE: 81
ctcttcctca accgaaag 18

<210> SEQ ID NO 82
<211> LENGTH: 18
<212> TYPE: DNA
<213> ORGANISM: Chlamydia pneumoniae

<400> SEQUENCE: 82
ctttcggttg aggaagag 18

<210> SEQ ID NO 83
<211> LENGTH: 41
<212> TYPE: DNA
<213> ORGANISM: Chlamydia psittaci

<400> SEQUENCE: 83
tcagccggcg taaggcaaaa ccaactccct cgcccagctg a 41

<210> SEQ ID NO 84
<211> LENGTH: 18
<212> TYPE: DNA
<213> ORGANISM: Chlamydia psittaci

<400> SEQUENCE: 84
aaggcaaaac caactccc 18

<210> SEQ ID NO 85
<211> LENGTH: 18
<212> TYPE: DNA
<213> ORGANISM: Chlamydia psittaci

<400> SEQUENCE: 85
gggagttggt tttgcctt 18

<210> SEQ ID NO 86
<211> LENGTH: 39
<212> TYPE: DNA
<213> ORGANISM: Unknown
<220> FEATURE:
<223> OTHER INFORMATION: Parachlamydiaceae

<400> SEQUENCE: 86
ccgccggcgt tccgttttct ccgcctactc gcccagcgg 39

<210> SEQ ID NO 87
<211> LENGTH: 18
<212> TYPE: DNA
<213> ORGANISM: Unknown
<220> FEATURE:
<223> OTHER INFORMATION: Parachlamydiaceae

<400> SEQUENCE: 87
tccgttttct ccgcctac 18

<210> SEQ ID NO 88
<211> LENGTH: 18
<212> TYPE: DNA
<213> ORGANISM: Unknown
<220> FEATURE:
<223> OTHER INFORMATION: Parachlamydiaceae

<400> SEQUENCE: 88
gtaggcggag aaaacgga 18

<210> SEQ ID NO 89
<211> LENGTH: 41
<212> TYPE: DNA
<213> ORGANISM: Chlamydia sp.

<400> SEQUENCE: 89
tccgccggcg tgctcccctt gctttcgcgt cgcccagcgg a 41

<210> SEQ ID NO 90
<211> LENGTH: 18
<212> TYPE: DNA
<213> ORGANISM: Chlamydia sp.

<400> SEQUENCE: 90
gctccccttg ctttcgcg 18

<210> SEQ ID NO 91
<211> LENGTH: 18
<212> TYPE: DNA
<213> ORGANISM: Chlamydia sp.

<400> SEQUENCE: 91
cgcgaaagca aggggagc 18

<210> SEQ ID NO 92
<211> LENGTH: 30
<212> TYPE: DNA
<213> ORGANISM: Chlamydia trachomatis

<400> SEQUENCE: 92
acgctctcgg atgcccaaat atcggagcgt 30

<210> SEQ ID NO 93
<211> LENGTH: 18
<212> TYPE: DNA
<213> ORGANISM: Chlamydia trachomatis

<400> SEQUENCE: 93
tcggatgccc aaatatcg 18

<210> SEQ ID NO 94
<211> LENGTH: 18
<212> TYPE: DNA
<213> ORGANISM: Chlamydia trachomatis

<400> SEQUENCE: 94
cgatatttgg gcatccga 18

<210> SEQ ID NO 95
<211> LENGTH: 29
<212> TYPE: DNA
<213> ORGANISM: Candida albicans

<400> SEQUENCE: 95
ggaatggcta cccagaagga aaccattcc 29

<210> SEQ ID NO 96
<211> LENGTH: 20
<212> TYPE: DNA
<213> ORGANISM: Candida albicans

<400> SEQUENCE: 96
aatggctacc cagaaggaaa 20

<210> SEQ ID NO 97
<211> LENGTH: 20
<212> TYPE: DNA
<213> ORGANISM: Candida albicans

<400> SEQUENCE: 97
tttccttctg ggtagccatt 20

<210> SEQ ID NO 98
<211> LENGTH: 36
<212> TYPE: DNA
<213> ORGANISM: Candida krusei

<400> SEQUENCE: 98
ccgctctgta ttagctctag atttccacgg gagcgg 36

<210> SEQ ID NO 99
<211> LENGTH: 24
<212> TYPE: DNA
<213> ORGANISM: Candida krusei

<400> SEQUENCE: 99
tgtattagct ctagatttcc acgg 24

<210> SEQ ID NO 100
<211> LENGTH: 24
<212> TYPE: DNA
<213> ORGANISM: Candida krusei

<400> SEQUENCE: 100
ccgtggaaat ctagagctaa taca 24

<210> SEQ ID NO 101
<211> LENGTH: 32
<212> TYPE: DNA
<213> ORGANISM: Candida dubliniensis

<400> SEQUENCE: 101
gtttgccccg aaagagtaac ttgcaggcaa ac 32

<210> SEQ ID NO 102
<211> LENGTH: 20
<212> TYPE: DNA
<213> ORGANISM: Candida dubliniensis

<400> SEQUENCE: 102
ccccgaaaga gtaacttgca 20

<210> SEQ ID NO 103
<211> LENGTH: 20
<212> TYPE: DNA
<213> ORGANISM: Candida dubliniensis

<400> SEQUENCE: 103
tgcaagttac tctttcgggg 20

<210> SEQ ID NO 104
<211> LENGTH: 40
<212> TYPE: DNA

<213> ORGANISM: Candida glabrata

<400> SEQUENCE: 104
gccgccggcg tggccaccca ggcccaaatc gcccagcggc 40

<210> SEQ ID NO 105
<211> LENGTH: 17
<212> TYPE: DNA
<213> ORGANISM: Candida glabrata

<400> SEQUENCE: 105
ggccacccag gcccaaa 17

<210> SEQ ID NO 106
<211> LENGTH: 17
<212> TYPE: DNA
<213> ORGANISM: Candida glabrata

<400> SEQUENCE: 106
tttgggcctg ggtggcc 17

<210> SEQ ID NO 107
<211> LENGTH: 43
<212> TYPE: DNA
<213> ORGANISM: Candida parapsilosis

<400> SEQUENCE: 107
gccgccggcg tgccaaaaag gctagccaga atcgcccagc ggc 43

<210> SEQ ID NO 108
<211> LENGTH: 20
<212> TYPE: DNA
<213> ORGANISM: Candida parapsilosis

<400> SEQUENCE: 108
gccaaaaagg ctagccagaa 20

<210> SEQ ID NO 109
<211> LENGTH: 20
<212> TYPE: DNA
<213> ORGANISM: Candida parapsilosis

<400> SEQUENCE: 109
ttctggctag cctttttggc 20

<210> SEQ ID NO 110
<211> LENGTH: 24
<212> TYPE: DNA
<213> ORGANISM: Candida sp.

<400> SEQUENCE: 110
acgcgcttgg ctggccggtc gcgt 24

<210> SEQ ID NO 111
<211> LENGTH: 16
<212> TYPE: DNA
<213> ORGANISM: Candida sp.

<400> SEQUENCE: 111
gaccggccag ccaagc 16

<210> SEQ ID NO 112
<211> LENGTH: 16

<212> TYPE: DNA
<213> ORGANISM: Candida sp.

<400> SEQUENCE: 112
gcttggctgg ccggtc 16

<210> SEQ ID NO 113
<211> LENGTH: 44
<212> TYPE: DNA
<213> ORGANISM: Candida tropicales

<400> SEQUENCE: 113
accgccggcg ttacgcatca gaaagatgga cctcgcccag cggt 44

<210> SEQ ID NO 114
<211> LENGTH: 21
<212> TYPE: DNA
<213> ORGANISM: Candida tropicales

<400> SEQUENCE: 114
tacgcatcag aaagatggac c 21

<210> SEQ ID NO 115
<211> LENGTH: 21
<212> TYPE: DNA
<213> ORGANISM: Candida tropicales

<400> SEQUENCE: 115
ggtccatctt tctgatgcgt a 21

<210> SEQ ID NO 116
<211> LENGTH: 40
<212> TYPE: DNA
<213> ORGANISM: Citrobacter freundii

<400> SEQUENCE: 116
tgccggattc tacttgttag gtgactgcgt aatcccggca 40

<210> SEQ ID NO 117
<211> LENGTH: 21
<212> TYPE: DNA
<213> ORGANISM: Citrobacter freundii

<400> SEQUENCE: 117
ctacttgtta ggtgactgcg t 21

<210> SEQ ID NO 118
<211> LENGTH: 21
<212> TYPE: DNA
<213> ORGANISM: Citrobacter freundii

<400> SEQUENCE: 118
acgcagtcac ctaacaagta g 21

<210> SEQ ID NO 119
<211> LENGTH: 33
<212> TYPE: DNA
<213> ORGANISM: Clostridium botulinum

<400> SEQUENCE: 119
tcttgtagtg ccgtttcatg cgaaactaca aga 33

<210> SEQ ID NO 120

<211> LENGTH: 22
<212> TYPE: DNA
<213> ORGANISM: Clostridium botulinum

<400> SEQUENCE: 120
gccgtttcat gcgaaactac aa 22

<210> SEQ ID NO 121
<211> LENGTH: 22
<212> TYPE: DNA
<213> ORGANISM: Clostridium botulinum

<400> SEQUENCE: 121
ttgtagtttc gcatgaaacg gc 22

<210> SEQ ID NO 122
<211> LENGTH: 46
<212> TYPE: DNA
<213> ORGANISM: Clostridium difficile

<400> SEQUENCE: 122
gccgccggcg tcgaagtaaa tcgctcaact tgcatcgccc agcggc 46

<210> SEQ ID NO 123
<211> LENGTH: 23
<212> TYPE: DNA
<213> ORGANISM: Clostridium difficile

<400> SEQUENCE: 123
cgaagtaaat cgctcaactt gca 23

<210> SEQ ID NO 124
<211> LENGTH: 23
<212> TYPE: DNA
<213> ORGANISM: Clostridium difficile

<400> SEQUENCE: 124
tgcaagttga gcgatttact tcg 23

<210> SEQ ID NO 125
<211> LENGTH: 29
<212> TYPE: DNA
<213> ORGANISM: Clostridium sp.

<400> SEQUENCE: 125
cgctcacacc cgtccgccgc taatgagcg 29

<210> SEQ ID NO 126
<211> LENGTH: 18
<212> TYPE: DNA
<213> ORGANISM: Clostridium sp.

<400> SEQUENCE: 126
cacccgtccg ccgctaat 18

<210> SEQ ID NO 127
<211> LENGTH: 18
<212> TYPE: DNA
<213> ORGANISM: Clostridium sp.

<400> SEQUENCE: 127
attagcggcg gacgggtg 18

<210> SEQ ID NO 128
<211> LENGTH: 47
<212> TYPE: DNA
<213> ORGANISM: Clostridium perfringens

<400> SEQUENCE: 128
gccgccggcg tgattgctcc tttggttgaa tgatgtcgcc cagcggc 47

<210> SEQ ID NO 129
<211> LENGTH: 24
<212> TYPE: DNA
<213> ORGANISM: Clostridium perfringens

<400> SEQUENCE: 129
gattgctcct ttggttgaat gatg 24

<210> SEQ ID NO 130
<211> LENGTH: 24
<212> TYPE: DNA
<213> ORGANISM: Clostridium perfringens

<400> SEQUENCE: 130
catcattcaa ccaaaggagc aatc 24

<210> SEQ ID NO 131
<211> LENGTH: 31
<212> TYPE: DNA
<213> ORGANISM: Clostridium perfringens

<400> SEQUENCE: 131
acgctcggtt gaatgatgat gccatgagcg t 31

<210> SEQ ID NO 132
<211> LENGTH: 23
<212> TYPE: DNA
<213> ORGANISM: Clostridium perfringens

<400> SEQUENCE: 132
ggttgaatga tgatgccatc ttt 23

<210> SEQ ID NO 133
<211> LENGTH: 23
<212> TYPE: DNA
<213> ORGANISM: Clostridium perfringens

<400> SEQUENCE: 133
aaagatggca tcatcattca acc 23

<210> SEQ ID NO 134
<211> LENGTH: 27
<212> TYPE: DNA
<213> ORGANISM: Clostridium tetani

<400> SEQUENCE: 134
gcggacctgt gttactcacc cgtccgc 27

<210> SEQ ID NO 135
<211> LENGTH: 20
<212> TYPE: DNA
<213> ORGANISM: Clostridium tetani

<400> SEQUENCE: 135
ctgtgttact cacccgtccg 20

<210> SEQ ID NO 136
<211> LENGTH: 20
<212> TYPE: DNA
<213> ORGANISM: Clostridium tetani

<400> SEQUENCE: 136
cggacgggtg agtaacacag 20

<210> SEQ ID NO 137
<211> LENGTH: 40
<212> TYPE: DNA
<213> ORGANISM: Unknown
<220> FEATURE:
<223> OTHER INFORMATION: Enterobacteriaceae

<400> SEQUENCE: 137
tgccggattt tcgtgtttgc acagtgctgt aatcccggca 40

<210> SEQ ID NO 138
<211> LENGTH: 21
<212> TYPE: DNA
<213> ORGANISM: Unknown
<220> FEATURE:
<223> OTHER INFORMATION: Enterobacteriaceae

<400> SEQUENCE: 138
ttcgtgtttg cacagtgctg t 21

<210> SEQ ID NO 139
<211> LENGTH: 21
<212> TYPE: DNA
<213> ORGANISM: Unknown
<220> FEATURE:
<223> OTHER INFORMATION: Enterobacteriaceae

<400> SEQUENCE: 139
acagcactgt gcaaacacga a 21

<210> SEQ ID NO 140
<211> LENGTH: 37
<212> TYPE: DNA
<213> ORGANISM: Unknown
<220> FEATURE:
<223> OTHER INFORMATION: Enterobacteriaceae

<400> SEQUENCE: 140
tgccggattt ctcgcgaggt cgcttctaat cccggca 37

<210> SEQ ID NO 141
<211> LENGTH: 18
<212> TYPE: DNA
<213> ORGANISM: Unknown
<220> FEATURE:
<223> OTHER INFORMATION: Enterobacteriaceae

<400> SEQUENCE: 141
tctcgcgagg tcgcttct 18

<210> SEQ ID NO 142
<211> LENGTH: 18
<212> TYPE: DNA
<213> ORGANISM: Unknown
<220> FEATURE:
<223> OTHER INFORMATION: Enterobacteriaceae

<400> SEQUENCE: 142
agaagcgacc tcgcgaga 18

<210> SEQ ID NO 143
<211> LENGTH: 39
<212> TYPE: DNA
<213> ORGANISM: Unknown
<220> FEATURE:
<223> OTHER INFORMATION: Enterobacteriaceae

<400> SEQUENCE: 143
tgccggattc ccccwctttg gtcttgcgaa atcccggca 39

<210> SEQ ID NO 144
<211> LENGTH: 20
<212> TYPE: DNA
<213> ORGANISM: Unknown
<220> FEATURE:
<223> OTHER INFORMATION: Enterobacteriaceae

<400> SEQUENCE: 144
cccccwcttt ggtcttgcga 20

<210> SEQ ID NO 145
<211> LENGTH: 20
<212> TYPE: DNA
<213> ORGANISM: Unknown
<220> FEATURE:
<223> OTHER INFORMATION: Enterobacteriaceae

<400> SEQUENCE: 145
tcgcaagacc aaagwggggg 20

<210> SEQ ID NO 146
<211> LENGTH: 37
<212> TYPE: DNA
<213> ORGANISM: Enterococcus

<400> SEQUENCE: 146
tgccggatta tccatcagcg acacccgaat cccggca 37

<210> SEQ ID NO 147
<211> LENGTH: 18
<212> TYPE: DNA
<213> ORGANISM: Enterococcus

<400> SEQUENCE: 147
atccatcagc gacacccg 18

<210> SEQ ID NO 148
<211> LENGTH: 18
<212> TYPE: DNA
<213> ORGANISM: Enterococcus

<400> SEQUENCE: 148
cgggtgtcgc tgatggat 18

<210> SEQ ID NO 149
<211> LENGTH: 37
<212> TYPE: DNA
<213> ORGANISM: Enterococcus faecalis

<400> SEQUENCE: 149
tgccggattc cctctgatgg gtaggttaat cccggca 37

<210> SEQ ID NO 150
<211> LENGTH: 18
<212> TYPE: DNA
<213> ORGANISM: Enterococcus faecalis

<400> SEQUENCE: 150
ccctctgatg ggtaggtt 18

<210> SEQ ID NO 151
<211> LENGTH: 18
<212> TYPE: DNA
<213> ORGANISM: Enterococcus faecalis

<400> SEQUENCE: 151
aacctaccca tcagaggg 18

<210> SEQ ID NO 152
<211> LENGTH: 47
<212> TYPE: DNA
<213> ORGANISM: Enterococcus faecium

<400> SEQUENCE: 152
gccgccggcg tttcaaatca aaaccatgcg gtttctcgcc cagcggc 47

<210> SEQ ID NO 153
<211> LENGTH: 24
<212> TYPE: DNA
<213> ORGANISM: Enterococcus faecium

<400> SEQUENCE: 153
ttcaaatcaa aaccatgcgg tttc 24

<210> SEQ ID NO 154
<211> LENGTH: 24
<212> TYPE: DNA
<213> ORGANISM: Enterococcus faecium

<400> SEQUENCE: 154
gaaaccgcat ggttttgatt tgaa 24

<210> SEQ ID NO 155
<211> LENGTH: 40
<212> TYPE: DNA
<213> ORGANISM: Escherichia coli

<400> SEQUENCE: 155
tgccggattg gaagaagctt gcttctttgc aatcccggca 40

<210> SEQ ID NO 156
<211> LENGTH: 21
<212> TYPE: DNA
<213> ORGANISM: Escherichia coli

<400> SEQUENCE: 156
ggaagaagct tgcttctttg c 21

<210> SEQ ID NO 157
<211> LENGTH: 21
<212> TYPE: DNA
<213> ORGANISM: Escherichia coli

<400> SEQUENCE: 157
gcaaagaagc aagcttcttc c 21

<210> SEQ ID NO 158
<211> LENGTH: 28
<212> TYPE: DNA
<213> ORGANISM: Unknown
<220> FEATURE:
<223> OTHER INFORMATION: Bacteria

<400> SEQUENCE: 158
cgctcgctgc ctcccgtagg agtgagcg 28

<210> SEQ ID NO 159
<211> LENGTH: 18
<212> TYPE: DNA
<213> ORGANISM: Unknown
<220> FEATURE:
<223> OTHER INFORMATION: Bacteria

<400> SEQUENCE: 159
gctgcctccc gtaggagt 18

<210> SEQ ID NO 160
<211> LENGTH: 18
<212> TYPE: DNA
<213> ORGANISM: Unknown
<220> FEATURE:
<223> OTHER INFORMATION: Bacteria

<400> SEQUENCE: 160
actcctacgg gaggcagc 18

<210> SEQ ID NO 161
<211> LENGTH: 30
<212> TYPE: DNA
<213> ORGANISM: Gardnerella vaginalis

<400> SEQUENCE: 161
acgctccacc atgaagcaac ccgtgagcgt 30

<210> SEQ ID NO 162
<211> LENGTH: 18
<212> TYPE: DNA
<213> ORGANISM: Gardnerella vaginalis

<400> SEQUENCE: 162
caccatgaag caacccgt 18

<210> SEQ ID NO 163
<211> LENGTH: 18
<212> TYPE: DNA
<213> ORGANISM: Gardnerella vaginalis

<400> SEQUENCE: 163
acgggttgct tcatggtg 18

<210> SEQ ID NO 164
<211> LENGTH: 35
<212> TYPE: DNA
<213> ORGANISM: Haemophilus influenzae

<400> SEQUENCE: 164
acccgctatt ccgataatac gcggtattag cgggt 35

<210> SEQ ID NO 165

<211> LENGTH: 23
<212> TYPE: DNA
<213> ORGANISM: Haemophilus influenzae

<400> SEQUENCE: 165
ttccgataat acgcggtatt agc 23

<210> SEQ ID NO 166
<211> LENGTH: 23
<212> TYPE: DNA
<213> ORGANISM: Haemophilus influenzae

<400> SEQUENCE: 166
gctaataccg cgtattatcg gaa 23

<210> SEQ ID NO 167
<211> LENGTH: 39
<212> TYPE: DNA
<213> ORGANISM: Haemophilus influenzae

<400> SEQUENCE: 167
cggtgctcta atacgcggta ttagcgacag agagcaccg 39

<210> SEQ ID NO 168
<211> LENGTH: 22
<212> TYPE: DNA
<213> ORGANISM: Haemophilus influenzae

<400> SEQUENCE: 168
taatacgcgg tattagcgac ag 22

<210> SEQ ID NO 169
<211> LENGTH: 22
<212> TYPE: DNA
<213> ORGANISM: Haemophilus influenzae

<400> SEQUENCE: 169
ctgtcgctaa taccgcgtat at 22

<210> SEQ ID NO 170
<211> LENGTH: 42
<212> TYPE: DNA
<213> ORGANISM: Klebsiella pneumoniae

<400> SEQUENCE: 170
acgccggcgt aggttattaa cctcatcgcc ttcgcccagc gt 42

<210> SEQ ID NO 171
<211> LENGTH: 21
<212> TYPE: DNA
<213> ORGANISM: Klebsiella pneumoniae

<400> SEQUENCE: 171
aggttattaa cctcatcgcc t 21

<210> SEQ ID NO 172
<211> LENGTH: 21
<212> TYPE: DNA
<213> ORGANISM: Klebsiella pneumoniae

<400> SEQUENCE: 172
aggcgatgag gttaataacc t 21

<210> SEQ ID NO 173
<211> LENGTH: 35
<212> TYPE: DNA
<213> ORGANISM: Klebsiella oxytoca

<400> SEQUENCE: 173
ggaagggata taggttatta acctcactcc cttcc 35

<210> SEQ ID NO 174
<211> LENGTH: 24
<212> TYPE: DNA
<213> ORGANISM: Klebsiella oxytoca

<400> SEQUENCE: 174
aggttattaa cctcactccc ttcc 24

<210> SEQ ID NO 175
<211> LENGTH: 24
<212> TYPE: DNA
<213> ORGANISM: Klebsiella oxytoca

<400> SEQUENCE: 175
ggaagggagt gaggttaata acct 24

<210> SEQ ID NO 176
<211> LENGTH: 32
<212> TYPE: DNA
<213> ORGANISM: Lactobacillus brevis

<400> SEQUENCE: 176
cgctcattca acggaagctc gttcgatgag cg 32

<210> SEQ ID NO 177
<211> LENGTH: 22
<212> TYPE: DNA
<213> ORGANISM: Lactobacillus brevis

<400> SEQUENCE: 177
tcattcaacg gaagctcgtt cg 22

<210> SEQ ID NO 178
<211> LENGTH: 22
<212> TYPE: DNA
<213> ORGANISM: Lactobacillus brevis

<400> SEQUENCE: 178
cgaacgagct tccgttgaat ga 22

<210> SEQ ID NO 179
<211> LENGTH: 37
<212> TYPE: DNA
<213> ORGANISM: Legionella pneumophila

<400> SEQUENCE: 179
tgccggatta tctgaccgtc ccaggttaat cccggca 37

<210> SEQ ID NO 180
<211> LENGTH: 18
<212> TYPE: DNA
<213> ORGANISM: Legionella pneumophila

<400> SEQUENCE: 180
atctgaccgt cccaggtt 18

<210> SEQ ID NO 181
<211> LENGTH: 18
<212> TYPE: DNA
<213> ORGANISM: Legionella pneumophila

<400> SEQUENCE: 181
aacctgggac ggtcagat 18

<210> SEQ ID NO 182
<211> LENGTH: 30
<212> TYPE: DNA
<213> ORGANISM: Listeria monocytogenes

<400> SEQUENCE: 182
acgctcataa gatgtggcgc atgcgagcgt 30

<210> SEQ ID NO 183
<211> LENGTH: 18
<212> TYPE: DNA
<213> ORGANISM: Listeria monocytogenes

<400> SEQUENCE: 183
ataagatgtg gcgcatgc 18

<210> SEQ ID NO 184
<211> LENGTH: 18
<212> TYPE: DNA
<213> ORGANISM: Listeria monocytogenes

<400> SEQUENCE: 184
gcatgcgcca catcttat 18

<210> SEQ ID NO 185
<211> LENGTH: 18
<212> TYPE: DNA
<213> ORGANISM: Mycoplasma hominis

<400> SEQUENCE: 185
attgctaacc tcgctcga 18

<210> SEQ ID NO 186
<211> LENGTH: 18
<212> TYPE: DNA
<213> ORGANISM: Mycoplasma hominis

<400> SEQUENCE: 186
tcgagcgagg ttagcaat 18

<210> SEQ ID NO 187
<211> LENGTH: 30
<212> TYPE: DNA
<213> ORGANISM: Proteus mirabilis

<400> SEQUENCE: 187
ggcgtcacac cggatacgta gtgctacgcc 30

<210> SEQ ID NO 188
<211> LENGTH: 18
<212> TYPE: DNA
<213> ORGANISM: Proteus mirabilis

<400> SEQUENCE: 188
ggcgtcacac cggatacg 18

<210> SEQ ID NO 189
<211> LENGTH: 19
<212> TYPE: DNA
<213> ORGANISM: Proteus mirabilis

<400> SEQUENCE: 189
ccgtatccgg tgtgacgcc 19

<210> SEQ ID NO 190
<211> LENGTH: 26
<212> TYPE: DNA
<213> ORGANISM: Pneumocystis

<400> SEQUENCE: 190
actcggcttc atgccaacag tcgagt 26

<210> SEQ ID NO 191
<211> LENGTH: 18
<212> TYPE: DNA
<213> ORGANISM: Pneumocystis

<400> SEQUENCE: 191
ggcttcatgc caacagtc 18

<210> SEQ ID NO 192
<211> LENGTH: 18
<212> TYPE: DNA
<213> ORGANISM: Pneumocystis

<400> SEQUENCE: 192
gactgttggc atgaagcc 18

<210> SEQ ID NO 193
<211> LENGTH: 28
<212> TYPE: DNA
<213> ORGANISM: Pneumocystis

<400> SEQUENCE: 193
gacaccataa gatgccgagc gaggtgtc 28

<210> SEQ ID NO 194
<211> LENGTH: 18
<212> TYPE: DNA
<213> ORGANISM: Pneumocystis

<400> SEQUENCE: 194
cataagatgc cgagcgag 18

<210> SEQ ID NO 195
<211> LENGTH: 18
<212> TYPE: DNA
<213> ORGANISM: Pneumocystis

<400> SEQUENCE: 195
ctcgctcggc atcttatg 18

<210> SEQ ID NO 196
<211> LENGTH: 43
<212> TYPE: DNA
<213> ORGANISM: Pseudomonas aeruginosa

<400> SEQUENCE: 196
accgccggcg taagacgact cgtcatcacc ttcgcccagc ggt 43

<210> SEQ ID NO 197
<211> LENGTH: 20
<212> TYPE: DNA
<213> ORGANISM: Pseudomonas aeruginosa

<400> SEQUENCE: 197
aagacgactc gtcatcacct 20

<210> SEQ ID NO 198
<211> LENGTH: 20
<212> TYPE: DNA
<213> ORGANISM: Pseudomonas aeruginosa

<400> SEQUENCE: 198
aggtgatgac gagtcgtctt 20

<210> SEQ ID NO 199
<211> LENGTH: 44
<212> TYPE: DNA
<213> ORGANISM: Pseudomonas sp.

<400> SEQUENCE: 199
gccgccggcg tggcagattc ctaggcatta cttcgcccag cggc 44

<210> SEQ ID NO 200
<211> LENGTH: 21
<212> TYPE: DNA
<213> ORGANISM: Pseudomonas sp.

<400> SEQUENCE: 200
ggcagattcc taggcattac t 21

<210> SEQ ID NO 201
<211> LENGTH: 21
<212> TYPE: DNA
<213> ORGANISM: Pseudomonas sp.

<400> SEQUENCE: 201
agtaatgcct aggaatctgc c 21

<210> SEQ ID NO 202
<211> LENGTH: 31
<212> TYPE: DNA
<213> ORGANISM: Salmonella

<400> SEQUENCE: 202
agctctgcgc ttttgtgtac ggggctgagc t 31

<210> SEQ ID NO 203
<211> LENGTH: 21
<212> TYPE: DNA
<213> ORGANISM: Salmonella

<400> SEQUENCE: 203
tgcgcttttg tgtacggggc t 21

<210> SEQ ID NO 204
<211> LENGTH: 21
<212> TYPE: DNA
<213> ORGANISM: Salmonella

<400> SEQUENCE: 204
agccccgtac acaaaagcgc a 21

<210> SEQ ID NO 205
<211> LENGTH: 19
<212> TYPE: DNA
<213> ORGANISM: Salmonella

<400> SEQUENCE: 205
gtgcatttgt gtacggggc 19

<210> SEQ ID NO 206
<211> LENGTH: 21
<212> TYPE: DNA
<213> ORGANISM: Salmonella

<400> SEQUENCE: 206
agccccgtac acaaaagcgc a 21

<210> SEQ ID NO 207
<211> LENGTH: 29
<212> TYPE: DNA
<213> ORGANISM: Salmonella

<400> SEQUENCE: 207
cgctccttca cctacgtgtc agcggagcg 29

<210> SEQ ID NO 208
<211> LENGTH: 19
<212> TYPE: DNA
<213> ORGANISM: Salmonella

<400> SEQUENCE: 208
cttcacctac gtgtcagcg 19

<210> SEQ ID NO 209
<211> LENGTH: 19
<212> TYPE: DNA
<213> ORGANISM: Salmonella

<400> SEQUENCE: 209
cgctgacacg taggtgaag 19

<210> SEQ ID NO 210
<211> LENGTH: 20
<212> TYPE: DNA
<213> ORGANISM: Salmonella

<400> SEQUENCE: 210
tcacctacat atcagcgtgc 20

<210> SEQ ID NO 211
<211> LENGTH: 20
<212> TYPE: DNA
<213> ORGANISM: Salmonella

<400> SEQUENCE: 211
cgctgacacg taggtgaaga 20

<210> SEQ ID NO 212
<211> LENGTH: 18
<212> TYPE: DNA
<213> ORGANISM: Salmonella

<400> SEQUENCE: 212
gtttacctgt gtgactgc 18

<210> SEQ ID NO 213
<211> LENGTH: 38
<212> TYPE: DNA
<213> ORGANISM: Salmonella

<400> SEQUENCE: 213
tgccggattc ttcacctacg tgtcagcgaa tcccggca 38

<210> SEQ ID NO 214
<211> LENGTH: 19
<212> TYPE: DNA
<213> ORGANISM: Salmonella

<400> SEQUENCE: 214
cttcacctac gtgtcagcg 19

<210> SEQ ID NO 215
<211> LENGTH: 19
<212> TYPE: DNA
<213> ORGANISM: Salmonella

<400> SEQUENCE: 215
cgctgacacg taggtgaag 19

<210> SEQ ID NO 216
<211> LENGTH: 43
<212> TYPE: DNA
<213> ORGANISM: Serratia marcescens

<400> SEQUENCE: 216
gccgccggcg tcgagactct agcttgccag ttcgcccagc ggc 43

<210> SEQ ID NO 217
<211> LENGTH: 20
<212> TYPE: DNA
<213> ORGANISM: Serratia marcescens

<400> SEQUENCE: 217
cgagactcta gcttgccagt 20

<210> SEQ ID NO 218
<211> LENGTH: 20
<212> TYPE: DNA
<213> ORGANISM: Serratia marcescens

<400> SEQUENCE: 218
actggcaagc tagagtctcg 20

<210> SEQ ID NO 219
<211> LENGTH: 43
<212> TYPE: DNA
<213> ORGANISM: Staphylococcus aureus

<400> SEQUENCE: 219
tgccggattt tctcgtccgt tcgctcgact tgcaatcccg gca 43

<210> SEQ ID NO 220
<211> LENGTH: 24
<212> TYPE: DNA
<213> ORGANISM: Staphylococcus aureus

<400> SEQUENCE: 220
ttctcgtccg ttcgctcgac ttgc 24

<210> SEQ ID NO 221
<211> LENGTH: 24
<212> TYPE: DNA
<213> ORGANISM: Staphylococcus aureus

<400> SEQUENCE: 221
gcaagtcgag cgaacggacg agaa 24

<210> SEQ ID NO 222
<211> LENGTH: 28
<212> TYPE: DNA
<213> ORGANISM: Staphylococcus

<400> SEQUENCE: 222
gcaactttcg cacatcagcg tcagttgc 28

<210> SEQ ID NO 223
<211> LENGTH: 21
<212> TYPE: DNA
<213> ORGANISM: Staphylococcus

<400> SEQUENCE: 223
tttcgcacat cagcgtcagt t 21

<210> SEQ ID NO 224
<211> LENGTH: 21
<212> TYPE: DNA
<213> ORGANISM: Staphylococcus

<400> SEQUENCE: 224
aactgacgct gatgtgcgaa a 21

<210> SEQ ID NO 225
<211> LENGTH: 30
<212> TYPE: DNA
<213> ORGANISM: Stenotrophomonas maltophilia

<400> SEQUENCE: 225
ccctctacca cactctagtc gggtagaggg 30

<210> SEQ ID NO 226
<211> LENGTH: 21
<212> TYPE: DNA
<213> ORGANISM: Stenotrophomonas maltophilia

<400> SEQUENCE: 226
ccctctacca cactctagtc g 21

<210> SEQ ID NO 227
<211> LENGTH: 21
<212> TYPE: DNA
<213> ORGANISM: Stenotrophomonas maltophilia

<400> SEQUENCE: 227
cgactagagt gtggtagagg g 21

<210> SEQ ID NO 228
<211> LENGTH: 44
<212> TYPE: DNA

<213> ORGANISM: Streptococcus agalactiae

<400> SEQUENCE: 228
gccgccggcg tactcctacc aacgttcttc tctcgcccag cggc 44

<210> SEQ ID NO 229
<211> LENGTH: 21
<212> TYPE: DNA
<213> ORGANISM: Streptococcus agalactiae

<400> SEQUENCE: 229
actcctacca acgttcttct c 21

<210> SEQ ID NO 230
<211> LENGTH: 21
<212> TYPE: DNA
<213> ORGANISM: Streptococcus agalactiae

<400> SEQUENCE: 230
gagaagaacg ttggtaggag t 21

<210> SEQ ID NO 231
<211> LENGTH: 35
<212> TYPE: DNA
<213> ORGANISM: Streptococcus

<400> SEQUENCE: 231
ggccttcgcc gtccctttct ggttagttga aggcc 35

<210> SEQ ID NO 232
<211> LENGTH: 21
<212> TYPE: DNA
<213> ORGANISM: Streptococcus

<400> SEQUENCE: 232
gccgtccctt tctggttagt t 21

<210> SEQ ID NO 233
<211> LENGTH: 21
<212> TYPE: DNA
<213> ORGANISM: Streptococcus

<400> SEQUENCE: 233
aactaaccag aaagggacgg c 21

<210> SEQ ID NO 234
<211> LENGTH: 36
<212> TYPE: DNA
<213> ORGANISM: Streptococcus pneumoniae

<400> SEQUENCE: 234
gcgttaagca aatgtcatgc aacatctact taacgc 36

<210> SEQ ID NO 235
<211> LENGTH: 25
<212> TYPE: DNA
<213> ORGANISM: Streptococcus pneumoniae

<400> SEQUENCE: 235
ttaagcaaat gtcatgcaac atcta 25

<210> SEQ ID NO 236
<211> LENGTH: 25

<212> TYPE: DNA
<213> ORGANISM: Streptococcus pneumoniae

<400> SEQUENCE: 236
tagatgttgc atgacatttg cttaa 25

<210> SEQ ID NO 237
<211> LENGTH: 38
<212> TYPE: DNA
<213> ORGANISM: Streptococcus pyogenes

<400> SEQUENCE: 237
tgccttcgag caattgcccc ttttaaatta cgaaggca 38

<210> SEQ ID NO 238
<211> LENGTH: 24
<212> TYPE: DNA
<213> ORGANISM: Streptococcus pyogenes

<400> SEQUENCE: 238
gagcaattgc ccctttttaaa ttac 24

<210> SEQ ID NO 239
<211> LENGTH: 24
<212> TYPE: DNA
<213> ORGANISM: Streptococcus pyogenes

<400> SEQUENCE: 239
gtaatttaaa aggggcaatt gctc 24

<210> SEQ ID NO 240
<211> LENGTH: 30
<212> TYPE: DNA
<213> ORGANISM: Ureaplasma urealyticum

<400> SEQUENCE: 240
acgctcgttc cccaactccc tactgagcgt 30

<210> SEQ ID NO 241
<211> LENGTH: 18
<212> TYPE: DNA
<213> ORGANISM: Ureaplasma urealyticum

<400> SEQUENCE: 241
gttccccaac tccctact 18

<210> SEQ ID NO 242
<211> LENGTH: 18
<212> TYPE: DNA
<213> ORGANISM: Ureaplasma urealyticum

<400> SEQUENCE: 242
agtagggagt tggggaac 18

<210> SEQ ID NO 243
<211> LENGTH: 26
<212> TYPE: DNA
<213> ORGANISM: Peptostreptococcus

<400> SEQUENCE: 243
actccccctt gtgtaaggca gggagt 26

<210> SEQ ID NO 244

<211> LENGTH: 18
<212> TYPE: DNA
<213> ORGANISM: Peptostreptococcus

<400> SEQUENCE: 244
ccccttgtgt aaggcagg 18

<210> SEQ ID NO 245
<211> LENGTH: 18
<212> TYPE: DNA
<213> ORGANISM: Peptostreptococcus

<400> SEQUENCE: 245
cctgccttac acaagggg 18

<210> SEQ ID NO 246
<211> LENGTH: 30
<212> TYPE: DNA
<213> ORGANISM: Yersinia enterocolitica

<400> SEQUENCE: 246
acgctcccca ctttggtccg aagagagcgt 30

<210> SEQ ID NO 247
<211> LENGTH: 18
<212> TYPE: DNA
<213> ORGANISM: Yersinia enterocolitica

<400> SEQUENCE: 247
cccactttgg tccgaaga 18

<210> SEQ ID NO 248
<211> LENGTH: 18
<212> TYPE: DNA
<213> ORGANISM: Yersinia enterocolitica

<400> SEQUENCE: 248
tcttcggacc aaagtggg 18

<210> SEQ ID NO 249
<211> LENGTH: 36
<212> TYPE: DNA
<213> ORGANISM: Acinetobacter sp.

<400> SEQUENCE: 249
tgccggtttt aggccagatg gctgccaatc ccggca 36

<210> SEQ ID NO 250
<211> LENGTH: 28
<212> TYPE: DNA
<213> ORGANISM: Aspergillus fumigatus

<400> SEQUENCE: 250
ccggcccccg agaggtgata catgccgg 28

<210> SEQ ID NO 251
<211> LENGTH: 31
<212> TYPE: DNA
<213> ORGANISM: Aspergillus niger

<400> SEQUENCE: 251
ccggcaatta caatgcggac tccgaagccg g 31

<210> SEQ ID NO 252
<211> LENGTH: 42
<212> TYPE: DNA
<213> ORGANISM: Klebsiella pneumoniae

<400> SEQUENCE: 252
acgccggcgt aggttattaa cctcatcgcc ttcgcccagc gt 42

<210> SEQ ID NO 253
<211> LENGTH: 29
<212> TYPE: DNA
<213> ORGANISM: Mycobacterium avium

<400> SEQUENCE: 253
cccggtgttg atataaggca ggtgccggg 29

<210> SEQ ID NO 254
<211> LENGTH: 30
<212> TYPE: DNA
<213> ORGANISM: Mycobacterium chelonae

<400> SEQUENCE: 254
cccggcatga agtgtgtggt cctatccggg 30

<210> SEQ ID NO 255
<211> LENGTH: 30
<212> TYPE: DNA
<213> ORGANISM: Mycobacterium fortuitum

<400> SEQUENCE: 255
cccggtgaag cgcgtggtca tattcccggg 30

<210> SEQ ID NO 256
<211> LENGTH: 30
<212> TYPE: DNA
<213> ORGANISM: Mycobacterium gordonae

<400> SEQUENCE: 256
cccggtgtgt cctgtggtcc tattcccggg 30

<210> SEQ ID NO 257
<211> LENGTH: 30
<212> TYPE: DNA
<213> ORGANISM: Mycobacterium intracellulare

<400> SEQUENCE: 257
cccggacatg cgtctaaagg tcctaccggg 30

<210> SEQ ID NO 258
<211> LENGTH: 30
<212> TYPE: DNA
<213> ORGANISM: Mycobacterium kansasii

<400> SEQUENCE: 258
cccggtagag ctgagacgta tcgatccggg 30

<210> SEQ ID NO 259
<211> LENGTH: 28
<212> TYPE: DNA
<213> ORGANISM: Mycobacterium malmoense

<400> SEQUENCE: 259
ccgcgccact gaaacgccct attcgcgg 28

<210> SEQ ID NO 260
<211> LENGTH: 28
<212> TYPE: DNA
<213> ORGANISM: Mycobacterium smegmatis

<400> SEQUENCE: 260
cccggcacgt cgagggctct gacccggg 28

<210> SEQ ID NO 261
<211> LENGTH: 24
<212> TYPE: DNA
<213> ORGANISM: Mycobacterium tuberculosis

<400> SEQUENCE: 261
ccaccggaga ggaaaaggag gtgg 24

<210> SEQ ID NO 262
<211> LENGTH: 27
<212> TYPE: DNA
<213> ORGANISM: Mycobacterium xenopi

<400> SEQUENCE: 262
ccgcgccgct accaaacgct ttcgcgg 27

<210> SEQ ID NO 263
<211> LENGTH: 30
<212> TYPE: DNA
<213> ORGANISM: Shigella

<400> SEQUENCE: 263
ccgggtcacc ctgtatcgca cgcctcccgg 30

<210> SEQ ID NO 264
<211> LENGTH: 43
<212> TYPE: DNA
<213> ORGANISM: Staphylococcus aureus

<400> SEQUENCE: 264
tgccggattt tctcgtccgt tcgctcgact tgcaatcccg gca 43

<210> SEQ ID NO 265
<211> LENGTH: 44
<212> TYPE: DNA
<213> ORGANISM: Streptococcus agalactiae

<400> SEQUENCE: 265
gccgccggcg tactcctacc aacgttcttc tctcgcccag cggc 44

<210> SEQ ID NO 266
<211> LENGTH: 38
<212> TYPE: DNA
<213> ORGANISM: Streptococcus pyogenes

<400> SEQUENCE: 266
tgccttcgag caattgcccc ttttaaatta cgaaggca 38

<210> SEQ ID NO 267
<211> LENGTH: 34
<212> TYPE: DNA
<213> ORGANISM: Citrobacter freundii

<400> SEQUENCE: 267
cccggtcgct tcattacgct atgtatccac cggg 34

<210> SEQ ID NO 268
<211> LENGTH: 34
<212> TYPE: DNA
<213> ORGANISM: Streptococcus pyogenes

<400> SEQUENCE: 268
cgctcgagca attgcccctt ttaaattacg agcg 34

<210> SEQ ID NO 269
<211> LENGTH: 36
<212> TYPE: DNA
<213> ORGANISM: Streptococcus pneumoniae

<400> SEQUENCE: 269
ccgttaagca aatgtcatgc aacatctact taacgg 36

<210> SEQ ID NO 270
<211> LENGTH: 35
<212> TYPE: DNA
<213> ORGANISM: Streptococcus

<400> SEQUENCE: 270
cgccttcgcc gtccctttct ggttagttga aggcg 35

<210> SEQ ID NO 271
<211> LENGTH: 31
<212> TYPE: DNA
<213> ORGANISM: Streptococcus agalactiae

<400> SEQUENCE: 271
ccgctactcc taccaacgtt cttctcagcg g 31

<210> SEQ ID NO 272
<211> LENGTH: 32
<212> TYPE: DNA
<213> ORGANISM: Serratia marcescens

<400> SEQUENCE: 272
ccgctccgag actctagctt gccagtgagc gg 32

<210> SEQ ID NO 273
<211> LENGTH: 31
<212> TYPE: DNA
<213> ORGANISM: Pseudomonas sp.

<400> SEQUENCE: 273
cgctcggcag attcctaggc attactgagc g 31

<210> SEQ ID NO 274
<211> LENGTH: 28
<212> TYPE: DNA
<213> ORGANISM: Staphylococcus

<400> SEQUENCE: 274
ccaactttcg cacatcagcg tcagttgg 28

<210> SEQ ID NO 275
<211> LENGTH: 29
<212> TYPE: DNA
<213> ORGANISM: Salmonella

<400> SEQUENCE: 275
cgctccttca cctacgtgtc agcggagcg 29

<210> SEQ ID NO 276
<211> LENGTH: 30
<212> TYPE: DNA
<213> ORGANISM: Pseudomonas aeruginosa

<400> SEQUENCE: 276
cccggaagac gactcgtcat cagctccggg 30

<210> SEQ ID NO 277
<211> LENGTH: 26
<212> TYPE: DNA
<213> ORGANISM: Legionella pneumophila

<400> SEQUENCE: 277
ccggatctga ccgtcccagg ttccgg 26

<210> SEQ ID NO 278
<211> LENGTH: 35
<212> TYPE: DNA
<213> ORGANISM: Klebsiella oxytoca

<400> SEQUENCE: 278
ccgaggtagg ttattaacct cactcccttc ctcgg 35

<210> SEQ ID NO 279
<211> LENGTH: 29
<212> TYPE: DNA
<213> ORGANISM: Staphylococcus aureus

<400> SEQUENCE: 279
cccctcaagc ttctcgtccg ttcgagggg 29

<210> SEQ ID NO 280
<211> LENGTH: 30
<212> TYPE: DNA
<213> ORGANISM: Listeria monocytogenes

<400> SEQUENCE: 280
cctagcatgc gccacatctt atcagctagg 30

<210> SEQ ID NO 281
<211> LENGTH: 29
<212> TYPE: DNA
<213> ORGANISM: Klebsiella pneumoniae

<400> SEQUENCE: 281
caggcttagg ttattaacct catcgcctg 29

<210> SEQ ID NO 282
<211> LENGTH: 30
<212> TYPE: DNA
<213> ORGANISM: Haemophilus influenzae

<400> SEQUENCE: 282
cccggccgca ctttcatctt ccgatccggg 30

<210> SEQ ID NO 283
<211> LENGTH: 30
<212> TYPE: DNA
<213> ORGANISM: Burkholderia sp.

<400> SEQUENCE: 283
cccggccagt caccaatgca gttccccggg 30

<210> SEQ ID NO 284
<211> LENGTH: 27
<212> TYPE: DNA
<213> ORGANISM: Burkholderia cepacia

<400> SEQUENCE: 284
cctgcctatg tattcagcca tggcagg 27

<210> SEQ ID NO 285
<211> LENGTH: 29
<212> TYPE: DNA
<213> ORGANISM: Burkholderia mallei

<400> SEQUENCE: 285
gggcctcgcc tcactagacc tatgccggg 29

<210> SEQ ID NO 286
<211> LENGTH: 29
<212> TYPE: DNA
<213> ORGANISM: Burkholderia vietnamensis

<400> SEQUENCE: 286
cccggtcgct tctctggacc tatgccggg 29

<210> SEQ ID NO 287
<211> LENGTH: 28
<212> TYPE: DNA
<213> ORGANISM: Burkholderia multivorans

<400> SEQUENCE: 287
cccggcttca cccttccagc gcaccggg 28

<210> SEQ ID NO 288
<211> LENGTH: 30
<212> TYPE: DNA
<213> ORGANISM: Burkholderia gladioli

<400> SEQUENCE: 288
ccagcggtac ggtcactgtt aaactgctgg 30

<210> SEQ ID NO 289
<211> LENGTH: 30
<212> TYPE: DNA
<213> ORGANISM: Acinetobacter sp.

<400> SEQUENCE: 289
ccgtagacca tcctctccca tactctacgg 30

<210> SEQ ID NO 290
<211> LENGTH: 23
<212> TYPE: DNA
<213> ORGANISM: Acinetobacter baumannii

<400> SEQUENCE: 290
ccgctaggtc cggtagcaag cgg 23

<210> SEQ ID NO 291
<211> LENGTH: 28
<212> TYPE: DNA
<213> ORGANISM: Aspergillus flavus

<400> SEQUENCE: 291
cggcctacat tccgggagcc tttggccg 28

<210> SEQ ID NO 292
<211> LENGTH: 29
<212> TYPE: DNA
<213> ORGANISM: Aspergillus terreus

<400> SEQUENCE: 292
ccgatcagac accccgcccc atagatcgg 29

<210> SEQ ID NO 293
<211> LENGTH: 31
<212> TYPE: DNA
<213> ORGANISM: Bacteroides

<400> SEQUENCE: 293
ccgcggtgtc tcagttccaa tgtgggcgcg g 31

<210> SEQ ID NO 294
<211> LENGTH: 32
<212> TYPE: DNA
<213> ORGANISM: Borrelia burgdorferi

<400> SEQUENCE: 294
cccggggtaa cagataacaa gggttgcccg gg 32

<210> SEQ ID NO 295
<211> LENGTH: 29
<212> TYPE: DNA
<213> ORGANISM: Bordetella pertussis

<400> SEQUENCE: 295
ccgggctccc cacactttcg tgcacccgg 29

<210> SEQ ID NO 296
<211> LENGTH: 28
<212> TYPE: DNA
<213> ORGANISM: Escherichia coli

<400> SEQUENCE: 296
ccggcaaaga agcaagcttc ttccccgg 28

<210> SEQ ID NO 297
<211> LENGTH: 30
<212> TYPE: DNA
<213> ORGANISM: Gardnerella vaginalis

<400> SEQUENCE: 297
ccgctccacc atgaagcaac ccgtgagcgg 30

<210> SEQ ID NO 298
<211> LENGTH: 29
<212> TYPE: DNA
<213> ORGANISM: Unknown
<220> FEATURE:
<223> OTHER INFORMATION: Bacteria

<400> SEQUENCE: 298
ccgcgtgctg cctcccgtag gagtcgcgg 29

<210> SEQ ID NO 299
<211> LENGTH: 33

<212> TYPE: DNA
<213> ORGANISM: Enterococcus faecium

<400> SEQUENCE: 299
cttcaaatca aaaccatgcg gtttcatttg aag 33

<210> SEQ ID NO 300
<211> LENGTH: 32
<212> TYPE: DNA
<213> ORGANISM: Stenotrophomonas maltophilia

<400> SEQUENCE: 300
cccggaccct ctaccacact ctagtcgccg gg 32

<210> SEQ ID NO 301
<211> LENGTH: 25
<212> TYPE: DNA
<213> ORGANISM: Enterococcus faecalis

<400> SEQUENCE: 301
caaccaccct ctgatgggta ggttg 25

<210> SEQ ID NO 302
<211> LENGTH: 29
<212> TYPE: DNA
<213> ORGANISM: Enterococcus

<400> SEQUENCE: 302
cccggcatcc atcagcgaca cccgccggg 29

<210> SEQ ID NO 303
<211> LENGTH: 28
<212> TYPE: DNA
<213> ORGANISM: Unknown
<220> FEATURE:
<223> OTHER INFORMATION: Enterobacteriaceae

<400> SEQUENCE: 303
cccggtctcg cgaggtcgct tctccggg 28

<210> SEQ ID NO 304
<211> LENGTH: 31
<212> TYPE: DNA
<213> ORGANISM: Clostridium perfringens

<400> SEQUENCE: 304
gcatcagatt gctcctttgg ttgaatgatg c 31

<210> SEQ ID NO 305
<211> LENGTH: 28
<212> TYPE: DNA
<213> ORGANISM: Clostridium sp.

<400> SEQUENCE: 305
cccggtaccg tcattatcgt cccccggg 28

<210> SEQ ID NO 306
<211> LENGTH: 25
<212> TYPE: DNA
<213> ORGANISM: Chlamydia trachomatis

<400> SEQUENCE: 306
ccgctcggat gcccaaatat cgcgg 25

<210> SEQ ID NO 307
<211> LENGTH: 32
<212> TYPE: DNA
<213> ORGANISM: Candida dubliniensis

<400> SEQUENCE: 307
cccggcccga aagagtaact tgcaaaaccg gg 32

<210> SEQ ID NO 308
<211> LENGTH: 27
<212> TYPE: DNA
<213> ORGANISM: Candida glabrata

<400> SEQUENCE: 308
cccggaggca aggggcgcaa aaccggg 27

<210> SEQ ID NO 309
<211> LENGTH: 29
<212> TYPE: DNA
<213> ORGANISM: Candida krusei

<400> SEQUENCE: 309
ccgtgacctg cagcaagaac cgatcacgg 29

<210> SEQ ID NO 310
<211> LENGTH: 29
<212> TYPE: DNA
<213> ORGANISM: Candida lusitaniae

<400> SEQUENCE: 310
cactgccgac tcagaccacg aaagcagtg 29

<210> SEQ ID NO 311
<211> LENGTH: 30
<212> TYPE: DNA
<213> ORGANISM: Candida albicans

<400> SEQUENCE: 311
ccgcgtttac acagacccgg gtcatcgcgg 30

<210> SEQ ID NO 312
<211> LENGTH: 34
<212> TYPE: DNA
<213> ORGANISM: Candida tropicalis

<400> SEQUENCE: 312
cctcggacat tccaacgcaa ttctcctacc gagg 34

<210> SEQ ID NO 313
<211> LENGTH: 34
<212> TYPE: DNA
<213> ORGANISM: Candida parapsilosis

<400> SEQUENCE: 313
cccggcacat ttctttgcac ttatcctacc cggg 34

<210> SEQ ID NO 314
<211> LENGTH: 30
<212> TYPE: DNA
<213> ORGANISM: Chlamydia pneumoniae

<400> SEQUENCE: 314
ccgggctctt cctcaaccga aaggtcccgg 30

<210> SEQ ID NO 315
<211> LENGTH: 28
<212> TYPE: DNA
<213> ORGANISM: Chlamydia psittaci

<400> SEQUENCE: 315
ccggaaggca aaaccaactc ccatccgg 28

<210> SEQ ID NO 316
<211> LENGTH: 28
<212> TYPE: DNA
<213> ORGANISM: Campylobacter

<400> SEQUENCE: 316
cccgggccct aagcgtcctt ccaccggg 28

<210> SEQ ID NO 317
<211> LENGTH: 28
<212> TYPE: DNA
<213> ORGANISM: Campylobacter coli

<400> SEQUENCE: 317
cgctctcgat ggcatcaggg gttgagcg 28

<210> SEQ ID NO 318
<211> LENGTH: 34
<212> TYPE: DNA
<213> ORGANISM: Campylobacter lari

<400> SEQUENCE: 318
cccggcccga agtgttagca actaaatcgc cggg 34

<210> SEQ ID NO 319
<211> LENGTH: 33
<212> TYPE: DNA
<213> ORGANISM: Campylobacter jejuni

<400> SEQUENCE: 319
ccgggtaagc taaccacacc ttataccgcc cgg 33

<210> SEQ ID NO 320
<211> LENGTH: 34
<212> TYPE: DNA
<213> ORGANISM: Campylobacter upsaliensis

<400> SEQUENCE: 320
cccgggccgt gtgtcgccct aggcgtagcc cggg 34

<210> SEQ ID NO 321
<211> LENGTH: 33
<212> TYPE: DNA
<213> ORGANISM: Pneumocystis carinii

<400> SEQUENCE: 321
ccctgctatc cagtaactga aaccgatgca ggg 33

<210> SEQ ID NO 322
<211> LENGTH: 32
<212> TYPE: DNA
<213> ORGANISM: Mycoplasma pneumoniae

<400> SEQUENCE: 322
cctccgtgat agctgtttcc aactaccgga gg 32

<210> SEQ ID NO 323
<211> LENGTH: 29
<212> TYPE: DNA
<213> ORGANISM: Cryptococcus neoformans

<400> SEQUENCE: 323
cctggtatga ttcaccatag agggccagg 29

<210> SEQ ID NO 324
<211> LENGTH: 29
<212> TYPE: DNA
<213> ORGANISM: Escherichia coli

<400> SEQUENCE: 324
cccggtcacc ccataaaaga ggctccggg 29

<210> SEQ ID NO 325
<211> LENGTH: 25
<212> TYPE: DNA
<213> ORGANISM: Neisseria meningitidis

<400> SEQUENCE: 325
caccgttatc ccccactact cggtg 25

<210> SEQ ID NO 326
<211> LENGTH: 28
<212> TYPE: DNA
<213> ORGANISM: Neisseria gonorrhoeae

<400> SEQUENCE: 326
cccggacccc gccaaccagc taaccggg 28

<210> SEQ ID NO 327
<211> LENGTH: 32
<212> TYPE: DNA
<213> ORGANISM: Clostridium difficile

<400> SEQUENCE: 327
cgggtcgaag taaatcgctc aacttgcacc cg 32

<210> SEQ ID NO 328
<211> LENGTH: 28
<212> TYPE: DNA
<213> ORGANISM: Clostridium botulinum

<400> SEQUENCE: 328
cgttgccgtt tcatgcgaaa ctacaacg 28

<210> SEQ ID NO 329
<211> LENGTH: 27
<212> TYPE: DNA
<213> ORGANISM: Clostridium tetani

<400> SEQUENCE: 329
ccggaactgt gttactcacc cgtccgg 27

<210> SEQ ID NO 330
<211> LENGTH: 28
<212> TYPE: DNA
<213> ORGANISM: Peptostreptococcus anaerobius

<400> SEQUENCE: 330
ccggcctttg atatatctac gatgccgg 28

<210> SEQ ID NO 331
<211> LENGTH: 28
<212> TYPE: DNA
<213> ORGANISM: Peptostreptococcus magnus

<400> SEQUENCE: 331
ccgcctaatc cgaaatgaat tctggcgg 28

<210> SEQ ID NO 332
<211> LENGTH: 32
<212> TYPE: DNA
<213> ORGANISM: Peptostreptococcus magnus

<400> SEQUENCE: 332
ccgccatgtg tttctacgat tttatgcggc gg 32

<210> SEQ ID NO 333
<211> LENGTH: 31
<212> TYPE: DNA
<213> ORGANISM: Peptostreptococcus micros

<400> SEQUENCE: 333
cccggacttt catttcattt ccattcccgg g 31

<210> SEQ ID NO 334
<211> LENGTH: 31
<212> TYPE: DNA
<213> ORGANISM: Enterococcus faecalis

<400> SEQUENCE: 334
ccatcggcac tcgggaggaa agaagcgatg g 31

<210> SEQ ID NO 335
<211> LENGTH: 31
<212> TYPE: DNA
<213> ORGANISM: Enterococcus faecium

<400> SEQUENCE: 335
cgcccatgcg gttttgattg ttatacgggc g 31

<210> SEQ ID NO 336
<211> LENGTH: 32
<212> TYPE: DNA
<213> ORGANISM: Enterococcus casseliflavus

<400> SEQUENCE: 336
ccgcgcaagg gacgaacatt ttactctcgc gg 32

<210> SEQ ID NO 337
<211> LENGTH: 30
<212> TYPE: DNA
<213> ORGANISM: Enterococcus gallinarum

<400> SEQUENCE: 337
ccgcgcaagg gatgaacgtt ctactcgcgg 30

<210> SEQ ID NO 338
<211> LENGTH: 30
<212> TYPE: DNA
<213> ORGANISM: Candida albicans

<400> SEQUENCE: 338
cccggtttcc ttctgggtag ccattccggg 30

<210> SEQ ID NO 339
<211> LENGTH: 32
<212> TYPE: DNA
<213> ORGANISM: Morganella morganii

<400> SEQUENCE: 339
ccggcaagac tctagctgac cagtatcgcc gg 32

<210> SEQ ID NO 340
<211> LENGTH: 28
<212> TYPE: DNA
<213> ORGANISM: Proteus mirabilis

<400> SEQUENCE: 340
cgccgatagt gcaaggtccg aagcggcg 28

<210> SEQ ID NO 341
<211> LENGTH: 27
<212> TYPE: DNA
<213> ORGANISM: Proteus vulgaris

<400> SEQUENCE: 341
ccgccgtaga cgtcatgcgg taggcgg 27

<210> SEQ ID NO 342
<211> LENGTH: 30
<212> TYPE: DNA
<213> ORGANISM: Treponema pallidum

<400> SEQUENCE: 342
cccggtccgc cactctagag aaacgccggg 30

<210> SEQ ID NO 343
<211> LENGTH: 30
<212> TYPE: DNA
<213> ORGANISM: Trichonomas vaginalis

<400> SEQUENCE: 343
cccgggaatg gcgtgcctct gatgaccggg 30

<210> SEQ ID NO 344
<211> LENGTH: 27
<212> TYPE: DNA
<213> ORGANISM: Micrococcus

<400> SEQUENCE: 344
cccggacctc acagtatcgc aaccggg 27

<210> SEQ ID NO 345
<211> LENGTH: 26
<212> TYPE: DNA
<213> ORGANISM: Lactobacillus brevis

<400> SEQUENCE: 345
cggccgcggg atcatccaga aggccg 26

<210> SEQ ID NO 346
<211> LENGTH: 33
<212> TYPE: DNA
<213> ORGANISM: Yersinia enterocolitica

<400> SEQUENCE: 346
cccggatctc tgctaaattc cgtggatgcc ggg 33

<210> SEQ ID NO 347
<211> LENGTH: 28
<212> TYPE: DNA
<213> ORGANISM: Bacillus cereus

<400> SEQUENCE: 347
ccataccact ctgctcccga aggtatgg 28

<210> SEQ ID NO 348
<211> LENGTH: 30
<212> TYPE: DNA
<213> ORGANISM: Vibrio cholerae

<400> SEQUENCE: 348
ctgatgcata tccggtagcg caagcatcag 30

<210> SEQ ID NO 349
<211> LENGTH: 32
<212> TYPE: DNA
<213> ORGANISM: Vibrio parahaemolyticus

<400> SEQUENCE: 349
cccggtgcag ctattaacta cactaccccg gg 32

<210> SEQ ID NO 350
<211> LENGTH: 32
<212> TYPE: DNA
<213> ORGANISM: Cryptosporidium sp.

<400> SEQUENCE: 350
ccgtacataa ggtgctgaag gagtaagtac gg 32

<210> SEQ ID NO 351
<211> LENGTH: 28
<212> TYPE: DNA
<213> ORGANISM: Coxiella burnetii

<400> SEQUENCE: 351
ccgggaccct tgagaatttc ttccccgg 28

<210> SEQ ID NO 352
<211> LENGTH: 32
<212> TYPE: DNA
<213> ORGANISM: Bartonella sp.

<400> SEQUENCE: 352
ccggcacaaa tttctctgtg ttattccgcc gg 32

<210> SEQ ID NO 353
<211> LENGTH: 32
<212> TYPE: DNA
<213> ORGANISM: Enterobacter sakazakii

<400> SEQUENCE: 353
cccggtctct gcaggattct ctggatgccg gg 32

<210> SEQ ID NO 354
<211> LENGTH: 30
<212> TYPE: DNA

<213> ORGANISM: Ehrlichia sp.

<400> SEQUENCE: 354
ccgcgctaat ctaacgtagg ctcatcgcgg 30

<210> SEQ ID NO 355
<211> LENGTH: 32
<212> TYPE: DNA
<213> ORGANISM: Rickettsia sp.

<400> SEQUENCE: 355
ccgcgcactc actcggtatt gctggatcgc gg 32

<210> SEQ ID NO 356
<211> LENGTH: 27
<212> TYPE: DNA
<213> ORGANISM: Rickettsia

<400> SEQUENCE: 356
ctagccccaa ttagtccgtt cggctag 27

<210> SEQ ID NO 357
<211> LENGTH: 29
<212> TYPE: DNA
<213> ORGANISM: Rickettsia typhi

<400> SEQUENCE: 357
cgcccgtctg ccactaatta actagggcg 29

<210> SEQ ID NO 358
<211> LENGTH: 24
<212> TYPE: DNA
<213> ORGANISM: Leishmania sp.

<400> SEQUENCE: 358
cccggaaaag gcgttacggc cggg 24

<210> SEQ ID NO 359
<211> LENGTH: 27
<212> TYPE: DNA
<213> ORGANISM: Toxoplasma gondii

<400> SEQUENCE: 359
ccggctccag gggaagaggc atgccgg 27

<210> SEQ ID NO 360
<211> LENGTH: 34
<212> TYPE: DNA
<213> ORGANISM: Saccharomycotina

<400> SEQUENCE: 360
cccgggtatt tacattgtac tcattccaac cggg 34

<210> SEQ ID NO 361
<211> LENGTH: 28
<212> TYPE: DNA
<213> ORGANISM: Francisella tularensis

<400> SEQUENCE: 361
ccatgcgaca gcccgaaagc cagcatgg 28

<210> SEQ ID NO 362
<211> LENGTH: 28

<212> TYPE: DNA
<213> ORGANISM: Lactobacillus sp.

<400> SEQUENCE: 362
cccggagttc cactgtcctc ttcccggg 28

<210> SEQ ID NO 363
<211> LENGTH: 28
<212> TYPE: DNA
<213> ORGANISM: Lactobacillus sp.

<400> SEQUENCE: 363
cccggatcag tctctcaact cggccggg 28

<210> SEQ ID NO 364
<211> LENGTH: 28
<212> TYPE: DNA
<213> ORGANISM: Burkholderia cepacia

<400> SEQUENCE: 364
cccggttggc aaccctctgt tccccggg 28

<210> SEQ ID NO 365
<211> LENGTH: 27
<212> TYPE: DNA
<213> ORGANISM: Staphylococcus aureus

<400> SEQUENCE: 365
cctgcaagct tctcgtccgt tcgcagg 27

<210> SEQ ID NO 366
<211> LENGTH: 29
<212> TYPE: DNA
<213> ORGANISM: Staphylococcus aureus

<400> SEQUENCE: 366
cccctcaagc ttctcgtccg ttcgagggg 29

<210> SEQ ID NO 367
<211> LENGTH: 29
<212> TYPE: DNA
<213> ORGANISM: Unknown
<220> FEATURE:
<223> OTHER INFORMATION: Bacteria

<400> SEQUENCE: 367
ccgcgtgctg cctcccgtag gagtcgcgg 29

<210> SEQ ID NO 368
<211> LENGTH: 29
<212> TYPE: DNA
<213> ORGANISM: Unknown
<220> FEATURE:
<223> OTHER INFORMATION: Bacteria

<400> SEQUENCE: 368
ccgcgtgctg cctcccgtag gagtcgcgg 29

<210> SEQ ID NO 369
<211> LENGTH: 29
<212> TYPE: DNA
<213> ORGANISM: Unknown
<220> FEATURE:
<223> OTHER INFORMATION: Bacteria

<400> SEQUENCE: 369
ccgcgtgctg cctcccgtag gagtcgcgg 29

<210> SEQ ID NO 370
<211> LENGTH: 29
<212> TYPE: DNA
<213> ORGANISM: Unknown
<220> FEATURE:
<223> OTHER INFORMATION: Bacteria

<400> SEQUENCE: 370
ccgcgtgctg cctcccgtag gagtcgcgg 29

<210> SEQ ID NO 371
<211> LENGTH: 21
<212> TYPE: DNA
<213> ORGANISM: Achromobacter xylosoxidans

<400> SEQUENCE: 371
tccaatagtg caaggtcttg c 21

<210> SEQ ID NO 372
<211> LENGTH: 26
<212> TYPE: DNA
<213> ORGANISM: Acinetobacter baumannii

<400> SEQUENCE: 372
ttcacatccg acttaataag ccgcct 26

<210> SEQ ID NO 373
<211> LENGTH: 21
<212> TYPE: DNA
<213> ORGANISM: Acinetobacter sp.

<400> SEQUENCE: 373
accatcctct cccatactct a 21

<210> SEQ ID NO 374
<211> LENGTH: 25
<212> TYPE: DNA
<213> ORGANISM: Bacillus cereus

<400> SEQUENCE: 374
tgcggttcaa aatgttatcc ggtat 25

<210> SEQ ID NO 375
<211> LENGTH: 21
<212> TYPE: DNA
<213> ORGANISM: Bacteroides

<400> SEQUENCE: 375
gtgtctcagt tccaatgtgg g 21

<210> SEQ ID NO 376
<211> LENGTH: 20
<212> TYPE: DNA
<213> ORGANISM: Burkholderia cepacia

<400> SEQUENCE: 376
ggttggcaac cctctgttcc 20

<210> SEQ ID NO 377
<211> LENGTH: 18

<212> TYPE: DNA
<213> ORGANISM: Campylobacter

<400> SEQUENCE: 377
gccctaagcg tccttcca 18

<210> SEQ ID NO 378
<211> LENGTH: 21
<212> TYPE: DNA
<213> ORGANISM: Citrobacter freundii

<400> SEQUENCE: 378
gccagtttcg gatgcagttc c 21

<210> SEQ ID NO 379
<211> LENGTH: 23
<212> TYPE: DNA
<213> ORGANISM: Clostridium difficile

<400> SEQUENCE: 379
cgaagtaaat cgctcaactt gca 23

<210> SEQ ID NO 380
<211> LENGTH: 21
<212> TYPE: DNA
<213> ORGANISM: Clostridium perfringens

<400> SEQUENCE: 380
gaggtgttga aacccccaca c 21

<210> SEQ ID NO 381
<211> LENGTH: 22
<212> TYPE: DNA
<213> ORGANISM: Clostridium sp.

<400> SEQUENCE: 381
cctttacgcc cagtaaatcc gg 22

<210> SEQ ID NO 382
<211> LENGTH: 20
<212> TYPE: DNA
<213> ORGANISM: Corynebacterium sp.

<400> SEQUENCE: 382
cccggaattt cacagacgac 20

<210> SEQ ID NO 383
<211> LENGTH: 20
<212> TYPE: DNA
<213> ORGANISM: Corynebacterium sp.

<400> SEQUENCE: 383
cccggaattt cacagacgac 20

<210> SEQ ID NO 384
<211> LENGTH: 27
<212> TYPE: DNA
<213> ORGANISM: Escherichia coli

<400> SEQUENCE: 384
caatgagcaa aggtattaac tttactc 27

<210> SEQ ID NO 385

<211> LENGTH: 22
<212> TYPE: DNA
<213> ORGANISM: Escherichia coli

<400> SEQUENCE: 385
agtcacacag attgctctgt gc 22

<210> SEQ ID NO 386
<211> LENGTH: 22
<212> TYPE: DNA
<213> ORGANISM: Enterobacter aerogenes

<400> SEQUENCE: 386
aagactctag cctgccagtt tc 22

<210> SEQ ID NO 387
<211> LENGTH: 19
<212> TYPE: DNA
<213> ORGANISM: Enterobacter sakazakii

<400> SEQUENCE: 387
ctcccgcatc tctgcagga 19

<210> SEQ ID NO 388
<211> LENGTH: 19
<212> TYPE: DNA
<213> ORGANISM: Enterobacter sakazakii

<400> SEQUENCE: 388
ctcccgcatc tctgcagga 19

<210> SEQ ID NO 389
<211> LENGTH: 23
<212> TYPE: DNA
<213> ORGANISM: Unknown
<220> FEATURE:
<223> OTHER INFORMATION: Enterobacteriaceae

<400> SEQUENCE: 389
accgtttcca gtagttatcc ccc 23

<210> SEQ ID NO 390
<211> LENGTH: 20
<212> TYPE: DNA
<213> ORGANISM: Enterococcus

<400> SEQUENCE: 390
ccatcagcga cacccgaaag 20

<210> SEQ ID NO 391
<211> LENGTH: 24
<212> TYPE: DNA
<213> ORGANISM: Enterococcus

<400> SEQUENCE: 391
ttaagaaacc gcctgcgctc gctt 24

<210> SEQ ID NO 392
<211> LENGTH: 19
<212> TYPE: DNA
<213> ORGANISM: Enterococcus faecalis

<400> SEQUENCE: 392
gcactcggga ggaaagaag 19

<210> SEQ ID NO 393
<211> LENGTH: 25
<212> TYPE: DNA
<213> ORGANISM: Enterococcus faecium

<400> SEQUENCE: 393
gcgcctttca aatcaaaacc atgcg 25

<210> SEQ ID NO 394
<211> LENGTH: 25
<212> TYPE: DNA
<213> ORGANISM: Escherichia coli

<400> SEQUENCE: 394
gagcaagtcg cttcacctac atatc 25

<210> SEQ ID NO 395
<211> LENGTH: 20
<212> TYPE: DNA
<213> ORGANISM: Haemophilus influenzae

<400> SEQUENCE: 395
ccgcactttc atcttccgat 20

<210> SEQ ID NO 396
<211> LENGTH: 19
<212> TYPE: DNA
<213> ORGANISM: Inquilinus limosus

<400> SEQUENCE: 396
cttggattca agcccgccc 19

<210> SEQ ID NO 397
<211> LENGTH: 18
<212> TYPE: DNA
<213> ORGANISM: Klebsiella pneumoniae

<400> SEQUENCE: 397
gtcacacccg aaggtgct 18

<210> SEQ ID NO 398
<211> LENGTH: 23
<212> TYPE: DNA
<213> ORGANISM: Klebsiella oxytoca

<400> SEQUENCE: 398
ccatgagcaa gtcacttcac tta 23

<210> SEQ ID NO 399
<211> LENGTH: 18
<212> TYPE: DNA
<213> ORGANISM: Klebsiella pneumoniae

<400> SEQUENCE: 399
gtcacacccg aaggtgct 18

<210> SEQ ID NO 400
<211> LENGTH: 25
<212> TYPE: DNA
<213> ORGANISM: Klebsiella pneumoniae

<400> SEQUENCE: 400
tccaaatcga catcgtttac ggcgt 25

<210> SEQ ID NO 401
<211> LENGTH: 19
<212> TYPE: DNA
<213> ORGANISM: Listeria monocytogenes

<400> SEQUENCE: 401
gcatgcgcca cactttatc 19

<210> SEQ ID NO 402
<211> LENGTH: 17
<212> TYPE: DNA
<213> ORGANISM: Mycobacterium avium

<400> SEQUENCE: 402
gctccctccc aaaaggg 17

<210> SEQ ID NO 403
<211> LENGTH: 17
<212> TYPE: DNA
<213> ORGANISM: Mycobacterium avium

<400> SEQUENCE: 403
gctccctccc aaaaggg 17

<210> SEQ ID NO 404
<211> LENGTH: 18
<212> TYPE: DNA
<213> ORGANISM: Neisseria gonorrhoeae

<400> SEQUENCE: 404
accccgccaa ccagctaa 18

<210> SEQ ID NO 405
<211> LENGTH: 18
<212> TYPE: DNA
<213> ORGANISM: Neisseria meningitidis

<400> SEQUENCE: 405
ttatccccca ctactcgg 18

<210> SEQ ID NO 406
<211> LENGTH: 17
<212> TYPE: DNA
<213> ORGANISM: Pandoraea apista

<400> SEQUENCE: 406
acctcgcggc ttggcga 17

<210> SEQ ID NO 407
<211> LENGTH: 19
<212> TYPE: DNA
<213> ORGANISM: Pandoraea sp.

<400> SEQUENCE: 407
gccttgcagt cacgaatgc 19

<210> SEQ ID NO 408
<211> LENGTH: 19
<212> TYPE: DNA
<213> ORGANISM: Pandoraea sp.

<400> SEQUENCE: 408
ccccgaggta ttaacccag 19

<210> SEQ ID NO 409
<211> LENGTH: 19
<212> TYPE: DNA
<213> ORGANISM: Propionibacterium acnes

<400> SEQUENCE: 409
accccacaaa agcagggcc 19

<210> SEQ ID NO 410
<211> LENGTH: 21
<212> TYPE: DNA
<213> ORGANISM: Propionibacterium acnes

<400> SEQUENCE: 410
caccccacaa aagcagggcc t 21

<210> SEQ ID NO 411
<211> LENGTH: 21
<212> TYPE: DNA
<213> ORGANISM: Proteus mirabilis

<400> SEQUENCE: 411
ccgatagtgc aaggtccgaa g 21

<210> SEQ ID NO 412
<211> LENGTH: 19
<212> TYPE: DNA
<213> ORGANISM: Proteus vulgaris

<400> SEQUENCE: 412
ccgtagacgt catgcggta 19

<210> SEQ ID NO 413
<211> LENGTH: 16
<212> TYPE: DNA
<213> ORGANISM: Pseudomonas aerigunosa

<400> SEQUENCE: 413
cccacccgag gtgctg 16

<210> SEQ ID NO 414
<211> LENGTH: 20
<212> TYPE: DNA
<213> ORGANISM: Pseudomonas aeruginosa

<400> SEQUENCE: 414
aagacgactc gtcatcagct 20

<210> SEQ ID NO 415
<211> LENGTH: 18
<212> TYPE: DNA
<213> ORGANISM: Ralstonia sp.

<400> SEQUENCE: 415
gcatgaggcc ttgcggtc 18

<210> SEQ ID NO 416
<211> LENGTH: 18
<212> TYPE: DNA
<213> ORGANISM: Ralstonia sp.

<400> SEQUENCE: 416
tcggtcttgc acaaccgc 18

<210> SEQ ID NO 417
<211> LENGTH: 23
<212> TYPE: DNA
<213> ORGANISM: Ralstonia sp.

<400> SEQUENCE: 417
ctaatgcatc tctgcttcgt tag 23

<210> SEQ ID NO 418
<211> LENGTH: 21
<212> TYPE: DNA
<213> ORGANISM: Staphylococcus lugdunensis

<400> SEQUENCE: 418
ctctagagcg gtcaaaggat g 21

<210> SEQ ID NO 419
<211> LENGTH: 19
<212> TYPE: DNA
<213> ORGANISM: Salmonella

<400> SEQUENCE: 419
cttcacctac gtgtcagcg 19

<210> SEQ ID NO 420
<211> LENGTH: 23
<212> TYPE: DNA
<213> ORGANISM: Serratia marcescens

<400> SEQUENCE: 420
cgtattaagc tcaccacctt cct 23

<210> SEQ ID NO 421
<211> LENGTH: 21
<212> TYPE: DNA
<213> ORGANISM: Shigella

<400> SEQUENCE: 421
aagtcgggat gaccccccttg c 21

<210> SEQ ID NO 422
<211> LENGTH: 24
<212> TYPE: DNA
<213> ORGANISM: Shigella

<400> SEQUENCE: 422
tgagcaaagg tattaacttt actc 24

<210> SEQ ID NO 423
<211> LENGTH: 24
<212> TYPE: DNA
<213> ORGANISM: Shigella

<400> SEQUENCE: 423
tgagcaaagg tattaacttt actc 24

<210> SEQ ID NO 424
<211> LENGTH: 21
<212> TYPE: DNA
<213> ORGANISM: Shigella sp.

<400> SEQUENCE: 424
aagtcgggat gacccccttg c 21

<210> SEQ ID NO 425
<211> LENGTH: 21
<212> TYPE: DNA
<213> ORGANISM: Staphylococcus

<400> SEQUENCE: 425
tttcgcacat cagcgtcagt t 21

<210> SEQ ID NO 426
<211> LENGTH: 21
<212> TYPE: DNA
<213> ORGANISM: Staphylococcus aureus

<400> SEQUENCE: 426
gcaagcttct cgtccgttcg c 21

<210> SEQ ID NO 427
<211> LENGTH: 21
<212> TYPE: DNA
<213> ORGANISM: Staphylococcus epidermides

<400> SEQUENCE: 427
ctctagagcg gtcaaaggat g 21

<210> SEQ ID NO 428
<211> LENGTH: 21
<212> TYPE: DNA
<213> ORGANISM: Stenotrophomonas maltophilia

<400> SEQUENCE: 428
ccctctacca cactctagtc g 21

<210> SEQ ID NO 429
<211> LENGTH: 21
<212> TYPE: DNA
<213> ORGANISM: Streptococcus agalactiae

<400> SEQUENCE: 429
actcctacca acgttcttct c 21

<210> SEQ ID NO 430
<211> LENGTH: 25
<212> TYPE: DNA
<213> ORGANISM: Streptococcus pneumoniae

<400> SEQUENCE: 430
ttaagcaaat gtcatgcaac atcya 25

<210> SEQ ID NO 431
<211> LENGTH: 21
<212> TYPE: DNA
<213> ORGANISM: Streptococcus pneumoniae

<400> SEQUENCE: 431
ctggtagtga tgcaagtgca c 21

<210> SEQ ID NO 432
<211> LENGTH: 24
<212> TYPE: DNA

<213> ORGANISM: Streptococcus pyogenes

<400> SEQUENCE: 432
gagcaattgc cccttttaaa ttac 24

<210> SEQ ID NO 433
<211> LENGTH: 24
<212> TYPE: DNA
<213> ORGANISM: Streptococcus sp.

<400> SEQUENCE: 433
gcacgtagtt agccgtccct ttct 24

<210> SEQ ID NO 434
<211> LENGTH: 21
<212> TYPE: DNA
<213> ORGANISM: Yersinia enterocolitica

<400> SEQUENCE: 434
agttattggc cttcctcctc g 21

<210> SEQ ID NO 435
<211> LENGTH: 19
<212> TYPE: DNA
<213> ORGANISM: Yersinia enterocolitica

<400> SEQUENCE: 435
cacatccgat ggcgtgagg 19

<210> SEQ ID NO 436
<211> LENGTH: 21
<212> TYPE: DNA
<213> ORGANISM: Achromobacter xylosoxidans

<400> SEQUENCE: 436
gcaagacctt gcactattgg a 21

<210> SEQ ID NO 437
<211> LENGTH: 26
<212> TYPE: DNA
<213> ORGANISM: Acinetobacter baumannii

<400> SEQUENCE: 437
aggcggctta ttaagtcgga tgtgaa 26

<210> SEQ ID NO 438
<211> LENGTH: 21
<212> TYPE: DNA
<213> ORGANISM: Acinetobacter sp.

<400> SEQUENCE: 438
tagagtatgg gagaggatgg t 21

<210> SEQ ID NO 439
<211> LENGTH: 25
<212> TYPE: DNA
<213> ORGANISM: Bacillus cereus

<400> SEQUENCE: 439
ataccggata acattttgaa ccgca 25

<210> SEQ ID NO 440
<211> LENGTH: 21

<212> TYPE: DNA
<213> ORGANISM: Bacteroides

<400> SEQUENCE: 440
cccacattgg aactgagaca c 21

<210> SEQ ID NO 441
<211> LENGTH: 20
<212> TYPE: DNA
<213> ORGANISM: Burkholderia cepacia

<400> SEQUENCE: 441
ggaacagagg gttgccaacc 20

<210> SEQ ID NO 442
<211> LENGTH: 18
<212> TYPE: DNA
<213> ORGANISM: Campylobacter

<400> SEQUENCE: 442
tggaaggacg cttagggc 18

<210> SEQ ID NO 443
<211> LENGTH: 21
<212> TYPE: DNA
<213> ORGANISM: Citrobacter freundii

<400> SEQUENCE: 443
ggaactgcat ccgaaactgg c 21

<210> SEQ ID NO 444
<211> LENGTH: 23
<212> TYPE: DNA
<213> ORGANISM: Clostridium difficile

<400> SEQUENCE: 444
tgcaagttga gcgatttact tcg 23

<210> SEQ ID NO 445
<211> LENGTH: 21
<212> TYPE: DNA
<213> ORGANISM: Clostridium perfringens

<400> SEQUENCE: 445
gtgtgggggt ttcaacacct c 21

<210> SEQ ID NO 446
<211> LENGTH: 22
<212> TYPE: DNA
<213> ORGANISM: Clostridium sp.

<400> SEQUENCE: 446
ccggatttac tgggcgtaaa gg 22

<210> SEQ ID NO 447
<211> LENGTH: 20
<212> TYPE: DNA
<213> ORGANISM: Corynebacterium sp.

<400> SEQUENCE: 447
ctcgtctgtg aaattccggg 20

<210> SEQ ID NO 448

<211> LENGTH: 20
<212> TYPE: DNA
<213> ORGANISM: Corynebacterium sp.

<400> SEQUENCE: 448
gtcgtctgtg aaattccggg 20

<210> SEQ ID NO 449
<211> LENGTH: 27
<212> TYPE: DNA
<213> ORGANISM: Escherichia coli

<400> SEQUENCE: 449
gagtaaagtt aatacctttg ctcattg 27

<210> SEQ ID NO 450
<211> LENGTH: 22
<212> TYPE: DNA
<213> ORGANISM: Escherichia coli

<400> SEQUENCE: 450
gcacagagca atctgtgtga ct 22

<210> SEQ ID NO 451
<211> LENGTH: 22
<212> TYPE: DNA
<213> ORGANISM: Enterobacter aerogenes

<400> SEQUENCE: 451
gaaactggca ggctagagtc tt 22

<210> SEQ ID NO 452
<211> LENGTH: 19
<212> TYPE: DNA
<213> ORGANISM: Enterobacter sakazakii

<400> SEQUENCE: 452
tcctgcagag atgcgggag 19

<210> SEQ ID NO 453
<211> LENGTH: 19
<212> TYPE: DNA
<213> ORGANISM: Enterobacter sakazakii

<400> SEQUENCE: 453
tcctgcagag atgcgggag 19

<210> SEQ ID NO 454
<211> LENGTH: 23
<212> TYPE: DNA
<213> ORGANISM: Unknown
<220> FEATURE:
<223> OTHER INFORMATION: Enterobacteriaceae

<400> SEQUENCE: 454
gggggataac tactggaaac ggt 23

<210> SEQ ID NO 455
<211> LENGTH: 20
<212> TYPE: DNA
<213> ORGANISM: Enterococcus

<400> SEQUENCE: 455
ctttcgggtg tcgctgatgg 20

<210> SEQ ID NO 456
<211> LENGTH: 24
<212> TYPE: DNA
<213> ORGANISM: Enterococcus

<400> SEQUENCE: 456
aagcgagcgc aggcggtttc ttaa 24

<210> SEQ ID NO 457
<211> LENGTH: 19
<212> TYPE: DNA
<213> ORGANISM: Enterococcus faecalis

<400> SEQUENCE: 457
cttctttcct cccgagtgc 19

<210> SEQ ID NO 458
<211> LENGTH: 25
<212> TYPE: DNA
<213> ORGANISM: Enterococcus faecium

<400> SEQUENCE: 458
cgcatggttt tgatttgaaa ggcgc 25

<210> SEQ ID NO 459
<211> LENGTH: 25
<212> TYPE: DNA
<213> ORGANISM: Escherichia coli

<400> SEQUENCE: 459
gatatgtagg tgaagcgact tgctc 25

<210> SEQ ID NO 460
<211> LENGTH: 20
<212> TYPE: DNA
<213> ORGANISM: Haemophilus influenzae

<400> SEQUENCE: 460
atcggaagat gaaagtgcgg 20

<210> SEQ ID NO 461
<211> LENGTH: 19
<212> TYPE: DNA
<213> ORGANISM: Inquilinus limosus

<400> SEQUENCE: 461
gggcgggctt gaatccaag 19

<210> SEQ ID NO 462
<211> LENGTH: 18
<212> TYPE: DNA
<213> ORGANISM: Klebsiella pneumoniae

<400> SEQUENCE: 462
agcaccttcg ggtgtgac 18

<210> SEQ ID NO 463
<211> LENGTH: 23
<212> TYPE: DNA
<213> ORGANISM: Klebsiella oxytoca

<400> SEQUENCE: 463
taagtgaagt gacttgctca tgg 23

<210> SEQ ID NO 464
<211> LENGTH: 18
<212> TYPE: DNA
<213> ORGANISM: Klebsiella pneumoniae

<400> SEQUENCE: 464
agcaccttcg ggtgtgac 18

<210> SEQ ID NO 465
<211> LENGTH: 25
<212> TYPE: DNA
<213> ORGANISM: Klebsiella pneumoniae

<400> SEQUENCE: 465
acgccgtaaa cgatgtcgat ttgga 25

<210> SEQ ID NO 466
<211> LENGTH: 19
<212> TYPE: DNA
<213> ORGANISM: Listeria monocytogenes

<400> SEQUENCE: 466
gataaagtgt ggcgcatgc 19

<210> SEQ ID NO 467
<211> LENGTH: 17
<212> TYPE: DNA
<213> ORGANISM: Mycobacterium avium

<400> SEQUENCE: 467 ccctttggg agggagc 17

<210> SEQ ID NO 468
<211> LENGTH: 17
<212> TYPE: DNA
<213> ORGANISM: Mycobacterium avium

<400> SEQUENCE: 468 ccctttggg agggagc 17

<210> SEQ ID NO 469
<211> LENGTH: 18
<212> TYPE: DNA
<213> ORGANISM: Neisseria gonorrhoeae

<400> SEQUENCE: 469
ttagctggtt ggcggggt 18

<210> SEQ ID NO 470
<211> LENGTH: 18
<212> TYPE: DNA
<213> ORGANISM: Neisseria meningitidis

<400> SEQUENCE: 470
ccgagtagtg ggggataa 18

<210> SEQ ID NO 471
<211> LENGTH: 17
<212> TYPE: DNA
<213> ORGANISM: Pandoraea apista

<400> SEQUENCE: 471
tcgccaagcc gcgaggt 17

<210> SEQ ID NO 472
<211> LENGTH: 19
<212> TYPE: DNA
<213> ORGANISM: Pandoraea sp.

<400> SEQUENCE: 472
gcattcgtga ctgcaaggc 19

<210> SEQ ID NO 473
<211> LENGTH: 19
<212> TYPE: DNA
<213> ORGANISM: Pandoraea sp.

<400> SEQUENCE: 473
ctgggttaat acctcgggg 19

<210> SEQ ID NO 474
<211> LENGTH: 19
<212> TYPE: DNA
<213> ORGANISM: Propionibacterium acnes

<400> SEQUENCE: 474
ggccctgctt ttgtggggt 19

<210> SEQ ID NO 475
<211> LENGTH: 21
<212> TYPE: DNA
<213> ORGANISM: Propionibacterium acnes

<400> SEQUENCE: 475
aggccctgct tttctggggt g 21

<210> SEQ ID NO 476
<211> LENGTH: 21
<212> TYPE: DNA
<213> ORGANISM: Proteus mirabilis

<400> SEQUENCE: 476
cttcggacct tgcactatcg g 21

<210> SEQ ID NO 477
<211> LENGTH: 19
<212> TYPE: DNA
<213> ORGANISM: Proteus vulgaris

<400> SEQUENCE: 477
taccgcatga cgtctacgg 19

<210> SEQ ID NO 478
<211> LENGTH: 16
<212> TYPE: DNA
<213> ORGANISM: Pseudomonas aerigunosa

<400> SEQUENCE: 478
cagcacctcg ggtggg 16

<210> SEQ ID NO 479
<211> LENGTH: 20
<212> TYPE: DNA
<213> ORGANISM: Pseudomonas aeruginosa

<400> SEQUENCE: 479
agctgatgac gagtcgtctt 20

<210> SEQ ID NO 480
<211> LENGTH: 18
<212> TYPE: DNA
<213> ORGANISM: Ralstonia sp.

<400> SEQUENCE: 480
gaccgcaagg cctcatgc 18

<210> SEQ ID NO 481
<211> LENGTH: 18
<212> TYPE: DNA
<213> ORGANISM: Ralstonia sp.

<400> SEQUENCE: 481
gcggttgtgc aagaccga 18

<210> SEQ ID NO 482
<211> LENGTH: 23
<212> TYPE: DNA
<213> ORGANISM: Ralstonia sp.

<400> SEQUENCE: 482
ctaacgaagc agagatgcat tag 23

<210> SEQ ID NO 483
<211> LENGTH: 21
<212> TYPE: DNA
<213> ORGANISM: Staphylococcus lugdunensis

<400> SEQUENCE: 483
catcctttga ccgctctaga g 21

<210> SEQ ID NO 484
<211> LENGTH: 19
<212> TYPE: DNA
<213> ORGANISM: Salmonella

<400> SEQUENCE: 484
cgctgacacg taggtgaag 19

<210> SEQ ID NO 485
<211> LENGTH: 23
<212> TYPE: DNA
<213> ORGANISM: Serratia marcescens

<400> SEQUENCE: 485
aggaaggtgg tgagcttaat acg 23

<210> SEQ ID NO 486
<211> LENGTH: 21
<212> TYPE: DNA
<213> ORGANISM: Shigella

<400> SEQUENCE: 486
gcaagggggt catcccgact t 21

<210> SEQ ID NO 487
<211> LENGTH: 24
<212> TYPE: DNA
<213> ORGANISM: Shigella

<400> SEQUENCE: 487
gagtaaagtt aatacctttg ctca 24

<210> SEQ ID NO 488
<211> LENGTH: 24
<212> TYPE: DNA
<213> ORGANISM: Shigella

<400> SEQUENCE: 488
gagtaaagtt aatacctttg ctca 24

<210> SEQ ID NO 489
<211> LENGTH: 21
<212> TYPE: DNA
<213> ORGANISM: Shigella sp.

<400> SEQUENCE: 489
gcaagggggt catcccgact t 21

<210> SEQ ID NO 490
<211> LENGTH: 21
<212> TYPE: DNA
<213> ORGANISM: Staphylococcus

<400> SEQUENCE: 490
aactgacgct gatgtgcgaa a 21

<210> SEQ ID NO 491
<211> LENGTH: 21
<212> TYPE: DNA
<213> ORGANISM: Staphylococcus aureus

<400> SEQUENCE: 491
gcgaacggac gagaagcttg c 21

<210> SEQ ID NO 492
<211> LENGTH: 21
<212> TYPE: DNA
<213> ORGANISM: Staphylococcus epidermides

<400> SEQUENCE: 492
ctctagagcg gtcaaaggat g 21

<210> SEQ ID NO 493
<211> LENGTH: 21
<212> TYPE: DNA
<213> ORGANISM: Stenotrophomonas maltophilia

<400> SEQUENCE: 493
cgactagagt gtggtagagg g 21

<210> SEQ ID NO 494
<211> LENGTH: 21
<212> TYPE: DNA
<213> ORGANISM: Streptococcus agalactiae

<400> SEQUENCE: 494
gagaagaacg ttggtaggag t 21

<210> SEQ ID NO 495
<211> LENGTH: 25
<212> TYPE: DNA

<213> ORGANISM: Streptococcus pneumoniae

<400> SEQUENCE: 495
tagatgttgc atgacatttg cttaa 25

<210> SEQ ID NO 496
<211> LENGTH: 21
<212> TYPE: DNA
<213> ORGANISM: Streptococcus pneumoniae

<400> SEQUENCE: 496
gtgcacttgc atcactacca g 21

<210> SEQ ID NO 497
<211> LENGTH: 24
<212> TYPE: DNA
<213> ORGANISM: Streptococcus pyogenes

<400> SEQUENCE: 497
gtaatttaaa aggggcaatt gctc 24

<210> SEQ ID NO 498
<211> LENGTH: 24
<212> TYPE: DNA
<213> ORGANISM: Streptococcus sp.

<400> SEQUENCE: 498
agaaagggac ggctaactac gtgc 24

<210> SEQ ID NO 499
<211> LENGTH: 21
<212> TYPE: DNA
<213> ORGANISM: Yersinia enterocolitica

<400> SEQUENCE: 499
cgaggaggaa ggccaataac t 21

<210> SEQ ID NO 500
<211> LENGTH: 19
<212> TYPE: DNA
<213> ORGANISM: Yersinia enterocolitica

<400> SEQUENCE: 500
cctcacgcca tcggatgtg 19

<210> SEQ ID NO 501
<211> LENGTH: 21
<212> TYPE: DNA
<213> ORGANISM: Achromobacter xylosoxidans

<400> SEQUENCE: 501
gtagggcgta tgcggtatta g 21

<210> SEQ ID NO 502
<211> LENGTH: 21
<212> TYPE: DNA
<213> ORGANISM: Acinetobacter baumannii

<400> SEQUENCE: 502
gtaaatccga ttaacgctcg c 21

<210> SEQ ID NO 503
<211> LENGTH: 19

<212> TYPE: DNA
<213> ORGANISM: Acinetobacter sp.

<400> SEQUENCE: 503
ttcccaagtt aagctcggg 19

<210> SEQ ID NO 504
<211> LENGTH: 21
<212> TYPE: DNA
<213> ORGANISM: Bacillus cereus group

<400> SEQUENCE: 504
gagttatccc agtcttatgg g 21

<210> SEQ ID NO 505
<211> LENGTH: 19
<212> TYPE: DNA
<213> ORGANISM: Bacteroides

<400> SEQUENCE: 505
cctatccatc gaaggctag 19

<210> SEQ ID NO 506
<211> LENGTH: 18
<212> TYPE: DNA
<213> ORGANISM: Burkholderia cepacia complex

<400> SEQUENCE: 506
gaagccctac ccataagg 18

<210> SEQ ID NO 507
<211> LENGTH: 25
<212> TYPE: DNA
<213> ORGANISM: Campylobacter

<400> SEQUENCE: 507
aatattaacc aatttgccat cgtct 25

<210> SEQ ID NO 508
<211> LENGTH: 22
<212> TYPE: DNA
<213> ORGANISM: Citrobacter freundii

<400> SEQUENCE: 508
atttcacatc cgacttgaca ga 22

<210> SEQ ID NO 509
<211> LENGTH: 18
<212> TYPE: DNA
<213> ORGANISM: Clostridium difficile

<400> SEQUENCE: 509
cagcgttcat cctgagcc 18

<210> SEQ ID NO 510
<211> LENGTH: 20
<212> TYPE: DNA
<213> ORGANISM: Clostridium perfringens

<400> SEQUENCE: 510
ggactaccag ggtatctaat 20

<210> SEQ ID NO 511

<211> LENGTH: 18
<212> TYPE: DNA
<213> ORGANISM: Clostridium sp.

<400> SEQUENCE: 511
tattaccgcg gctgctgg 18

<210> SEQ ID NO 512
<211> LENGTH: 21
<212> TYPE: DNA
<213> ORGANISM: Corynebacterium sp.

<400> SEQUENCE: 512
tttacgccca gtaattccgg a 21

<210> SEQ ID NO 513
<211> LENGTH: 21
<212> TYPE: DNA
<213> ORGANISM: Corynebacterium sp.

<400> SEQUENCE: 513
tttacgccca gtaattccgg a 21

<210> SEQ ID NO 514
<211> LENGTH: 21
<212> TYPE: DNA
<213> ORGANISM: Escherichia coli

<400> SEQUENCE: 514
agtactttac aacccgaagg c 21

<210> SEQ ID NO 515
<211> LENGTH: 23
<212> TYPE: DNA
<213> ORGANISM: Escherichia coli

<400> SEQUENCE: 515
cggtttcagg ttctttttca ctc 23

<210> SEQ ID NO 516
<211> LENGTH: 19
<212> TYPE: DNA
<213> ORGANISM: Enterobacter aerogenes

<400> SEQUENCE: 516
ccccggggat ttcacatcc 19

<210> SEQ ID NO 517
<211> LENGTH: 21
<212> TYPE: DNA
<213> ORGANISM: Enterobacter sakazakii

<400> SEQUENCE: 517
aaggttcttc gcgttgcatc g 21

<210> SEQ ID NO 518
<211> LENGTH: 21
<212> TYPE: DNA
<213> ORGANISM: Enterobacter sakazakii

<400> SEQUENCE: 518
aaggttcttc gcgttgcatc g 21

<210> SEQ ID NO 519
<211> LENGTH: 19
<212> TYPE: DNA
<213> ORGANISM: Unknown
<220> FEATURE:
<223> OTHER INFORMATION: Enterobacteriaceae

<400> SEQUENCE: 519
gacattactc acccgtccg 19

<210> SEQ ID NO 520
<211> LENGTH: 24
<212> TYPE: DNA
<213> ORGANISM: Enterococcus

<400> SEQUENCE: 520
ggtttcgatt gttatacggt atta 24

<210> SEQ ID NO 521
<211> LENGTH: 19
<212> TYPE: DNA
<213> ORGANISM: Enterococcus

<400> SEQUENCE: 521
aacgcttgcc acctacgta 19

<210> SEQ ID NO 522
<211> LENGTH: 16
<212> TYPE: DNA
<213> ORGANISM: Enterococcus faecalis

<400> SEQUENCE: 522
acgccgccag cgttcg 16

<210> SEQ ID NO 523
<211> LENGTH: 21
<212> TYPE: DNA
<213> ORGANISM: Enterococcus faecium

<400> SEQUENCE: 523
cctgtttcca agtgttatcc c 21

<210> SEQ ID NO 524
<211> LENGTH: 20
<212> TYPE: DNA
<213> ORGANISM: Escherichia coli

<400> SEQUENCE: 524
agttacggca ccattttgcc 20

<210> SEQ ID NO 525
<211> LENGTH: 19
<212> TYPE: DNA
<213> ORGANISM: Haemophilus influenzae

<400> SEQUENCE: 525
tttcccgtcg ttatccccc 19

<210> SEQ ID NO 526
<211> LENGTH: 18
<212> TYPE: DNA
<213> ORGANISM: Inquilinus limosus

<400> SEQUENCE: 526
tgagcccggg gctttcac 18

<210> SEQ ID NO 527
<211> LENGTH: 20
<212> TYPE: DNA
<213> ORGANISM: Klebsiella pneumoniae

<400> SEQUENCE: 527
cccactgctt gtacgtacac 20

<210> SEQ ID NO 528
<211> LENGTH: 22
<212> TYPE: DNA
<213> ORGANISM: Klebsiella oxytoca

<400> SEQUENCE: 528
mgaagttacg gcaccatttt gc 22

<210> SEQ ID NO 529
<211> LENGTH: 23
<212> TYPE: DNA
<213> ORGANISM: Klebsiella pneumoniae

<400> SEQUENCE: 529
ggtttcaggt tctttttcac tcc 23

<210> SEQ ID NO 530
<211> LENGTH: 18
<212> TYPE: DNA
<213> ORGANISM: Klebsiella pneumoniae

<400> SEQUENCE: 530
atcctgtttg ctccccac 18

<210> SEQ ID NO 531
<211> LENGTH: 19
<212> TYPE: DNA
<213> ORGANISM: Listeria monocytogenes

<400> SEQUENCE: 531
ttcccggagt tatccccaa 19

<210> SEQ ID NO 532
<211> LENGTH: 21
<212> TYPE: DNA
<213> ORGANISM: Mycobacterium avium

<400> SEQUENCE: 532
gggtgttacc gactttcatg a 21

<210> SEQ ID NO 533
<211> LENGTH: 22
<212> TYPE: DNA
<213> ORGANISM: Mycobacterium avium

<400> SEQUENCE: 533
gtgttaccga ctttcatgac gt 22

<210> SEQ ID NO 534
<211> LENGTH: 17
<212> TYPE: DNA
<213> ORGANISM: Neisseria gonorrhoeae

<400> SEQUENCE: 534
gatagcgcaa ggcccga 17

<210> SEQ ID NO 535
<211> LENGTH: 16
<212> TYPE: DNA
<213> ORGANISM: Neisseria meningitidis

<400> SEQUENCE: 535
cgttcgccac tcgcca 16

<210> SEQ ID NO 536
<211> LENGTH: 19
<212> TYPE: DNA
<213> ORGANISM: Pandoraea apista

<400> SEQUENCE: 536
tgacgtgtga agccctacc 19

<210> SEQ ID NO 537
<211> LENGTH: 19
<212> TYPE: DNA
<213> ORGANISM: Pandoraea sp.

<400> SEQUENCE: 537
ggggatttca catccgtct 19

<210> SEQ ID NO 538
<211> LENGTH: 21
<212> TYPE: DNA
<213> ORGANISM: Pandoraea sp.

<400> SEQUENCE: 538
ctttacaacc cgaaggcctt c 21

<210> SEQ ID NO 539
<211> LENGTH: 17
<212> TYPE: DNA
<213> ORGANISM: Propionibacterium acnes

<400> SEQUENCE: 539
taagcacgcc gccagcg 17

<210> SEQ ID NO 540
<211> LENGTH: 16
<212> TYPE: DNA
<213> ORGANISM: Propionibacterium acnes

<400> SEQUENCE: 540
taagcacgcc gccagc 16

<210> SEQ ID NO 541
<211> LENGTH: 22
<212> TYPE: DNA
<213> ORGANISM: Proteus mirabilis

<400> SEQUENCE: 541
gtagacatta tgcggtatta gc 22

<210> SEQ ID NO 542
<211> LENGTH: 18
<212> TYPE: DNA
<213> ORGANISM: Proteus vulgaris

<400> SEQUENCE: 542
ttatccccct ccatcagg 18

<210> SEQ ID NO 543
<211> LENGTH: 21
<212> TYPE: DNA
<213> ORGANISM: Pseudomonas aerigunosa

<400> SEQUENCE: 543
ctcgttacgg gacttaaccc a 21

<210> SEQ ID NO 544
<211> LENGTH: 18
<212> TYPE: DNA
<213> ORGANISM: Pseudomonas aeruginosa

<400> SEQUENCE: 544
gatttaccta agatttca 18

<210> SEQ ID NO 545
<211> LENGTH: 23
<212> TYPE: DNA
<213> ORGANISM: Ralstonia sp.

<400> SEQUENCE: 545
gtcgtatgcg gtattagcta atc 23

<210> SEQ ID NO 546
<211> LENGTH: 24
<212> TYPE: DNA
<213> ORGANISM: Ralstonia sp.

<400> SEQUENCE: 546
cagtaattcc gattaacgct tgga 24

<210> SEQ ID NO 547
<211> LENGTH: 22
<212> TYPE: DNA
<213> ORGANISM: Ralstonia sp.

<400> SEQUENCE: 547
aggtttttcg cgttgcatcg aa 22

<210> SEQ ID NO 548
<211> LENGTH: 23
<212> TYPE: DNA
<213> ORGANISM: Staphylococcus lugdunensis

<400> SEQUENCE: 548
gttgcttcga attagaccac atg 23

<210> SEQ ID NO 549
<211> LENGTH: 20
<212> TYPE: DNA
<213> ORGANISM: Salmonella

<400> SEQUENCE: 549
ggcaccattt tgcctagttc 20

<210> SEQ ID NO 550
<211> LENGTH: 18
<212> TYPE: DNA
<213> ORGANISM: Serratia marcescens

<400> SEQUENCE: 550
acccgaaggc cttcttca 18

<210> SEQ ID NO 551
<211> LENGTH: 19
<212> TYPE: DNA
<213> ORGANISM: Shigella

<400> SEQUENCE: 551
cggagatgag ttcacgagg 19

<210> SEQ ID NO 552
<211> LENGTH: 21
<212> TYPE: DNA
<213> ORGANISM: Shigella

<400> SEQUENCE: 552
tactttacaa cccgaaggcc t 21

<210> SEQ ID NO 553
<211> LENGTH: 21
<212> TYPE: DNA
<213> ORGANISM: Shigella

<400> SEQUENCE: 553
tactttacaa cccgaaggcc t 21

<210> SEQ ID NO 554
<211> LENGTH: 19
<212> TYPE: DNA
<213> ORGANISM: Shigella sp.

<400> SEQUENCE: 554
cggagatgag ttcacgagg 19

<210> SEQ ID NO 555
<211> LENGTH: 18
<212> TYPE: DNA
<213> ORGANISM: Staphylococcus

<400> SEQUENCE: 555
cgccactggt gttcctcc 18

<210> SEQ ID NO 556
<211> LENGTH: 17
<212> TYPE: DNA
<213> ORGANISM: Staphylococcus aureus

<400> SEQUENCE: 556
cgccgccagc gttcatc 17

<210> SEQ ID NO 557
<211> LENGTH: 24
<212> TYPE: DNA
<213> ORGANISM: Staphylococcus epidermides

<400> SEQUENCE: 557
cgttgcttcg aattaaacca catg 24

<210> SEQ ID NO 558
<211> LENGTH: 18
<212> TYPE: DNA

<213> ORGANISM: Stenotrophomonas maltophilia

<400> SEQUENCE: 558
tcccaggttg agcccagg 18

<210> SEQ ID NO 559
<211> LENGTH: 21
<212> TYPE: DNA
<213> ORGANISM: Streptococcus agalactiae

<400> SEQUENCE: 559
gaaaaccttc ttcactcacg c 21

<210> SEQ ID NO 560
<211> LENGTH: 21
<212> TYPE: DNA
<213> ORGANISM: Streptococcus pneumoniae

<400> SEQUENCE: 560
tttccaatag ttatcccccg c 21

<210> SEQ ID NO 561
<211> LENGTH: 24
<212> TYPE: DNA
<213> ORGANISM: Streptococcus pneumoniae

<400> SEQUENCE: 561
yactcttatg cggtattagc tatc 24

<210> SEQ ID NO 562
<211> LENGTH: 24
<212> TYPE: DNA
<213> ORGANISM: Streptococcus pyogenes

<400> SEQUENCE: 562
cggtattagc tatcgtttcc aata 24

<210> SEQ ID NO 563
<211> LENGTH: 19
<212> TYPE: DNA
<213> ORGANISM: Streptococcus sp.

<400> SEQUENCE: 563
ggattttcca ctccgacca 19

<210> SEQ ID NO 564
<211> LENGTH: 19
<212> TYPE: DNA
<213> ORGANISM: Yersinia enterocolitica

<400> SEQUENCE: 564
aggccttctt cacacacgc 19

<210> SEQ ID NO 565
<211> LENGTH: 21
<212> TYPE: DNA
<213> ORGANISM: Yersinia enterocolitica

<400> SEQUENCE: 565
tttggtccga agacgttatg c 21

<210> SEQ ID NO 566
<211> LENGTH: 18

<212> TYPE: DNA
<213> ORGANISM: Achromobacter xylosoxidans

<400> SEQUENCE: 566
gatcccctgc tttccccc 18

<210> SEQ ID NO 567
<211> LENGTH: 18
<212> TYPE: DNA
<213> ORGANISM: Acinetobacter baumannii

<400> SEQUENCE: 567
acgcacgctt tacgccca 18

<210> SEQ ID NO 568
<211> LENGTH: 21
<212> TYPE: DNA
<213> ORGANISM: Acinetobacter sp.

<400> SEQUENCE: 568
gctcaccagt atcgaatgca a 21

<210> SEQ ID NO 569
<211> LENGTH: 16
<212> TYPE: DNA
<213> ORGANISM: Bacillus cereus

<400> SEQUENCE: 569
tagccccggt ttcccg 16

<210> SEQ ID NO 570
<211> LENGTH: 19
<212> TYPE: DNA
<213> ORGANISM: Bacteroides

<400> SEQUENCE: 570
ggaccttcct ctcagaacc 19

<210> SEQ ID NO 571
<211> LENGTH: 18
<212> TYPE: DNA
<213> ORGANISM: Burkholderia cepacia

<400> SEQUENCE: 571
gaccattgta tgacgtgt 18

<210> SEQ ID NO 572
<211> LENGTH: 23
<212> TYPE: DNA
<213> ORGANISM: Campylobacter

<400> SEQUENCE: 572
tcgcacacta atgttggtat tgg 23

<210> SEQ ID NO 573
<211> LENGTH: 16
<212> TYPE: DNA
<213> ORGANISM: Citrobacter freundii

<400> SEQUENCE: 573
caggttgagc ccgggg 16

<210> SEQ ID NO 574

<211> LENGTH: 17
<212> TYPE: DNA
<213> ORGANISM: Clostridium difficile

<400> SEQUENCE: 574
tgtgttaggc acgccgc 17

<210> SEQ ID NO 575
<211> LENGTH: 23
<212> TYPE: DNA
<213> ORGANISM: Clostridium perfringens

<400> SEQUENCE: 575
ctagtattca tcgtttacgg cgt 23

<210> SEQ ID NO 576
<211> LENGTH: 19
<212> TYPE: DNA
<213> ORGANISM: Clostridium sp.

<400> SEQUENCE: 576
ataacgctcg ccacctacg 19

<210> SEQ ID NO 577
<211> LENGTH: 26
<212> TYPE: DNA
<213> ORGANISM: Corynebacterium sp.

<400> SEQUENCE: 577
gttaagcaca aaccacctac gagctc 26

<210> SEQ ID NO 578
<211> LENGTH: 26
<212> TYPE: DNA
<213> ORGANISM: Corynebacterium sp.

<400> SEQUENCE: 578
gttaagcaca aaccacctac gagctc 26

<210> SEQ ID NO 579
<211> LENGTH: 17
<212> TYPE: DNA
<213> ORGANISM: Escherichia coli

<400> SEQUENCE: 579
ccttcctccc cgctgaa 17

<210> SEQ ID NO 580
<211> LENGTH: 20
<212> TYPE: DNA
<213> ORGANISM: Escherichia coli

<400> SEQUENCE: 580
tcccactgct tgtacgtaca 20

<210> SEQ ID NO 581
<211> LENGTH: 19
<212> TYPE: DNA
<213> ORGANISM: Enterobacter aerogenes

<400> SEQUENCE: 581
ggaattctac ccccctcta 19

<210> SEQ ID NO 582
<211> LENGTH: 21
<212> TYPE: DNA
<213> ORGANISM: Enterobacter sakazakii

<400> SEQUENCE: 582
tcagagttcc cgaaggcagg t 21

<210> SEQ ID NO 583
<211> LENGTH: 21
<212> TYPE: DNA
<213> ORGANISM: Enterobacter sakazakii

<400> SEQUENCE: 583
tcagagttcc cgaaggcagg t 21

<210> SEQ ID NO 584
<211> LENGTH: 19
<212> TYPE: DNA
<213> ORGANISM: Unknown
<220> FEATURE:
<223> OTHER INFORMATION: Enterobacteriaceae

<400> SEQUENCE: 584
tccatcaggc agtttccca 19

<210> SEQ ID NO 585
<211> LENGTH: 23
<212> TYPE: DNA
<213> ORGANISM: Enterococcus

<400> SEQUENCE: 585
cgcctttcaa atcaaaacca tgc 23

<210> SEQ ID NO 586
<211> LENGTH: 20
<212> TYPE: DNA
<213> ORGANISM: Enterococcus

<400> SEQUENCE: 586
tacgcccaat aaatccggac 20

<210> SEQ ID NO 587
<211> LENGTH: 23
<212> TYPE: DNA
<213> ORGANISM: Enterococcus faecalis

<400> SEQUENCE: 587
cgttcgactt gcatgtatta ggc 23

<210> SEQ ID NO 588
<211> LENGTH: 26
<212> TYPE: DNA
<213> ORGANISM: Enterococcus faecium

<400> SEQUENCE: 588
gtttcgattg ttatacggta ttagca 26

<210> SEQ ID NO 589
<211> LENGTH: 17
<212> TYPE: DNA
<213> ORGANISM: Escherichia coli

<400> SEQUENCE: 589
agcgtgcctt ctcccga 17

<210> SEQ ID NO 590
<211> LENGTH: 21
<212> TYPE: DNA
<213> ORGANISM: Haemophilus influenzae

<400> SEQUENCE: 590
aatacgcggt attagcgaca g 21

<210> SEQ ID NO 591
<211> LENGTH: 22
<212> TYPE: DNA
<213> ORGANISM: Inquilinus limosus

<400> SEQUENCE: 591
gtatcaaatg cagttcccag gt 22

<210> SEQ ID NO 592
<211> LENGTH: 23
<212> TYPE: DNA
<213> ORGANISM: Klebsiella pneumoniae

<400> SEQUENCE: 592
ggtttcaggt tctttttcac tcc 23

<210> SEQ ID NO 593
<211> LENGTH: 19
<212> TYPE: DNA
<213> ORGANISM: Klebsiella oxytoca

<400> SEQUENCE: 593
ccatcagcgt gccttctcc 19

<210> SEQ ID NO 594
<211> LENGTH: 20
<212> TYPE: DNA
<213> ORGANISM: Klebsiella pneumoniae

<400> SEQUENCE: 594
cccactgctt gtacgtacac 20

<210> SEQ ID NO 595
<211> LENGTH: 18
<212> TYPE: DNA
<213> ORGANISM: Klebsiella pneumoniae

<400> SEQUENCE: 595
ggactaccag ggtatcta 18

<210> SEQ ID NO 596
<211> LENGTH: 19
<212> TYPE: DNA
<213> ORGANISM: Listeria monocytogenes

<400> SEQUENCE: 596
attcggtatt agccccggt 19

<210> SEQ ID NO 597
<211> LENGTH: 18
<212> TYPE: DNA
<213> ORGANISM: Mycobacterium avium

<400> SEQUENCE: 597
ggttaggcca ctggcttc 18

<210> SEQ ID NO 598
<211> LENGTH: 18
<212> TYPE: DNA
<213> ORGANISM: Mycobacterium avium

<400> SEQUENCE: 598
ttaggccact ggcttcgg 18

<210> SEQ ID NO 599
<211> LENGTH: 18
<212> TYPE: DNA
<213> ORGANISM: Neisseria gonorrhoeae

<400> SEQUENCE: 599
tcagatatcg gccgctcg 18

<210> SEQ ID NO 600
<211> LENGTH: 23
<212> TYPE: DNA
<213> ORGANISM: Neisseria meningitidis

<400> SEQUENCE: 600
tacgttccga tatgttactc acc 23

<210> SEQ ID NO 601
<211> LENGTH: 21
<212> TYPE: DNA
<213> ORGANISM: Pandoraea apista

<400> SEQUENCE: 601
ccctctgtac cgaccattgt a 21

<210> SEQ ID NO 602
<211> LENGTH: 18
<212> TYPE: DNA
<213> ORGANISM: Pandoraea sp.

<400> SEQUENCE: 602
agttcccagg ttgagccc 18

<210> SEQ ID NO 603
<211> LENGTH: 24
<212> TYPE: DNA
<213> ORGANISM: Pandoraea sp.

<400> SEQUENCE: 603
aggatttctt tccggacaaa agtg 24

<210> SEQ ID NO 604
<211> LENGTH: 22
<212> TYPE: DNA
<213> ORGANISM: Propionibacterium acnes

<400> SEQUENCE: 604
tttccgttcg acttgcatgt gt 22

<210> SEQ ID NO 605
<211> LENGTH: 22
<212> TYPE: DNA
<213> ORGANISM: Propionibacterium acnes

<400> SEQUENCE: 605
tttccgttcg acttgcatgt gt 22

<210> SEQ ID NO 606
<211> LENGTH: 17
<212> TYPE: DNA
<213> ORGANISM: Proteus mirabilis

<400> SEQUENCE: 606
agcccctgct ttggtcc 17

<210> SEQ ID NO 607
<211> LENGTH: 20
<212> TYPE: DNA
<213> ORGANISM: Proteus vulgaris

<400> SEQUENCE: 607
ttagccaccg tttccagtag 20

<210> SEQ ID NO 608
<211> LENGTH: 22
<212> TYPE: DNA
<213> ORGANISM: Pseudomonas aerigunosa

<400> SEQUENCE: 608
gtaactaagg acaagggttg cg 22

<210> SEQ ID NO 609
<211> LENGTH: 18
<212> TYPE: DNA
<213> ORGANISM: Pseudomonas aeruginosa

<400> SEQUENCE: 609
ctcggccttg aaaccccg 18

<210> SEQ ID NO 610
<211> LENGTH: 18
<212> TYPE: DNA
<213> ORGANISM: Ralstonia sp.

<400> SEQUENCE: 610
ccccactttc accctcag 18

<210> SEQ ID NO 611
<211> LENGTH: 18
<212> TYPE: DNA
<213> ORGANISM: Ralstonia sp.

<400> SEQUENCE: 611
ctgcgcacgc tttacgcc 18

<210> SEQ ID NO 612
<211> LENGTH: 20
<212> TYPE: DNA
<213> ORGANISM: Ralstonia sp.

<400> SEQUENCE: 612
tggcatgtca agggtaggta 20

<210> SEQ ID NO 613
<211> LENGTH: 24
<212> TYPE: DNA
<213> ORGANISM: Staphylococcus lugdunensis

<400> SEQUENCE: 613
tcaagatttg gtaaggttct tcgc 24

<210> SEQ ID NO 614
<211> LENGTH: 19
<212> TYPE: DNA
<213> ORGANISM: Salmonella

<400> SEQUENCE: 614
tgccttctcc cgaagttac 19

<210> SEQ ID NO 615
<211> LENGTH: 21
<212> TYPE: DNA
<213> ORGANISM: Serratia marcescens

<400> SEQUENCE: 615
cctcgctgaa agtgctttac a 21

<210> SEQ ID NO 616
<211> LENGTH: 19
<212> TYPE: DNA
<213> ORGANISM: Shigella

<400> SEQUENCE: 616
cgaaacagtg ctctacccc 19

<210> SEQ ID NO 617
<211> LENGTH: 19
<212> TYPE: DNA
<213> ORGANISM: Shigella

<400> SEQUENCE: 617
ccttcctccc cgctgaaag 19

<210> SEQ ID NO 618
<211> LENGTH: 19
<212> TYPE: DNA
<213> ORGANISM: Shigella

<400> SEQUENCE: 618
ccttcctccc cgctgaaag 19

<210> SEQ ID NO 619
<211> LENGTH: 19
<212> TYPE: DNA
<213> ORGANISM: Shigella sp.

<400> SEQUENCE: 619
cgaaacagtg ctctacccc 19

<210> SEQ ID NO 620
<211> LENGTH: 20
<212> TYPE: DNA
<213> ORGANISM: Staphylococcus

<400> SEQUENCE: 620
acagaccaga aagtcgcctt 20

<210> SEQ ID NO 621
<211> LENGTH: 21
<212> TYPE: DNA

<213> ORGANISM: Staphylococcus aureus

<400> SEQUENCE: 621
tcgacttgca tgtattaggc a 21

<210> SEQ ID NO 622
<211> LENGTH: 23
<212> TYPE: DNA
<213> ORGANISM: Staphylococcus epidermides

<400> SEQUENCE: 622
tcaagatttg gtaaggttct tcg 23

<210> SEQ ID NO 623
<211> LENGTH: 18
<212> TYPE: DNA
<213> ORGANISM: Stenotrophomonas maltophilia

<400> SEQUENCE: 623
cccagtatcc actgcagt 18

<210> SEQ ID NO 624
<211> LENGTH: 22
<212> TYPE: DNA
<213> ORGANISM: Streptococcus agalactiae

<400> SEQUENCE: 624
taacaacaga gctttacgat cc 22

<210> SEQ ID NO 625
<211> LENGTH: 23
<212> TYPE: DNA
<213> ORGANISM: Streptococcus pneumoniae

<400> SEQUENCE: 625
ctcttatgcg gtattagcta tcg 23

<210> SEQ ID NO 626
<211> LENGTH: 26
<212> TYPE: DNA
<213> ORGANISM: Streptococcus pneumoniae

<400> SEQUENCE: 626
cttttaagca aatgtcatgc aacatc 26

<210> SEQ ID NO 627
<211> LENGTH: 24
<212> TYPE: DNA
<213> ORGANISM: Streptococcus pyogenes

<400> SEQUENCE: 627
taacatgcgt tagtctctct tatg 24

<210> SEQ ID NO 628
<211> LENGTH: 21
<212> TYPE: DNA
<213> ORGANISM: Streptococcus sp.

<400> SEQUENCE: 628
ggttagttac cgtcacttgg t 21

<210> SEQ ID NO 629
<211> LENGTH: 23

<212> TYPE: DNA
<213> ORGANISM: Yersinia enterocolitica

<400> SEQUENCE: 629
ctgaaagtgc tttacaaccc gaa 23

<210> SEQ ID NO 630
<211> LENGTH: 16
<212> TYPE: DNA
<213> ORGANISM: Yersinia enterocolitica

<400> SEQUENCE: 630
ccckaaggtc ccccac 16

<210> SEQ ID NO 631
<211> LENGTH: 33
<212> TYPE: DNA
<213> ORGANISM: Achromobacter xylosoxidans

<400> SEQUENCE: 631
cccggggtcc aatagtgcaa ggtcttgccc ggg 33

<210> SEQ ID NO 632
<211> LENGTH: 38
<212> TYPE: DNA
<213> ORGANISM: Acinetobacter baumannii

<400> SEQUENCE: 632
ccggcgttca catccgactt aataagccgc ctcgccgg 38

<210> SEQ ID NO 633
<211> LENGTH: 30
<212> TYPE: DNA
<213> ORGANISM: Acinetobacter sp.

<400> SEQUENCE: 633
ccgtagacca tcctctccca tactctacgg 30

<210> SEQ ID NO 634
<211> LENGTH: 37
<212> TYPE: DNA
<213> ORGANISM: Bacillus cereus

<400> SEQUENCE: 634
ccgcgctgcg gttcaaaatg ttatccggta tgcgcgg 37

<210> SEQ ID NO 635
<211> LENGTH: 31
<212> TYPE: DNA
<213> ORGANISM: Bacteroides

<400> SEQUENCE: 635
ccgcggtgtc tcagttccaa tgtgggcgcg g 31

<210> SEQ ID NO 636
<211> LENGTH: 28
<212> TYPE: DNA
<213> ORGANISM: Burkholderia cepacia

<400> SEQUENCE: 636
cccggttggc aaccctctgt tccccggg 28

<210> SEQ ID NO 637

<211> LENGTH: 28
<212> TYPE: DNA
<213> ORGANISM: Campylobacter

<400> SEQUENCE: 637
cccgggccct aagcgtcctt ccaccggg 28

<210> SEQ ID NO 638
<211> LENGTH: 29
<212> TYPE: DNA
<213> ORGANISM: Citrobacter freundii

<400> SEQUENCE: 638
ccgcgccagt ttcggatgca gttccgcgg 29

<210> SEQ ID NO 639
<211> LENGTH: 32
<212> TYPE: DNA
<213> ORGANISM: Clostridium difficile

<400> SEQUENCE: 639
cgggtcgaag taaatcgctc aacttgcacc cg 32

<210> SEQ ID NO 640
<211> LENGTH: 31
<212> TYPE: DNA
<213> ORGANISM: Clostridium perfringens

<400> SEQUENCE: 640
ccgtcgaggt gttgaaaccc ccacacgacg g 31

<210> SEQ ID NO 641
<211> LENGTH: 28
<212> TYPE: DNA
<213> ORGANISM: Clostridium sp.

<400> SEQUENCE: 641
ccgcctttac gcccagtaaa tccggcgg 28

<210> SEQ ID NO 642
<211> LENGTH: 32
<212> TYPE: DNA
<213> ORGANISM: Corynebacterium sp.

<400> SEQUENCE: 642
cggcggcccg gaatttcaca gacgacccgc cg 32

<210> SEQ ID NO 643
<211> LENGTH: 30
<212> TYPE: DNA
<213> ORGANISM: Corynebacterium sp.

<400> SEQUENCE: 643
cgcggcccgg aatttcacag acgacccgcg 30

<210> SEQ ID NO 644
<211> LENGTH: 39
<212> TYPE: DNA
<213> ORGANISM: Escherichia coli

<400> SEQUENCE: 644
cctcgccaat gagcaaaggt attaacttta ctcgcgagg 39

<210> SEQ ID NO 645
<211> LENGTH: 34
<212> TYPE: DNA
<213> ORGANISM: Escherichia coli

<400> SEQUENCE: 645
ccgggcagtc acacagattg ctctgtgcgc ccgg 34

<210> SEQ ID NO 646
<211> LENGTH: 38
<212> TYPE: DNA
<213> ORGANISM: Enterobacter aerogenes

<400> SEQUENCE: 646
cgccggggaa gactctagcc tgccagtttc ccccggcg 38

<210> SEQ ID NO 647
<211> LENGTH: 31
<212> TYPE: DNA
<213> ORGANISM: Enterobacter sakazakii

<400> SEQUENCE: 647
ccgcctctcc cgcatctctg caggaaggcg g 31

<210> SEQ ID NO 648
<211> LENGTH: 31
<212> TYPE: DNA
<213> ORGANISM: Enterobacter sakazakii

<400> SEQUENCE: 648
ccgcctctcc cgcatctctg caggaaggcg g 31

<210> SEQ ID NO 649
<211> LENGTH: 33
<212> TYPE: DNA
<213> ORGANISM: Unknown
<220> FEATURE:
<223> OTHER INFORMATION: Enterobacteriaceae

<400> SEQUENCE: 649
ctcgcgcgtt tccagtagtt atccccccgc gag 33

<210> SEQ ID NO 650
<211> LENGTH: 28
<212> TYPE: DNA
<213> ORGANISM: Enterococcus

<400> SEQUENCE: 650
cggcccatca gcgacacccg aaaggccg 28

<210> SEQ ID NO 651
<211> LENGTH: 38
<212> TYPE: DNA
<213> ORGANISM: Enterococcus

<400> SEQUENCE: 651
ccgcgcgtta agaaaccgcc tgcgctcgct tcgcgcgg 38

<210> SEQ ID NO 652
<211> LENGTH: 31
<212> TYPE: DNA
<213> ORGANISM: Enterococcus faecalis

<400> SEQUENCE: 652
ccatcggcac tcgggaggaa agaagcgatg g 31

<210> SEQ ID NO 653
<211> LENGTH: 28
<212> TYPE: DNA
<213> ORGANISM: Enterococcus faecium

<400> SEQUENCE: 653
cgcgcctttc aaatcaaaac catgcgcg 28

<210> SEQ ID NO 654
<211> LENGTH: 33
<212> TYPE: DNA
<213> ORGANISM: Escherichia coli

<400> SEQUENCE: 654
cggcgagcaa gtcgcttcac ctacatatcg ccg 33

<210> SEQ ID NO 655
<211> LENGTH: 30
<212> TYPE: DNA
<213> ORGANISM: Haemophilus influenzae

<400> SEQUENCE: 655
cccggccgca ctttcatctt ccgatccggg 30

<210> SEQ ID NO 656
<211> LENGTH: 33
<212> TYPE: DNA
<213> ORGANISM: Inquilinus limosus

<400> SEQUENCE: 656
cgtagcgctt ggattcaagc ccgccccgct acg 33

<210> SEQ ID NO 657
<211> LENGTH: 30
<212> TYPE: DNA
<213> ORGANISM: Klebsiella pneumoniae

<400> SEQUENCE: 657
cgccacgtca cacccgaagg tgctgtggcg 30

<210> SEQ ID NO 658
<211> LENGTH: 35
<212> TYPE: DNA
<213> ORGANISM: Klebsiella oxytoca

<400> SEQUENCE: 658
cgcgcgccat gagcaagtca cttcacttac gcgcg 35

<210> SEQ ID NO 659
<211> LENGTH: 35
<212> TYPE: DNA
<213> ORGANISM: Klebsiella pneumoniae

<400> SEQUENCE: 659
cctccggtgt cacacccgaa ggtgctgtac ggagg 35

<210> SEQ ID NO 660
<211> LENGTH: 37
<212> TYPE: DNA
<213> ORGANISM: Klebsiella pneumoniae

<400> SEQUENCE: 660
ccgggctcca aatcgacatc gtttacggcg tgcccgg 37

<210> SEQ ID NO 661
<211> LENGTH: 31
<212> TYPE: DNA
<213> ORGANISM: Listeria monocytogenes

<400> SEQUENCE: 661
ccgggcgcat gcgccacact ttatcgcccg g 31

<210> SEQ ID NO 662
<211> LENGTH: 32
<212> TYPE: DNA
<213> ORGANISM: Mycobacterium avium

<400> SEQUENCE: 662
ccagggtcag ctccctccca aaaggtccct gg 32

<210> SEQ ID NO 663
<211> LENGTH: 29
<212> TYPE: DNA
<213> ORGANISM: Mycobacterium avium

<400> SEQUENCE: 663
cgcggtgctc cctcccaaaa gggaccgcg 29

<210> SEQ ID NO 664
<211> LENGTH: 28
<212> TYPE: DNA
<213> ORGANISM: Neisseria gonorrhoeae

<400> SEQUENCE: 664
cccggacccc gccaaccagc taaccggg 28

<210> SEQ ID NO 665
<211> LENGTH: 25
<212> TYPE: DNA
<213> ORGANISM: Neisseria meningitidis

<400> SEQUENCE: 665
caccgttatc ccccactact cggtg 25

<210> SEQ ID NO 666
<211> LENGTH: 27
<212> TYPE: DNA
<213> ORGANISM: Pandoraea apista

<400> SEQUENCE: 666
cgtgtacctc gcggcttggc gaacacg 27

<210> SEQ ID NO 667
<211> LENGTH: 29
<212> TYPE: DNA
<213> ORGANISM: Pandoraea sp.

<400> SEQUENCE: 667
ccgcggcctt gcagtcacga atgccgcgg 29

<210> SEQ ID NO 668
<211> LENGTH: 27
<212> TYPE: DNA
<213> ORGANISM: Pandoraea sp.

<400> SEQUENCE: 668
ccggccccga ggtattaacc cagccgg 27

<210> SEQ ID NO 669
<211> LENGTH: 27
<212> TYPE: DNA
<213> ORGANISM: Propionibacterium acnes

<400> SEQUENCE: 669
cccggacccc acaaaagcag ggccggg 27

<210> SEQ ID NO 670
<211> LENGTH: 31
<212> TYPE: DNA
<213> ORGANISM: Propionibacterium acnes

<400> SEQUENCE: 670
ccgggcaccc cacaaaagca gggcctcccg g 31

<210> SEQ ID NO 671
<211> LENGTH: 28
<212> TYPE: DNA
<213> ORGANISM: Proteus mirabilis

<400> SEQUENCE: 671
cgccgatagt gcaaggtccg aagcggcg 28

<210> SEQ ID NO 672
<211> LENGTH: 27
<212> TYPE: DNA
<213> ORGANISM: Proteus vulgaris

<400> SEQUENCE: 672
ccgccgtaga cgtcatgcgg taggcgg 27

<210> SEQ ID NO 673
<211> LENGTH: 34
<212> TYPE: DNA
<213> ORGANISM: Pseudomonas aerigunosa

<400> SEQUENCE: 673
cgcggcatta cccacccgag gtgctgtagc cgcg 34

<210> SEQ ID NO 674
<211> LENGTH: 30
<212> TYPE: DNA
<213> ORGANISM: Pseudomonas aeruginosa

<400> SEQUENCE: 674
cccggaagac gactcgtcat cagctccggg 30

<210> SEQ ID NO 675
<211> LENGTH: 28
<212> TYPE: DNA
<213> ORGANISM: Ralstonia sp.

<400> SEQUENCE: 675
cacgtgcatg aggccttgcg gtcacgtg 28

<210> SEQ ID NO 676
<211> LENGTH: 24
<212> TYPE: DNA
<213> ORGANISM: Ralstonia sp.

<400> SEQUENCE: 676
cgttcggtct tgcacaaccg cacg 24

<210> SEQ ID NO 677
<211> LENGTH: 37
<212> TYPE: DNA
<213> ORGANISM: Ralstonia sp.

<400> SEQUENCE: 677
ccgacgttct aatgcatctc tgcttcgtta gcgtcgg 37

<210> SEQ ID NO 678
<211> LENGTH: 31
<212> TYPE: DNA
<213> ORGANISM: Staphylococcus lugdunensis

<400> SEQUENCE: 678
cgcgcctcta gagcggtcaa aggatggcgc g 31

<210> SEQ ID NO 679
<211> LENGTH: 29
<212> TYPE: DNA
<213> ORGANISM: Salmonella

<400> SEQUENCE: 679
cgctccttca cctacgtgtc agcggagcg 29

<210> SEQ ID NO 680
<211> LENGTH: 33
<212> TYPE: DNA
<213> ORGANISM: Serratia marcescens

<400> SEQUENCE: 680
ccgggcgtat taagctcacc accttcctcc cgg 33

<210> SEQ ID NO 681
<211> LENGTH: 31
<212> TYPE: DNA
<213> ORGANISM: Shigella

<400> SEQUENCE: 681
ccggcaagtc gggatgaccc ccttgcgccg g 31

<210> SEQ ID NO 682
<211> LENGTH: 35
<212> TYPE: DNA
<213> ORGANISM: Shigella

<400> SEQUENCE: 682
cccgggtgag caaaggtatt aactttactc ccggg 35

<210> SEQ ID NO 683
<211> LENGTH: 35
<212> TYPE: DNA
<213> ORGANISM: Shigella

<400> SEQUENCE: 683
cccgggtgag caaaggtatt aactttactc ccggg 35

<210> SEQ ID NO 684
<211> LENGTH: 31
<212> TYPE: DNA

<213> ORGANISM: Shigella sp.

<400> SEQUENCE: 684
ccgccaagtc gggatgaccc ccttgcggcg g 31

<210> SEQ ID NO 685
<211> LENGTH: 28
<212> TYPE: DNA
<213> ORGANISM: Staphylococcus

<400> SEQUENCE: 685
ccaactttcg cacatcagcg tcagttgg 28

<210> SEQ ID NO 686
<211> LENGTH: 27
<212> TYPE: DNA
<213> ORGANISM: Staphylococcus aureus

<400> SEQUENCE: 686
cctgcaagct tctcgtccgt tcgcagg 27

<210> SEQ ID NO 687
<211> LENGTH: 30
<212> TYPE: DNA
<213> ORGANISM: Staphylococcus epidermides

<400> SEQUENCE: 687
ccgcgtctag aggggtcaga ggatgcgcgg 30

<210> SEQ ID NO 688
<211> LENGTH: 32
<212> TYPE: DNA
<213> ORGANISM: Stenotrophomonas maltophilia

<400> SEQUENCE: 688
cccggaccct ctaccacact ctagtcgccg gg 32

<210> SEQ ID NO 689
<211> LENGTH: 31
<212> TYPE: DNA
<213> ORGANISM: Streptococcus agalactiae

<400> SEQUENCE: 689
ccgctactcc taccaacgtt cttctcagcg g 31

<210> SEQ ID NO 690
<211> LENGTH: 36
<212> TYPE: DNA
<213> ORGANISM: Streptococcus pneumoniae

<400> SEQUENCE: 690
ccgttaagca aatgtcatgc aacatcyact taacgg 36

<210> SEQ ID NO 691
<211> LENGTH: 31
<212> TYPE: DNA
<213> ORGANISM: Streptococcus pneumoniae

<400> SEQUENCE: 691
ccgggctggt agtgatgcaa gtgcaccccg g 31

<210> SEQ ID NO 692
<211> LENGTH: 34

<212> TYPE: DNA
<213> ORGANISM: Streptococcus pyogenes

<400> SEQUENCE: 692
cgctcgagca attgcccctt ttaaattacg agcg 34

<210> SEQ ID NO 693
<211> LENGTH: 36
<212> TYPE: DNA
<213> ORGANISM: Streptococcus sp.

<400> SEQUENCE: 693
ccgggcgcac gtagttagcc gtccctttct gcccgg 36

<210> SEQ ID NO 694
<211> LENGTH: 36
<212> TYPE: DNA
<213> ORGANISM: Yersinia enterocolitica

<400> SEQUENCE: 694
cgccgggaag ttattggcct tcctcctcgc ccggcg 36

<210> SEQ ID NO 695
<211> LENGTH: 29
<212> TYPE: DNA
<213> ORGANISM: Yersinia enterocolitica

<400> SEQUENCE: 695
ccgggcacat ccgatggcgt gaggcccgg 29

<210> SEQ ID NO 696
<211> LENGTH: 19
<212> TYPE: DNA
<213> ORGANISM: Achromobacter xylosoxidans

<400> SEQUENCE: 696
ctaatccgat atcggccgc 19

<210> SEQ ID NO 697
<211> LENGTH: 19
<212> TYPE: DNA
<213> ORGANISM: Acinetobacter baumannii

<400> SEQUENCE: 697
ccaagttaag ctcggggat 19

<210> SEQ ID NO 698
<211> LENGTH: 20
<212> TYPE: DNA
<213> ORGANISM: Acinetobacter sp.

<400> SEQUENCE: 698
accgctacac ctggaattct 20

<210> SEQ ID NO 699
<211> LENGTH: 21
<212> TYPE: DNA
<213> ORGANISM: Bacillus cereus

<400> SEQUENCE: 699
ccgcctttca atttcgaacc a 21

<210> SEQ ID NO 700

<211> LENGTH: 18
<212> TYPE: DNA
<213> ORGANISM: Bacteroides

<400> SEQUENCE: 700
cccgtaggag tttggacc 18

<210> SEQ ID NO 701
<211> LENGTH: 18
<212> TYPE: DNA
<213> ORGANISM: Burkholderia cepacia

<400> SEQUENCE: 701
gattrgctcc ccctcgcg 18

<210> SEQ ID NO 702
<211> LENGTH: 17
<212> TYPE: DNA
<213> ORGANISM: Campylobacter

<400> SEQUENCE: 702
atccgctagc cccctta 17

<210> SEQ ID NO 703
<211> LENGTH: 20
<212> TYPE: DNA
<213> ORGANISM: Citrobacter freundii

<400> SEQUENCE: 703
cctctacaag actctagcct 20

<210> SEQ ID NO 704
<211> LENGTH: 18
<212> TYPE: DNA
<213> ORGANISM: Clostridium difficile

<400> SEQUENCE: 704
ccgtccgccg ctctttac 18

<210> SEQ ID NO 705
<211> LENGTH: 16
<212> TYPE: DNA
<213> ORGANISM: Clostridium perfringens

<400> SEQUENCE: 705
cgttagcggc ggcacg 16

<210> SEQ ID NO 706
<211> LENGTH: 20
<212> TYPE: DNA
<213> ORGANISM: Clostridium sp.

<400> SEQUENCE: 706
ttaatcatcc gcctacgcac 20

<210> SEQ ID NO 707
<211> LENGTH: 18
<212> TYPE: DNA
<213> ORGANISM: Corynebacterium sp.

<400> SEQUENCE: 707
gcctgcacgc ccgaagcg 18

<210> SEQ ID NO 708
<211> LENGTH: 19
<212> TYPE: DNA
<213> ORGANISM: Corynebacterium sp.

<400> SEQUENCE: 708
tgcacgcccg aagttaagc 19

<210> SEQ ID NO 709
<211> LENGTH: 19
<212> TYPE: DNA
<213> ORGANISM: Escherichia coli

<400> SEQUENCE: 709
cttcttctgc gggtaacgt 19

<210> SEQ ID NO 710
<211> LENGTH: 22
<212> TYPE: DNA
<213> ORGANISM: Escherichia coli

<400> SEQUENCE: 710
acccattata caaaaggtac gc 22

<210> SEQ ID NO 711
<211> LENGTH: 20
<212> TYPE: DNA
<213> ORGANISM: Enterobacter aerogenes

<400> SEQUENCE: 711
aatgcagttc ccaggttgag 20

<210> SEQ ID NO 712
<211> LENGTH: 21
<212> TYPE: DNA
<213> ORGANISM: Enterobacter sakazakii

<400> SEQUENCE: 712
cttctctgga tgtcaagacc a 21

<210> SEQ ID NO 713
<211> LENGTH: 21
<212> TYPE: DNA
<213> ORGANISM: Enterobacter sakazakii

<400> SEQUENCE: 713
cttctctgga tgtcaagacc a 21

<210> SEQ ID NO 714
<211> LENGTH: 22
<212> TYPE: DNA
<213> ORGANISM: Unknown
<220> FEATURE:
<223> OTHER INFORMATION: Enterobacteriaceae

<400> SEQUENCE: 714
gacgttatgc ggtattagct ac 22

<210> SEQ ID NO 715
<211> LENGTH: 17
<212> TYPE: DNA
<213> ORGANISM: Enterococcus

<400> SEQUENCE: 715
accgcgggtc catccat 17

<210> SEQ ID NO 716
<211> LENGTH: 19
<212> TYPE: DNA
<213> ORGANISM: Enterococcus

<400> SEQUENCE: 716
gggggctttc acatcagac 19

<210> SEQ ID NO 717
<211> LENGTH: 22
<212> TYPE: DNA
<213> ORGANISM: Enterococcus faecalis

<400> SEQUENCE: 717
tcctctttcc aattgagtgc aa 22

<210> SEQ ID NO 718
<211> LENGTH: 19
<212> TYPE: DNA
<213> ORGANISM: Enterococcus faecium

<400> SEQUENCE: 718
ccatcagcga cacccgaaa 19

<210> SEQ ID NO 719
<211> LENGTH: 22
<212> TYPE: DNA
<213> ORGANISM: Escherichia coli

<400> SEQUENCE: 719
cttcgactga tttcagctcc ac 22

<210> SEQ ID NO 720
<211> LENGTH: 18
<212> TYPE: DNA
<213> ORGANISM: Haemophilus influenzae

<400> SEQUENCE: 720
gcatgcggcc tctcagtc 18

<210> SEQ ID NO 721
<211> LENGTH: 19
<212> TYPE: DNA
<213> ORGANISM: Inquilinus limosus

<400> SEQUENCE: 721
gggaattcca ccaccctct 19

<210> SEQ ID NO 722
<211> LENGTH: 23
<212> TYPE: DNA
<213> ORGANISM: Klebsiella pneumoniae

<400> SEQUENCE: 722
acccattata caaaaggtac gca 23

<210> SEQ ID NO 723
<211> LENGTH: 23
<212> TYPE: DNA
<213> ORGANISM: Klebsiella oxytoca

<400> SEQUENCE: 723
ggtatcttcg actgatttca gct 23

<210> SEQ ID NO 724
<211> LENGTH: 23
<212> TYPE: DNA
<213> ORGANISM: Klebsiella pneumoniae

<400> SEQUENCE: 724
acccattata caaaaggtac gca 23

<210> SEQ ID NO 725
<211> LENGTH: 18
<212> TYPE: DNA
<213> ORGANISM: Klebsiella pneumoniae

<400> SEQUENCE: 725
acgcctcaag ggcacaac 18

<210> SEQ ID NO 726
<211> LENGTH: 23
<212> TYPE: DNA
<213> ORGANISM: Listeria monocytogenes

<400> SEQUENCE: 726
cgaaaccatc tttcaaaagc gtg 23

<210> SEQ ID NO 727
<211> LENGTH: 18
<212> TYPE: DNA
<213> ORGANISM: Mycobacterium avium

<400> SEQUENCE: 727
cgccgatccc accttcga 18

<210> SEQ ID NO 728
<211> LENGTH: 18
<212> TYPE: DNA
<213> ORGANISM: Mycobacterium avium

<400> SEQUENCE: 728
ccgatcccac cttcgaca 18

<210> SEQ ID NO 729
<211> LENGTH: 17
<212> TYPE: DNA
<213> ORGANISM: Neisseria gonorrhoeae

<400> SEQUENCE: 729
cgccttggtg ggccttt 17

<210> SEQ ID NO 730
<211> LENGTH: 24
<212> TYPE: DNA
<213> ORGANISM: Neisseria meningitidis

<400> SEQUENCE: 730
ggtattagct gatctttcga tcag 24

<210> SEQ ID NO 731
<211> LENGTH: 20
<212> TYPE: DNA
<213> ORGANISM: Pandoraea apista

<400> SEQUENCE: 731
ggttttctgg ggttagctcc 20

<210> SEQ ID NO 732
<211> LENGTH: 18
<212> TYPE: DNA
<213> ORGANISM: Pandoraea sp.

<400> SEQUENCE: 732
cccctctgcc atactcta 18

<210> SEQ ID NO 733
<211> LENGTH: 20
<212> TYPE: DNA
<213> ORGANISM: Pandoraea sp.

<400> SEQUENCE: 733
ttcttccggt accgtcatcc 20

<210> SEQ ID NO 734
<211> LENGTH: 20
<212> TYPE: DNA
<213> ORGANISM: Propionibacterium acnes

<400> SEQUENCE: 734
cagtcaaggg caggttactc 20

<210> SEQ ID NO 735
<211> LENGTH: 20
<212> TYPE: DNA
<213> ORGANISM: Propionibacterium acnes

<400> SEQUENCE: 735
cagtcaaggg caggttactc 20

<210> SEQ ID NO 736
<211> LENGTH: 21
<212> TYPE: DNA
<213> ORGANISM: Proteus mirabilis

<400> SEQUENCE: 736
gctaatccca tatgggttca t 21

<210> SEQ ID NO 737
<211> LENGTH: 18
<212> TYPE: DNA
<213> ORGANISM: Proteus vulgaris

<400> SEQUENCE: 737
aagagcccct gctttggt 18

<210> SEQ ID NO 738
<211> LENGTH: 18
<212> TYPE: DNA
<213> ORGANISM: Pseudomonas aerigunosa

<400> SEQUENCE: 738
ggcagtctcc ttagagtg 18

<210> SEQ ID NO 739
<211> LENGTH: 18
<212> TYPE: DNA
<213> ORGANISM: Pseudomonas aeruginosa

<400> SEQUENCE: 739
acccacttcg tcatctaa 18

<210> SEQ ID NO 740
<211> LENGTH: 18
<212> TYPE: DNA
<213> ORGANISM: Ralstonia sp.

<400> SEQUENCE: 740
acatcggccg ctcctata 18

<210> SEQ ID NO 741
<211> LENGTH: 20
<212> TYPE: DNA
<213> ORGANISM: Ralstonia sp.

<400> SEQUENCE: 741
ttaagcccgg ggatttcaca 20

<210> SEQ ID NO 742
<211> LENGTH: 21
<212> TYPE: DNA
<213> ORGANISM: Ralstonia sp.

<400> SEQUENCE: 742
tccactttct ctttcgagca c 21

<210> SEQ ID NO 743
<211> LENGTH: 19
<212> TYPE: DNA
<213> ORGANISM: Staphylococcus lugdunensis

<400> SEQUENCE: 743
ccgaagggga agactctat 19

<210> SEQ ID NO 744
<211> LENGTH: 21
<212> TYPE: DNA
<213> ORGANISM: Salmonella

<400> SEQUENCE: 744
ttcagctccr tgagtaaatc a 21

<210> SEQ ID NO 745
<211> LENGTH: 23
<212> TYPE: DNA
<213> ORGANISM: Serratia marcescens

<400> SEQUENCE: 745
tgcgagtaac gtcaattgat gag 23

<210> SEQ ID NO 746
<211> LENGTH: 20
<212> TYPE: DNA
<213> ORGANISM: Shigella

<400> SEQUENCE: 746
gcagtttgca tcgggttggt 20

<210> SEQ ID NO 747
<211> LENGTH: 25
<212> TYPE: DNA

<213> ORGANISM: Shigella

<400> SEQUENCE: 747
gtgcttcttc tgcgggtaac gtcaa 25

<210> SEQ ID NO 748
<211> LENGTH: 25
<212> TYPE: DNA
<213> ORGANISM: Shigella

<400> SEQUENCE: 748
gtgcttcttc tgcgggtaac gtcaa 25

<210> SEQ ID NO 749
<211> LENGTH: 20
<212> TYPE: DNA
<213> ORGANISM: Shigella sp.

<400> SEQUENCE: 749
gcagtttgca tcgggttggt 20

<210> SEQ ID NO 750
<211> LENGTH: 20
<212> TYPE: DNA
<213> ORGANISM: Staphylococcus

<400> SEQUENCE: 750
atcctgtttg atccccacgc 20

<210> SEQ ID NO 751
<211> LENGTH: 20
<212> TYPE: DNA
<213> ORGANISM: Staphylococcus aureus

<400> SEQUENCE: 751
ccgccgctaa catcagagaa 20

<210> SEQ ID NO 752
<211> LENGTH: 20
<212> TYPE: DNA
<213> ORGANISM: Staphylococcus epidermides

<400> SEQUENCE: 752
ccgaagggga aaactctatc 20

<210> SEQ ID NO 753
<211> LENGTH: 18
<212> TYPE: DNA
<213> ORGANISM: Stenotrophomonas maltophilia

<400> SEQUENCE: 753
acaccaggaa ttccgcta 18

<210> SEQ ID NO 754
<211> LENGTH: 22
<212> TYPE: DNA
<213> ORGANISM: Streptococcus agalactiae

<400> SEQUENCE: 754
accgtcactt ggtagatttt cc 22

<210> SEQ ID NO 755
<211> LENGTH: 21

<212> TYPE: DNA
<213> ORGANISM: Streptococcus pneumoniae

<400> SEQUENCE: 755
tagtgatgca agtgcacctt t 21

<210> SEQ ID NO 756
<211> LENGTH: 21
<212> TYPE: DNA
<213> ORGANISM: Streptococcus pneumoniae

<400> SEQUENCE: 756
gctaatacaa cgcaggtcca t 21

<210> SEQ ID NO 757
<211> LENGTH: 21
<212> TYPE: DNA
<213> ORGANISM: Streptococcus pyogenes

<400> SEQUENCE: 757
acgcaggtcc atctcatagt g 21

<210> SEQ ID NO 758
<211> LENGTH: 19
<212> TYPE: DNA
<213> ORGANISM: Streptococcus sp.

<400> SEQUENCE: 758
cgtattaccg cggctgctg 19

<210> SEQ ID NO 759
<211> LENGTH: 25
<212> TYPE: DNA
<213> ORGANISM: Yersinia enterocolitica

<400> SEQUENCE: 759
gtaacgtcaa tccaacaacg tatta 25

<210> SEQ ID NO 760
<211> LENGTH: 21
<212> TYPE: DNA
<213> ORGANISM: Yersinia enterocolitica

<400> SEQUENCE: 760
tactagctaa tcccatctgg g 21

<210> SEQ ID NO 761
<211> LENGTH: 19
<212> TYPE: DNA
<213> ORGANISM: Achromobacter xylosoxidans

<400> SEQUENCE: 761
ccgttacccc accaactag 19

<210> SEQ ID NO 762
<211> LENGTH: 23
<212> TYPE: DNA
<213> ORGANISM: Acinetobacter baumannii

<400> SEQUENCE: 762
ctcaccagta tcgaatgcaa ttc 23

<210> SEQ ID NO 763

<211> LENGTH: 21
<212> TYPE: DNA
<213> ORGANISM: Acinetobacter sp.

<400> SEQUENCE: 763
ctccagatct ctacgcattt c 21

<210> SEQ ID NO 764
<211> LENGTH: 21
<212> TYPE: DNA
<213> ORGANISM: Bacillus cereus

<400> SEQUENCE: 764
atccataagt gacagccgaa g 21

<210> SEQ ID NO 765
<211> LENGTH: 20
<212> TYPE: DNA
<213> ORGANISM: Bacteroides

<400> SEQUENCE: 765
aatattcctc actgctgcct 20

<210> SEQ ID NO 766
<211> LENGTH: 18
<212> TYPE: DNA
<213> ORGANISM: Burkholderia cepacia

<400> SEQUENCE: 766
ctacgatcgg ttttctgg 18

<210> SEQ ID NO 767
<211> LENGTH: 20
<212> TYPE: DNA
<213> ORGANISM: Campylobacter

<400> SEQUENCE: 767
gaccttagac tagcacttcc 20

<210> SEQ ID NO 768
<211> LENGTH: 20
<212> TYPE: DNA
<213> ORGANISM: Citrobacter freundii

<400> SEQUENCE: 768
tacacctgga attctacccc 20

<210> SEQ ID NO 769
<211> LENGTH: 20
<212> TYPE: DNA
<213> ORGANISM: Clostridium difficile

<400> SEQUENCE: 769
gttacccacg cgttactcac 20

<210> SEQ ID NO 770
<211> LENGTH: 20
<212> TYPE: DNA
<213> ORGANISM: Clostridium perfringens

<400> SEQUENCE: 770
cccaggcgga atacttaatg 20

<210> SEQ ID NO 771
<211> LENGTH: 18
<212> TYPE: DNA
<213> ORGANISM: Clostridium sp.

<400> SEQUENCE: 771
cggggatttc acatccca 18

<210> SEQ ID NO 772
<211> LENGTH: 21
<212> TYPE: DNA
<213> ORGANISM: Corynebacterium sp.

<400> SEQUENCE: 772
cactcaagtt atgcccgtat c 21

<210> SEQ ID NO 773
<211> LENGTH: 20
<212> TYPE: DNA
<213> ORGANISM: Corynebacterium sp.

<400> SEQUENCE: 773
caagttatgc ccgtatcgcc 20

<210> SEQ ID NO 774
<211> LENGTH: 18
<212> TYPE: DNA
<213> ORGANISM: Escherichia coli

<400> SEQUENCE: 774
gcacggagtt agccggtg 18

<210> SEQ ID NO 775
<211> LENGTH: 23
<212> TYPE: DNA
<213> ORGANISM: Escherichia coli

<400> SEQUENCE: 775
ttgctacaga atataagtcg ctg 23

<210> SEQ ID NO 776
<211> LENGTH: 20
<212> TYPE: DNA
<213> ORGANISM: Enterobacter aerogenes

<400> SEQUENCE: 776
gcatttcacc gctacacctg 20

<210> SEQ ID NO 777
<211> LENGTH: 17
<212> TYPE: DNA
<213> ORGANISM: Enterobacter sakazakii

<400> SEQUENCE: 777
agccatgcag cacctgt 17

<210> SEQ ID NO 778
<211> LENGTH: 17
<212> TYPE: DNA
<213> ORGANISM: Enterobacter sakazakii

<400> SEQUENCE: 778
agccatgcag cacctgt 17

<210> SEQ ID NO 779
<211> LENGTH: 18
<212> TYPE: DNA
<213> ORGANISM: Unknown
<220> FEATURE:
<223> OTHER INFORMATION: Enterobacteriaceae

<400> SEQUENCE: 779 cccccctcttt ggtcttgc 18

<210> SEQ ID NO 780
<211> LENGTH: 21
<212> TYPE: DNA
<213> ORGANISM: Enterococcus

<400> SEQUENCE: 780
acctcaccaa ctagctaatg c 21

<210> SEQ ID NO 781
<211> LENGTH: 15
<212> TYPE: DNA
<213> ORGANISM: Enterococcus

<400> SEQUENCE: 781
ctccccggtt gagcc 15

<210> SEQ ID NO 782
<211> LENGTH: 17
<212> TYPE: DNA
<213> ORGANISM: Enterococcus faecalis

<400> SEQUENCE: 782
actcacccgt ccgccac 17

<210> SEQ ID NO 783
<211> LENGTH: 17
<212> TYPE: DNA
<213> ORGANISM: Enterococcus faecium

<400> SEQUENCE: 783
atgcaccgcg ggtccat 17

<210> SEQ ID NO 784
<211> LENGTH: 18
<212> TYPE: DNA
<213> ORGANISM: Escherichia coli

<400> SEQUENCE: 784
gttgcagcca gctggtat 18

<210> SEQ ID NO 785
<211> LENGTH: 19
<212> TYPE: DNA
<213> ORGANISM: Haemophilus influenzae

<400> SEQUENCE: 785
cacttgggct catcctatg 19

<210> SEQ ID NO 786
<211> LENGTH: 23
<212> TYPE: DNA
<213> ORGANISM: Inquilinus limosus

<400> SEQUENCE: 786
tctacgaatt tcacctctac act 23

<210> SEQ ID NO 787
<211> LENGTH: 24
<212> TYPE: DNA
<213> ORGANISM: Klebsiella pneumoniae

<400> SEQUENCE: 787
cttgctacag aatataagtc gctg 24

<210> SEQ ID NO 788
<211> LENGTH: 25
<212> TYPE: DNA
<213> ORGANISM: Klebsiella oxytoca

<400> SEQUENCE: 788
ttttaataaa cagttgcagc cagct 25

<210> SEQ ID NO 789
<211> LENGTH: 24
<212> TYPE: DNA
<213> ORGANISM: Klebsiella pneumoniae

<400> SEQUENCE: 789
cttgctacag aatataagtc gctg 24

<210> SEQ ID NO 790
<211> LENGTH: 17
<212> TYPE: DNA
<213> ORGANISM: Klebsiella pneumoniae

<400> SEQUENCE: 790
cgttagctcc ggaagcc 17

<210> SEQ ID NO 791
<211> LENGTH: 20
<212> TYPE: DNA
<213> ORGANISM: Listeria monocytogenes

<400> SEQUENCE: 791
gcccatctgt aagcgatagc 20

<210> SEQ ID NO 792
<211> LENGTH: 22
<212> TYPE: DNA
<213> ORGANISM: Mycobacterium avium

<400> SEQUENCE: 792
cttgttacga cttcgtccca at 22

<210> SEQ ID NO 793
<211> LENGTH: 21
<212> TYPE: DNA
<213> ORGANISM: Mycobacterium avium

<400> SEQUENCE: 793
gttacgactt cgtcccaatc g 21

<210> SEQ ID NO 794
<211> LENGTH: 19
<212> TYPE: DNA
<213> ORGANISM: Neisseria gonorrhoeae

<400> SEQUENCE: 794
cagacccgct actgatcgt 19

<210> SEQ ID NO 795
<211> LENGTH: 21
<212> TYPE: DNA
<213> ORGANISM: Neisseria meningitidis

<400> SEQUENCE: 795
tttctctctc aagacgtatg c 21

<210> SEQ ID NO 796
<211> LENGTH: 19
<212> TYPE: DNA
<213> ORGANISM: Pandoraea apista

<400> SEQUENCE: 796
tgcgatccgg actacgatc 19

<210> SEQ ID NO 797
<211> LENGTH: 21
<212> TYPE: DNA
<213> ORGANISM: Pandoraea sp.

<400> SEQUENCE: 797
tgctacacgt ggaattctac c 21

<210> SEQ ID NO 798
<211> LENGTH: 20
<212> TYPE: DNA
<213> ORGANISM: Pandoraea sp.

<400> SEQUENCE: 798
acgtagttag ccggtgctta 20

<210> SEQ ID NO 799
<211> LENGTH: 20
<212> TYPE: DNA
<213> ORGANISM: Propionibacterium acnes

<400> SEQUENCE: 799
acgtgttact cacccgttcg 20

<210> SEQ ID NO 800
<211> LENGTH: 20
<212> TYPE: DNA
<213> ORGANISM: Propionibacterium acnes

<400> SEQUENCE: 800
acgtgttact cacccgttcg 20

<210> SEQ ID NO 801
<211> LENGTH: 19
<212> TYPE: DNA
<213> ORGANISM: Proteus mirabilis

<400> SEQUENCE: 801
gcctttaccc cacctacta 19

<210> SEQ ID NO 802
<211> LENGTH: 18
<212> TYPE: DNA
<213> ORGANISM: Proteus vulgaris

<400> SEQUENCE: 802
ccgatagcgc aaggtccg 18

<210> SEQ ID NO 803
<211> LENGTH: 19
<212> TYPE: DNA
<213> ORGANISM: Pseudomonas aerigunosa

<400> SEQUENCE: 803
cttcctccgg tttgtcacc 19

<210> SEQ ID NO 804
<211> LENGTH: 18
<212> TYPE: DNA
<213> ORGANISM: Pseudomonas aeruginosa

<400> SEQUENCE: 804
tcttggaagc atggcatc 18

<210> SEQ ID NO 805
<211> LENGTH: 22
<212> TYPE: DNA
<213> ORGANISM: Ralstonia sp.

<400> SEQUENCE: 805
acctcaccaa ctagctaatc ag 22

<210> SEQ ID NO 806
<211> LENGTH: 20
<212> TYPE: DNA
<213> ORGANISM: Ralstonia sp.

<400> SEQUENCE: 806
tcaccaatgc aattcccagg 20

<210> SEQ ID NO 807
<211> LENGTH: 17
<212> TYPE: DNA
<213> ORGANISM: Ralstonia sp.

<400> SEQUENCE: 807
gccatgcagc acctgtg 17

<210> SEQ ID NO 808
<211> LENGTH: 19
<212> TYPE: DNA
<213> ORGANISM: Staphylococcus lugdunensis

<400> SEQUENCE: 808
ccacctgtca ctttgtccc 19

<210> SEQ ID NO 809
<211> LENGTH: 19
<212> TYPE: DNA
<213> ORGANISM: Salmonella

<400> SEQUENCE: 809
gctggtatct tcgrctgac 19

<210> SEQ ID NO 810
<211> LENGTH: 19
<212> TYPE: DNA

<213> ORGANISM: Serratia marcescens

<400> SEQUENCE: 810
agttagccgg tgcttcttc 19

<210> SEQ ID NO 811
<211> LENGTH: 23
<212> TYPE: DNA
<213> ORGANISM: Shigella

<400> SEQUENCE: 811
cgtgataaca ttctccggta ttc 23

<210> SEQ ID NO 812
<211> LENGTH: 23
<212> TYPE: DNA
<213> ORGANISM: Shigella

<400> SEQUENCE: 812
ggctgctggc acggagttag ccg 23

<210> SEQ ID NO 813
<211> LENGTH: 17
<212> TYPE: DNA
<213> ORGANISM: Shigella

<400> SEQUENCE: 813
tggcacggag ttagccg 17

<210> SEQ ID NO 814
<211> LENGTH: 23
<212> TYPE: DNA
<213> ORGANISM: Shigella sp.

<400> SEQUENCE: 814
cgtgataaca ttctccggta ttc 23

<210> SEQ ID NO 815
<211> LENGTH: 20
<212> TYPE: DNA
<213> ORGANISM: Staphylococcus

<400> SEQUENCE: 815
gtggactacc agggtatcta 20

<210> SEQ ID NO 816
<211> LENGTH: 20
<212> TYPE: DNA
<213> ORGANISM: Staphylococcus aureus

<400> SEQUENCE: 816
ccgccgctaa catcagagaa 20

<210> SEQ ID NO 817
<211> LENGTH: 18
<212> TYPE: DNA
<213> ORGANISM: Staphylococcus epidermides

<400> SEQUENCE: 817
cacctgtcac tctgtccc 18

<210> SEQ ID NO 818
<211> LENGTH: 18

<212> TYPE: DNA
<213> ORGANISM: Stenotrophomonas maltophilia

<400> SEQUENCE: 818
tctacgcatt tcactgct 18

<210> SEQ ID NO 819
<211> LENGTH: 20
<212> TYPE: DNA
<213> ORGANISM: Streptococcus agalactiae

<400> SEQUENCE: 819
ccgtcccttt ctggttagtt 20

<210> SEQ ID NO 820
<211> LENGTH: 19
<212> TYPE: DNA
<213> ORGANISM: Streptococcus pneumoniae

<400> SEQUENCE: 820
acaacgcagg tccatctgg 19

<210> SEQ ID NO 821
<211> LENGTH: 19
<212> TYPE: DNA
<213> ORGANISM: Streptococcus pneumoniae

<400> SEQUENCE: 821
gccgttaccc caccaacta 19

<210> SEQ ID NO 822
<211> LENGTH: 23
<212> TYPE: DNA
<213> ORGANISM: Streptococcus pyogenes

<400> SEQUENCE: 822
tacctcacca actagctaat aca 23

<210> SEQ ID NO 823
<211> LENGTH: 18
<212> TYPE: DNA
<213> ORGANISM: Streptococcus sp.

<400> SEQUENCE: 823
gacaacgctc gggaccta 18

<210> SEQ ID NO 824
<211> LENGTH: 18
<212> TYPE: DNA
<213> ORGANISM: Yersinia enterocolitica

<400> SEQUENCE: 824
ccggtgcttc ttctgcga 18

<210> SEQ ID NO 825
<211> LENGTH: 18
<212> TYPE: DNA
<213> ORGANISM: Yersinia enterocolitica

<400> SEQUENCE: 825
gtgagccatt accccacc 18